US007501486B2

(12) United States Patent
Zhang et al.

(10) Patent No.: US 7,501,486 B2
(45) Date of Patent: Mar. 10, 2009

(54) PEPTIDES THAT SELECTIVELY HOME TO HEART VASCULATURE AND RELATED CONJUGATES AND METHODS

(75) Inventors: Lianglin Zhang, La Jolla, CA (US); Jason A. Hoffman, La Jolla, CA (US); Erkki Ruoslahti, Buellton, CA (US)

(73) Assignee: Burnham Institute for Medical Research, La Jolla, CA (US)

( * ) Notice: Subject to any disclaimer, the term of this patent is extended or adjusted under 35 U.S.C. 154(b) by 331 days.

(21) Appl. No.: 11/222,370

(22) Filed: Sep. 7, 2005

(65) Prior Publication Data

US 2006/0160743 A1 Jul. 20, 2006

Related U.S. Application Data

(60) Provisional application No. 60/714,515, filed on Sep. 7, 2004.

(51) Int. Cl.
*A61K 38/00* (2006.01)
*C07K 7/00* (2006.01)

(52) U.S. Cl. ......................... 530/330; 530/324; 514/17; 514/12

(58) Field of Classification Search ................. 530/330, 530/324; 514/17, 12
See application file for complete search history.

(56) References Cited

U.S. PATENT DOCUMENTS

| | | | | |
|---|---|---|---|---|
| 6,303,573 | B1 | 10/2001 | Ruoslahti et al. | |
| 6,551,795 | B1 * | 4/2003 | Rubenfield et al. | 435/69.1 |
| 6,759,046 | B1 * | 7/2004 | Gaudernack et al. | 424/184.1 |
| 2003/0078396 | A1 * | 4/2003 | Gaiger et al. | 536/23.1 |
| 2004/0123343 | A1 * | 6/2004 | La Rosa et al. | 800/278 |
| 2004/0172684 | A1 * | 9/2004 | Kovalic et al. | 800/284 |

FOREIGN PATENT DOCUMENTS

| | | | |
|---|---|---|---|
| WO | WO 00/75174 | | 12/2000 |
| WO | WO02057420 | * | 7/2002 |

OTHER PUBLICATIONS

Arap et al., "Chemotherapy targeted to tumor vasculature," *Curr. Opin. Oncol.* 10:560-565 (1998).

Gromova et al., "Bc10: A novel human bladder cancer-associated protein with a conserved genomic structure downregulated in invasive cancer," *Int. J. Cancer* 98:539-546 (2002).

Hoffman et al., "In vivo and ex vivo selections using phage-displayed libraries," in Clarkson and Lowman (Eds.) *Phage Display: A Practical Approach* pp. 171-192, Oxford, U.K.: Oxford University Press (2004).

Hoffman et al., "Progressive vascular changes in a transgenic mouse model of squamous cell carcinoma," *Cancer Cell* 4:383-391 (2003).

Joyce et al., "Stage-specific vascular markers revealed by phage display in a mouse model of pancreatic islet tumorigenesis," *Cancer Cell* 4:393-403 (2003).

Karim et al., "Human ESP1/CRP2, a member of the LIM domain protein family: characterization of the cDNA and assignment of the gene locus to chromosome 14q32.3," *Genomics* 31:167-176 (1996).

Laakkonen et al., "A tumor-homing peptide with a targeting specificity related to lymphatic vessels," *Nat. Med.* 8:751-755 (2002).

Laakkonen et al., Antitumor activity of a homing peptide that targets tumor lymphatics and tumor cells, *Proc. Natl. Acad. Sci. USA* 101:9381-9386 (2004).

Miller and Abrams, "Angiogenic inhibitors and stimulators gaining ground," *Gen. Engin. News* 18:1 (1998).

Pasqualini and Ruoslahti, "Organ targeting in vivo using phage display peptide libraries," *Nature* 380:364-366 (1996).

Pasqualini et al., "Aminopeptidase N is a receptor for tumor-homing peptides and a target for inhibiting angiogenesis," *Cancer Res.* 60:722-727 (2000).

Polentarutti et al., "Unique pattern of expression and inhibition of IL-1 signaling by the IL-1 receptor family member TIR8/SIGIRR," *Eur. Cytokine Netw.* 14:211-218 (2003).

Rajotte and Ruoslahti, Membrane dipeptidase is the receptor for a lung-targeting peptide identified by in vivo phage display, *J. Biol. Chem.* 274:11593-11598 (1999).

Rasmussen et al, Angiogenic gene therapy strategies for the treatment of cardiovascular disease, *Curr Opin Mol Ther.* 4(5):476-481 (2002).

Ruoslahti and Rajotte, "An address system in the vasculature of normal tissues and tumors," *Annu. Rev. Immunol.* 18:813-827 (2000).

Ruoslahti, "Specialization of tumour vasculature," *Nat. Rev. Cancer* 2:83-90 (2002).

Sprinzak et al., "How reliable are experimental protein-protein interaction data?," *J. Mol. Biol.* 327:919-923 (2003).

Sylven, "Angiogenic Gene Therapy," *Drugs of Today* 38(12):819-827 (2002).

Symes, "Focal Angiogenic Therapy for Myocardial Ischemia," *J Card Surg.* 15(4):283-290 (2000).

Thomassen et al., "Identification and characterization of SIGIRR, a molecule representing a novel subtype of the IL-1R superfamily," *Cytokine* 11:389-399 (1999).

(Continued)

*Primary Examiner*—Jon P Weber
*Assistant Examiner*—Abdel A Mohamed
(74) *Attorney, Agent, or Firm*—McDermott Will & Emery LLP

(57) ABSTRACT

The present invention provides a variety of isolated peptides and peptidomimetics, which can be useful, for example, in constructing the conjugates of the invention or, where the peptide itself has biological activity, in unconjugated form as a therapeutic for treating any of a variety of cardiovascular diseases as described below. Thus, the present invention provides an isolated peptide or peptidomimetic which has a length of less than 60 residues and includes the amino acid sequence CRPPR (SEQ ID NO: 1) or a peptidomimetic thereof. The invention further provides an isolated peptide or peptidomimetic which has a length of less than 60 residues and includes the amino acid sequence CARPAR (SEQ ID NO: 5) or a peptidomimetic thereof, or amino acid sequence CPKRPR (SEQ ID NO: 6) or a peptidomimetic thereof.

12 Claims, 15 Drawing Sheets
(3 of 15 Drawing Sheet(s) Filed in Color)

OTHER PUBLICATIONS

Van Ham et al., "Cloning and characterization of mCRIP2, a mouse LIM-only protein that interacts with PDZ domain IV of PTP-BL," *Genes Cells* 8:631-644 (2003).

Ware and Simons, "Angiogenesis in ischemic heart disease," *Nat. Med.* 3:158-164 (1997).

Yu et al., "The heart LIM protein gene (HIp), expressed in the developing and adult heart, defines a new tissue-specific LIM-only protein family," *Mech. Dev.* 116:187-192 (2002).

Genbank Accession No. 1006310A (protein p10, nucleic acid binding).

Genbank Accession No. AAK95062 (olfactory receptor [*Homo sapiens*]).

Genbank Accession No. AAR82819 (GH05851p [*Drosophila melanogaster*]).

Genbank Accession No. AK032458 (*Mus musculus* adult male olfactory brain cDNA, Riken full-length enriched library, clone: 6430550J24 product: similar to integral membrane protein CII-3 (fragment) [*Cricetulus griseus*], full insert sequence).

Genbank Accession No. AK032239 (*Mus musculus* adult male olfactory brain cDNA, Riken full-length enriched library, clone:6430509L22 product: hypothetical Glutamine-rich region containing protein, full insert sequence.

Genbank Accession No. BC010806 (*Mus musculus* expressed sequence AI256711, mRNA (cDNA clone MGC: 18899 Image: 4240425), complete cds).

Genbank Accession No. BC026536 (*Mus musculus* pyrroline-5-carboxylate reductase-like, mRNA (cDNA clone MGC: 35759 Image: 4987954), complete cds).

Genbank Accession No. BC026935 (*Mus musculus* bladder cancer associated protein homolog (human), mRNA (cDNA clone MGC: 25535 Image: 3597231), complete cds).

Genbank Accession No. CAA24701 (unnamed protein product [*Xenopus laevis*]).

Genbank Accession No. CAE62851 (hypothetical protein CBG07030 [*Caenorhabditis briggsae*]).

Genbank Accession No. NM_024223 (*Mus musculus* cysteine rich protein 2 (Crip2), mRNA).

Genbank Accession No. NP_510573 (protein kinase (XQ229) [*Caenorhabditiselegans*]).

Genbank Accession No. NP_793173 (tail protein D [*Pseudomonas syringae* pv. tomato str. DC3000]).

Genbank Accession No. NP¯823828 (putative regulatory protein [*Streptomyces avermitilis* MA-4680]).

Genbank Accession No. NP_942914 (putative invertase [*Ralstonia eutropha*]).

Genbank Accession No. NP_955575 (virion core structural peptide p10 [*Feline leukemia* virus]).

Genbank Accession No. O98461 (chloroplast 30S ribosomal protein S11).

Genbank Accession No. Q91DH7 (large delta antigen (p27) (HDAg-L) [contains: small delta antigen (p24) (HDAg-S)]).

Genbank Accession No. S58016 (probable olfactory receptor tpcr24—human (fragment)).

Genbank Accession No. ZP_00055984 (hypothetical protein Magn0210672 [*Magnetospirillum magnetotacticum*]).

Genbank Accession No. ZP_00150197 (COG0178: excinuclease ATPase subunit [*Dechloromonas aromatica* RCB]).

Genbank Accession No. ZP_00170399 (COG0129: dihydroxyacid dehydratase/phosphogluconate dehydratase [*Ralstonia eutropha* JMP134]).

Genbank Accession No. ZP_00171368 (COG0642: signal transduction histidine kinase [*Ralstonia eutropha* JMP134]).

Genbank Accession No. ZP_00307071 (COG1249: pyruvate/2-oxoglutarate dehydrogenase complex, dihydrolipoamide dehydrogenase (E3) component, and related enzymes [*Ferroplasma acidarmanus*]).

* cited by examiner

A.

```
   1 cggacgcgtg ggtccgcgga ccgaccgagc gcaccgacca tggcctccaa gtgtcccaag
  61 tgtgacaaga ccgtatactt cgctgagaag gtgagctccc tgggcaagga ctggcacaag
 121 ttctgtctca agtgtgagcg ctgcaacaag acactgaccc ccggcggcca tgctgagcat
 181 gatgggaagc ccttctgcca caagccctgc tatgccacac tgtttggacc caaaggcgtg
 241 aacatcgggg gcgctggctc ctacatctac gagaagcctc agaccgaggc ccctcaggtc
 301 actggcccca tcgaggtccc tgtggtgaga actgaggagc gaaagaccag cggccccccc
 361 aagggtccca gcaaagcctc tagtgtcacc acattcactg ggagcccaa catgtgtcct
 421 cgatgcaaca agagagtgta cttcgctgag aaggtgacct ctctgggcaa ggactggcac
 481 cggccctgcc tgcgctgtga gcgctgctcc aagaccctga ccccaggcgg gcatgctgag
 541 cacgatggcc agccctactg ccacaagcct tgctatggaa tactctttgg acccaaagga
 601 gtgaatactg gtgctgtggg cagctatatc tacgacaagg acccggaagg cacagttcag
 661 ccctagatct gcagatgctg tcctcggggt ccccctgttt gacccggagg caaagtggcc
 721 tgttgcctag tcctgcctca gcgtgtctcg cctgcaaatc cgggacctaa gtggtggagg
 781 agaaagcctg gatagtccca gagcttcagc cccctttgtc accttggcgt gtcccgtgct
 841 gcccaccgtt tacttcctgt ctgtgtgcct ccgtagcccc atgggtcctg tgttcctgtg
 901 tccctgatag ctctccaagg tgactgtcct atgatatatc cctttgccca cacctgccca
 961 ccagtattat ttatgctctg cttgccggtg atggccgtga gctcacagca ttcccagggt
1021 gatggctggt gcccttgcga ggagccctct gctggttcca cactactccc tacctaccct
1081 cacatggttc atggctatgg agacttttgc tgtcaataaa tagtttggtt tgaggattgc
1141 aaaaaaaaaa aaaaaaaaaa aaaaaaaaaa aaaa
```

SEQ ID NO:24

B.

```
                    MASKCPKCDKTVYFAEKVSSLGKDWHKFCLKCERCNKTLTPGGH
AEHDGKPFCHKPCYATLFGPKGVNIGGAGSYIYEKPQTEAPQVTGPIEVPVVRTEERK
TSGPPKGPSKASSVTTFTGEPNMCPRCNKRVYFAEKVTSLGKDWHRPCLRCERCSKTL
TPGGHAEHDGQPYCHKPCYGILFGPKGVNTGAVGSYIYDKDPEGTVQP
```

SEQ ID NO:25

```
   1 ccagctcaga gcaggatggc ggcgacaatg tctgaacctc ggcgtgtggg cttcgtgggt
  61 gcaggccgca tggcggaggc cattgcccga ggcctcatcc aagcaggcaa agtagaagct
 121 aaacaagtgc tggccagtgc accaacggac aacaacctct gccacttcag ggctctgggt
 181 tgccagacta ctcactccaa ccatgaggtg ctgcaaaact gcccacttgt catctttgcc
 241 accaaacccc aagtcctgcc aactgtcctg gcggaagtgg cccccatagt caccactgag
 301 cacatcatcg tatctgtggc tgctgggatc tctctgagca caatggaggg gctgttaccc
 361 ccgaacacac gagtattgcg agtctctccc aatctaccct gcgttgtcca ggaggggccc
 421 atggtgatgg cccggggcca ccatgctggg aacgatgacg cagagctcct acagaacttg
 481 ctggaagcct gtgggcagtg catagaggtt cccgagtcct acgtagatat ccacaccggt
 541 ctcagtggca gtggtgtggc ctttgtgtgt acattttcag aggccctggc tgaaggtgcc
 601 atcaaaatgg gcatgcccag tggcctggcc caccgcattg ctgctcagac cctgctgggg
 661 acagccaaga tgctgcagca ggaagggaag cacccagccc agcttcggac agatgtgctc
 721 acaccagctg gaaccaccat ccatgggttg catgccctag agcggggcgg ttttcgagcg
 781 gctaccatga gtgcggtgga agcagctacc tgccgggcta aggagctcag caagaagtaa
 841 ggcaggcctc agatgagact acgggctcct tgcccagctg cagcctctgt ggtgagaata
 901 gccctggacg ggagatgtag tgggcagtcc tctaagtgga atggctaatt tatccaagaa
 961 gcggtgacta cttgtaagat gctatcaaga cggggttgcc ttgactgtga cattcagtca
1021 aggaagaatc gcttgcccct tacctgagat tccagatcct cccttctgca cctcctggcc
1081 agttgcagtt gtgtcctcat ggtcacagga gctggtagaa tatgtctcct gtggaggtgg
1141 tagacatcat cctccatgct ggcgtgagac gtctttggtt gtggctgctt tggatcacc
1201 cacactccgt aagcagcgcc ccgtccatat tctctaagcc caataaactc attggttctc
1261 taaaaaaaaa aaaaaa
```

SEQ ID NO:26

B.

```
MAATMSEPRRVGFVGAGRMAEAIARGLIQAGKVEAKQVLASAPT
DNNLCHFRALGCQTTHSNHEVLQNCPLVIFATKPQVLPTVLAEVAPIVTTEHIIVSVA
AGISLSTMEGLLPPNTRVLRVSPNLPCVVQEGAMVMARGHHAGNDDAELLQNLLEACG
QCIEVPESYVDIHTGLSGSGVAFVCTFSEALAEGAIKMGMPSGLAHRIAAQTLLGTAK
MLQQEGKHPAQLRTDVLTPAGTTIHGLHALERGGFRAATMSAVEAATCRAKELSKK
```

SEQ ID NO:27

```
   1 ctacagaaag gagcccttct cagcctgcag tggaccccat ctgctcggtt aaggagccac
  61 ggcggtgcca gggagggaaa ccagcgtttg gcctgccgtg aagaggtccc agaagagcca
 121 tggcaggtgt ctgtgacatg gcccctaatt tcctttcccc atctgaagac caggccttgg
 181 gtcttgccct tggcagagaa gttgctttga attgcacagc ttgggtgttc tctaggcccc
 241 agtgtcccca gccatcagtg cagtggctga aagatggtct ggcattgggc aatggaagcc
 301 acttcagcct ccatgaggac ttctgggtca gcgccaactt ctcagagatt gtgtccagtg
 361 tcctggtgct caacttgacc aatgcagagg actatggaac cttcacctgt tctgtctgga
 421 atgtcagctc ccattccttc actctttggc gagctggccc tgctggccat gtggctgcag
 481 tactggcttc cctcctggtc ctggtggttc tgctgctggt ggccctgctc tatgttaagt
 541 gtcggctgaa catgctgctt tggtaccaag acacttacgg ggaggtggag atgaacgatg
 601 ggaagttata cgatgcctac gtgtcctata gcgactgccc agaggaccgc aaatttgtaa
 661 attttattct gaagcctcag ttggagcggc gtcggggata caaactcttc ctagaggacc
 721 gcgacctctt gcctcgcgcg gagccctctg ccgacctttt ggtgaacctg agtcgctgtc
 781 ggcgtctcat cgtggttctt tcagatgcct tcctaagccg gccctggtgt agccagagct
 841 tccgggaggg actgtgccgc ctactggagc tcacccgcag acctatcttc atcacctttg
 901 agggccagag gcgtgagccc atacaccctg ctctccggct cctgcgccag caccgccacc
 961 tcgtgaccct ggtgctttgg aagcctggct ccgtgactcc ttcctctgat tttggaaag
1021 agctacagct agcactgcca cggaaggtgc agtacaggcc ggtggaggga gaccctcaaa
1081 cccgacttca ggatgacaaa gatcccatgc taatcgtgag aggacgtgct gcccagggcc
1141 ggggcatgga gtcagagctg gatccagacc ctgagggaga cctgggtgtc cgtggacctg
1201 tctttgggga gccaccaact ccactgcagg aaaccaggat ctgcatagga gagagccacg
1261 gcagtgaaat ggatgtctct gacctcggct ctcgaaacta cagtgcacgg acagacttct
1321 actgcctcgt gtctgaggat gatgtgtagc ccatatccca gcagcccaga ccatgagatc
1381 acggtggcag cttccagggt agaggcagca ggcactcctt cctaggatca caacccttgc
1441 ctctatccct gggcccctca ggaaaggagt gtggccccag ggtgtcacaa aataaaatcc
1501 tgttggttcc tgaaaaaaaa aaaaaaaaaa aaaaaaaaaa aaaaaaaaaa aaaaaaaaaa
1561 aaaaaaaa
```

SEQ ID NO:28

B.

```
MAGVCDMAPNFLSPSEDQALGLALGREVALNCTAWVFSRPQCPQ
PSVQWLKDGLALGNGSHFSLHEDFWVSANFSEIVSSVLVLNLTNAEDYGTFTCSVWNV
SSHSFTLWRAGPAGHVAAVLASLLVLVVLLLVALLYVKCRLNMLLWYQDTYGEVEMND
GKLYDAYVSYSDCPEDRKFVNFILKPQLERRRGYKLFLEDRDLLPRAEPSADLLVNLS
RCRRLIVVLSDAFLSRPWCSQSFREGLCRLLELTRRPIFITFEGQRREPIHPALRLLR
QHRHLVTLVLWKPGSVTPSSDFWKELQLALPRKVQYRPVEGDPQTRLQDDKDPMLIVR
GRAAQGRGMESELDPDPEGDLGVRGPVFGEPPTPLQETRICIGESHGSEMDVSDLGSR
NYSARTDFYCLVSEDDV
```

SEQ ID NO:29

Figure 10

```
   1 aaggcccccct cctctggacc ctcctctccg gccagagtca ataccacacc tagatgacat
  61 caccctgcca cccataggag ctcaggcttt tgcccatctg agggcgtgct ggccaggtgc
 121 cggtggccac cttgtgcgca tgctcggtag ctgcacagtg cgcatgctcg gtagctgcac
 181 aatgcatctt aggcagcgtc ctctctgacc cttgtgcaag accatcctgg tattggcgct
 241 taggaaggtg taagcagcag agtctggtgt ccacaaaaag aaaaaaaaat gttttagtat
 301 agtgagaagc aaaagagaaa caactccaat tgtccttgag cgacgaactt ccatggcaga
 361 actttaggtc agtcacaaac agctccgttt tgaatacacg aaaccctcct tgtaccaacc
 421 gccgcatgtg tatatccaga tgtgtgggta tacaactgtg gcgattccga attgcatttt
 481 tttataacgc gatacgctga catattttag tgaaggtcag cagttttcta acttgtgcct
 541 aagaattatt gggaaatgaa aatgcatttc tatctagttt cctggaaata tttctaccca
 601 aaatagagaa gaaaagaagg aaagaaagaa agaaaaaaaa agaaaaggta gaagcatgcc
 661 tatctgccac cgagtgatcc cctgcttaac ctaaacacca gcgatttgta gatggtaact
 721 gcctttggaa aaatagcttc ttagtccaac gtgactgggg tcactggtac cccactgcag
 781 gatttaatta tgacttctcc tatcccaagg aggtgaaatg tagcggggtg ggggtggggg
 841 gaactgagga gtcatatagt ctggccaatg ttttcctcct tagtgattca ttatcttgaa
 901 aacaccagtt ttgctccgcc ccccccccca atggcatctt ggaatccatc atcaagctag
 961 tattgcgtcc tcaggaaaac atgggagcat gtggcttttg cagcgaggat gagcctgaac
1021 ttggagaaga tcaagaccat gcatggctca tcttcatgac agaggagtct ggtagggcca
1081 ccatggctcc catcacggcc tctcataggc aacacccaca ttttcagttt ggttctatga
1141 ctcgacccca tcaccacaca acaagatggc tcaggggttc cagtcaaggc ttccagaaac
1201 cagcctttct ctcttgggga aaggagggaa gccagttcta aaggtgctag atcatgtccc
1261 ttctgctgga gggtcaccag ggctgcacct ggtagtagtc ccatcttagc cccagaaggc
1321 tctcccagac aagggaacgc agtgaaacgg ccagccggca tccatcagcc actggactgg
1381 cctttgactc taacacggta gaaattagac cacgaaaggt attcatgtag tgctatggaa
1441 gattagaggc atgatccaca aaggagaagt agttttaaca gtcaacacag tgccgataac
1501 gatacctttg tttcctgtat atgacaagag acccttcact ttctaagcat gggcctgcct
1561 gtctttgagc atgcccaaga tgacaagagc aatggagcca agcagaaatg gcctgggcat
1621 ggtgacagct tctccaagga tacacataac tgactcagag gcaaatgtgg tctgtatccc
1681 ttctatggct ctgagttggg cgtccttggc ctcggatgca tctgactgta gccagcttcc
1741 atgggtcttg cccattctgg agacacacac ggtagataca cagagaagaa acaggtcttt
1801 tccctttggc tctgcatgat actgggatac tgagctgggc attccataat agtagcccat
1861 gccatgtcag ttacacacac acacacacaa atatttattc ttttagcagg cacaacctgc
1921 aggtataagt ttggttggcc acttagctct ccaagttagg acccgcctcc acagctgtac
1981 ctgctgaggg caggtactca gcaatacaga gttcgatgtg attatagaat gtggtgcagt
2041 atgttaggct gttgtggtca aagtggtagc aatgttagat ctatgtaccc tcattaggtg
2101 gactagagct ttgccctaat cagcctcgac cctgggcact tgaataaatc tccccatggc
2161 cctggcttcg tttctccatc acagacaccc atcacatatg gtaccccacc tgaattaagt
2221 tctgagatcc aggtggccag agctgctatg attcctctgc ctccatgctg ctatgatccg
2281 gacctctcgg catggaaacc cgagtctgtc tcccttccca ggctggggaa ctgcgccctc
2341 ccctcctgcc acagacagac ctgccaaaca gctctgttct tcatggagtc aggaggtcct
2401 gctggcctgc agcaactcag ttgccttggg ctgggactgc attcttgtga tgtctggatg
2461 ggtttggggc tggaggtcag gtactctggg attagctgaa gggggcacag tgttctttgt
2521 cctgcccctc cggttaactg tgctccatat ttgtgttgaa ctctaaaagc atattaaagt
2581 gaacctgagg g
```

SEQ ID NO:30

```
   1 tgatttccgt ccaggccgga actcaagatg gctgcgttct tgctgagaca tgtcagccgt
  61 cactgcctcc gagcccacct gaatgctcag ctttgtatca gaaatgctgc tcctttggga
 121 accacagcta aggaggagat ggagcggttc tggaagaaga acacgagttc aaaccgtcct
 181 ctgtctcccc atttgactat ctacaaatgg tctcttccta tggcactgtc cgtttgccac
 241 cgaggctctg gaatagcctt gagtggaggg gtctctcttt ttggcctgtc ggcactgctg
 301 cttcctggga actttgagtc atatttgatg tttgtgaagt ccctgtgttt ggggccaaca
 361 ctgatctact cggctaagtt tgtgcttgtc ttcccgctca tgtaccactc actgaatggg
 421 atccgacact tgctatggga cctaggaaaa ggcctggcaa taccccaggt ctggctgtct
 481 ggagtggcgg tcgtggttct tgctgtgttg tcctctggcg ggctggccgc cctgtgaaga
 541 gctggagttc ccagcacccc tgtacatcat caaactgatt tatattcctg tttatcacta
 601 tccccacccc tcccccccag cctcccaggt tctcctgatt tgtttagatg ccacatgctt
 661 tcaatcccct tggagtgcag tagagcggct taaagacctg ttgtagtaag aaagggtcat
 721 cctccctggg cctgggagcc cttgctccgg ttccacattt gactgatttg tgctgagggt
 781 cagctttccg ctgctttctg ctgagacagt ggaaacaatg ccagttctgt gaccgccccg
 841 agtgccactg cctgtgggct gctggcttaa aggacacttc tgtccattgg tcagcttagg
 901 gcctttagca cccacaccgc gtgactgaga ggagagaggt ggaggaggag ggattgtcct
 961 gctcagctag agggagataa agagcagcct gggagcttgg agctcgagcc tgggaacaga
1021 tacagctttt gatgtatgag gaagatcaaa aaaaattgta ttaagtttct gttctgtttt
1081 tcatttctag gaaaatacac ctttaatgtc atattttcta atctaaattc ttgtaccatc
1141 ttctttggaa acgattaaag tactactcat tttatgcttg actctttgga atctagtgac
1201 aggtgggtag aaagggtcta atctctgccc ctccctttgg atcttggaca tttacaccct
1261 ccagtatgga gggaaatagt ttgcccaaca actaccactg cgaaaaatga ggtaatcaca
1321 accaagtagt ggagagattt tggtcaagga aagaacataa gaagtcagct aagcatgcgg
1381 ggagcttttg gggtgttgta gggcccaggc ctgtggatgg ccagcttggt acttaagcag
1441 accatttggt tatggacacc tagcaccagt ggaggtggag gctaagggct aaatagattt
1501 gggggaggt aggggaagta gaagagaatt ttttaaaagc agggcaggat tggaggcatc
1561 agagttcttg aagatggata tacagtggga aacgttgctt ctttacccct actgaggccc
1621 tggatcctta ccaagggtgc tttgtttgtg gtgctagggg tcaaagccag gtccttgtgc
1681 gtgttagcaa gcgctgtacc actacaccag ttccctagcc aggagtgcta ttttgataga
1741 tttttgccaa ctctggagta aaagctccat cttgggacta gagatttggt tccatgatca
1801 tatgcccaag gcctgtggtt cagtccccac caccaagaaa aacactactc caagagattg
1861 gtcagagcac tggattgggg agtgattgct gggtggcagt tagacaggaa gacagcatga
1921 actcaaatcc gtggcagcag aggtgggctg ggcccaggtt aggttgggtt gagggctgtt
1981 tcattagtct cttgaaatct gtagaaaggg attcaccatt tatccccaaa tggcctggaa
2041 gtcttaccca gactaccttc cagttggtgt gatcttgctt ctgcctcccg ggtgcatgtt
2101 accaccaccc tcagccctca gcctattcct gatcccaagt agtgtttggc ctcaagcaac
2161 gatcactacc actctcctct agacaggccc cgggaggtct ggtggtgcca ggaattcagc
2221 ccagggtccc atccgtgcta ggcaagcact gaacctgagt caggccttgc caagtaccca
2281 gcccagccca gacaggcctc gaactgacca cccatctgct tcagcctccc aagtagctgg
2341 aattacagga ccatgctacc acatgcgact gctgggatgt cctgtagatt tcatccagcg
2401 tcaatcaggt tgtccttaga gtagagtcag agttcatggg gaaacacttt tgctttagac
2461 ttggcaaggg cattaaattc aacaaccagt gccagaaaga tgtatagaca gggcaaaggt
2521 caacatattg gcaggctggg aaattaatgt ggacattttt actttttttt ttgatggctt
2581 cttaaccagt gattggaggg aagtaggtcg cctggcttct ttatttttct ctttgtaagc
2641 cggtctgtag gcttatatat atatatatat atattttttt ttaagattta tttatttatt
2701 atatgtaagt acactatagt tgtcttcaga taccccagaa gagggcatca gatctcatta
2761 cagatggttg tgaaccacca tgttgttgtt aggatttgaa ctcaggacct tcagaagagc
2821 agacagtgct cttaactgct gagccatctc tccagccctg gcttatatct tttaaaacct
2881 agtttaataa gggcatttaa aggctttaac ctccctttct aacctaccac ccagcagagg
2941 tagtgggaag gaaaggttag taaccagaca tttttacttc actggtctgt caagataact
3001 cagcgggtgc aggctctggc cccaagcct gaggacgcga gtttgatccc aggatccacg
3061 tgtcagaagg atccaccctc cgtaagctgt ctctggcttc cacgtgcttg aggcacacct
3121 ccatgcatac gtaaagtcaa tgaatgcgtg taataaaggc ttgtgtgctc t
```

SEQ ID NO:32

MAAFLLRHVSRHCLRAHLNAQLCIRNAAPLGTTAKEEMERFWKK
NTSSNRPLSPHLTIYKWSLPMALSVCHRGSGIALSGGVSLFGLSALLLPGNFESYLMF
VKSLCLGPTLIYSAKFVLVFPLMYHSLNGIRHLLWDLGKGLAIPQVWLSGVAVVVLAV
LSSGGLAAL

SEQ ID NO:33

```
   1 gttggtggcg agctaaggtg gaggcaagca gcggcggcga cggcgacagt ggcggcagtg
  61 ccatggtggg gctcgcagga tccctgctgc cttggtgatc ccgggctgac agccagagag
 121 cacagcggct cagctcctgg agagagagtc gaagaaagcg aagggcagcc acctgtgcct
 181 gctggctccc attaggtcgg ttcctgcagc ggtgcctggc agccttggtg aaggccctgc
 241 ccggcagaga tcatgtattg cctccagtgg ctgctgcccg tcctcctcat ccccaagccc
 301 ctcaaccccg ctctgtggtt cagccactcc atgttcatgg gcttctacct gctcagcttc
 361 ctcctggaac ggaaaccttg cacaatatgt gccttggttt tcctggcagc cctctttctc
 421 atctgctata gctgctgggg aaattgtttc ctgtaccact gctccgattc ccccacttccg
 481 gaatcagccc atgaccccgg tgttgtgggc acctaacgtc tgccgagata gcttgccaag
 541 gaagcagaag acgggagggg aggcattgac ataggtcata aagcattgga gtttcaaatc
 601 ccgcagtcct gcgggtacca cattcctaat ggagcctttt ggcctgtgat gttttatcct
 661 tacaatgtga ataatggcac tgatcggtgc ttctgttgta gagtcctgta gtcgtgggtg
 721 gtcttatggt tgtgtgttct gtcaccatct gggtcccggc tgacggattg gcccaccccc
 781 ttgctcattg atttggggaa tctataccct tgatatgacc tgtgtggata cagtgtagtc
 841 tcaatgtcac ctccataacc cttcctcgtc aagaccttcc tcgttccctc ctcgtcccct
 901 ttccccgttt tccccttggt tcacttccaa cccctttcct tttttgggga gcacctgtcc
 961 aagacagggc ttgtttttgc acttatctca aatttgaaga gattgctgat gcccgagagc
1021 ctcgcttttt catccttcgt tcccttttga gaaggtgaga cggaatcatg tctcaactgc
1081 tcgttgtctg cagacctcca gtatttcctc tgcctcattt ttaagaaaga agcgatgggg
1141 agacattgct ctttggcctg ggtatctggg ctcctgcctt ccagcccagc ctctctccct
1201 ttgctcttcc tcctgtctct ctcagctgac ctaaaggggc cacctcatgt ctccagtgca
1261 tgctcttcag gagggagatg tgcagtattc tcgtagaccc agtggtccct ggctgagtga
1321 atgagaaagt attacatttt tcatagcagc catgattccc ttggtaggtg tttggatatt
1381 tttgatgtgc cctgtatgta tgtgtgcact agtgtcagcg tgtatgtaca cacgtatgtg
1441 tgaatgtgtg ttgtgtgtgt gtttacatac caatacatgt gtatattcct tttgaagaag
1501 ctttattgaa tatgttctga ttttgaggtt tagtagtagt agctagctgt agtaggtcct
1561 gctgcagttt ttatttagca tggggattgc agagcgacca gcacagtgga ctccaaggtg
1621 gttcagacaa gacccagggg agcagtcgcc atcatcctcc caccaggagc ttcctcattg
1681 ctgcgcacgt agactgtaca ctatgaagaa aacacaggaa gaaagatttg gtgacttggt
1741 acttgtttgc ttttctctgc gcttcagaaa caagtgtttg caaatgagac tttctcctgg
1801 cccctaccca ctggggatca gcatggttgt tcttccagtc ggaaatgtac ccccctcctt
1861 tccccctctt gtgtgcaagt gggggggggg gcaggcatag gacagagctg gaagcaggct
1921 tctggggagt gggacttaga ggccacactt gtgaaacact cggactgctg ttgtaaagct
1981 tttatttctg gtgtgttcgt tccacagctg tttgaaatgt ttaataaagc tttataaact
2041 ttaaaaaaaa aaaaaaaaaa aaaaa
```

SEQ ID NO:34

B.

MYCLQWLLPVLLIPKPLNPALWFSHSMFMGFYLLSFLLERKPCT
ICALVFLAALFLICYSCWGNCFLYHCSDSPLPESAHDPGVVGT

SEQ ID NO:35

Figure 13

PEPTIDES THAT SELECTIVELY HOME TO HEART VASCULATURE AND RELATED CONJUGATES AND METHODS

This application claims the benefit of U.S. provisional application Ser. No. 60/714,515, filed Sep. 7, 2004, which was converted from U.S. application Ser. No. 10/936,027, filed Sep. 7, 2004, each of which the entire contents are incorporated herein by reference.

This invention was made with government support under CA 82713, CA 30199, NCI training grant T32 CA77109-05 and DOD training grant DAMD 17-02-0309. The government has certain rights in this invention.

BACKGROUND OF THE INVENTION

1. Field of the Invention

The present invention relates generally to the fields of molecular medicine and drug and gene delivery and, more specifically, to cardiovascular disease and novel compositions for treating cardiovascular disease.

2. Background Information

Atherosclerosis and its sequelae constitute the most common and important cause of disease and death in the western world, accounting for 50% of all deaths in the west. As described further below, atherosclerosis is a disorder which results from the thickening and inelasticity of vessel walls or arteries as a consequence of atheroma.

In normal hearts, vessel walls are composed of an endothelial cell lining that is tightly juxtaposed to a medial layer of vascular smooth muscle cells with an over layer of connective tissue. The endothelial cell lining is ideally situated at the interface between the blood and the vessel wall to transduce signals, with endothelial cells controlling the homeostatic balance of the vessel through the production of factors regulating processes such as vessel tone, coagulation state, cell growth, cell death, and leukocyte trafficking. Vascular smooth muscle cells maintain the contractile tone of the blood vessel in response to vasoactive agents, and release cytokines and other growth factors. In conjunction with fibroblasts, the smooth muscle cells produce extracellular matrix proteins and proteases that determine vessel structure. Occlusive vascular disease, the most common form of which is atherosclerosis, is characterized by an abnormal accumulation of lipid, inflammatory cells, vascular smooth muscle cells and extracellular matrix proteins within the intimal space between the endothelial lining and the medial layer (plaque formation).

Therapies for atherosclerosis generally prevent, arrest or reverse the process of plaque formation or stimulate the formation of new blood vessels. It is rare, however, that a drug or other agent for treatment of atherosclerosis targets only coronary vessels. More commonly, systemic administration results in undesirable side effects due, for example, to generalized toxic effects throughout the entire body. For example, vascular endothelial growth factor (VEGF), a key regulator of angiogenesis that stimulates endothelial cell proliferation, promotes the formation of new vessels, thereby increasing blood flow to ischemic tissue and relieving vascular disease. However, VEGF also can promote nonspecific mitogenesis and potentiate angiogenesis-driven diseases such as diabetic retinopathy, and certain tumors. Similarly, systemic administration of the angiogenic stimulator fibroblast growth factor can cause severe side effects due to its lack of specificity for cardiac tissue. Unfortunately, such side effects, which include repetitive episodes of hypertension, limit the utility of existing pro-angiogenic therapies for treatment of atherosclerosis.

As the cells which make up the internal lining of blood vessels, endothelial cells are the first cell type encountered by a circulating drug or other substance. Endothelial cells therefore provide a target for selectively directing a therapeutic substance to cardiac tissue. Such selective targeting of a drug or other therapeutic substance to heart vasculature would reduce or eliminate the risk of unwanted side effects such as systemic toxicity or malignant transformation. Selective targeting of a therapeutic substance to heart vasculature also would effect a high local concentration of the substance, thereby reducing the dosage required for effective treatment.

Thus, a need exists to identify molecules that selectively bind to heart vasculature in vivo. Such molecules would be particularly useful for selectively targeting therapeutic agents to the heart for treatment of cardiopathies and cardiovascular diseases such as atherosclerosis. The present invention satisfies this need and provides related advantages as well.

SUMMARY OF THE INVENTION

The present invention provides a variety of isolated peptides and peptidomimetics, which can be useful, for example, in constructing the conjugates of the invention or, where the peptide itself has biological activity, in unconjugated form as a therapeutic for treating any of a variety of cardiovascular diseases as described below. Thus, the present invention provides an isolated peptide or peptidomimetic which has a length of less than 60 residues and includes the amino acid sequence CRPPR (SEQ ID NO: 1) or a peptidomimetic thereof. The invention further provides an isolated peptide or peptidomimetic which has a length of less than 60 residues and includes the amino acid sequence CARPAR (SEQ ID NO: 5) or a peptidomimetic thereof, or amino acid sequence CPKRPR (SEQ ID NO: 6) or a peptidomimetic thereof.

The invention further provides an isolated peptide or peptidomimetic which includes the amino acid sequence GRKSKTV (SEQ ID NO: 14) or a peptidomimetic thereof. In one embodiment, the invention provides an isolated peptide or peptidomimetic which includes the amino acid sequence CXGRKSKTVZC (SEQ ID NO: 15) or a peptidomimetic thereof, where X=0 to 20 independently selected residues and Z=0 to 20 independently selected residues.

The present invention additionally provides an isolated peptide or peptidomimetic which has a length of less than 150 residues and includes the amino acid sequence CARPAR (SEQ ID NO: 5) or a peptidomimetic thereof.

Also provided herein is an isolated peptide or peptidomimetic which has a length of less than 50 residues and includes the amino acid sequence CPKRPR (SEQ ID NO: 6) or a peptidomimetic thereof.

The present invention additionally provides an isolated peptide or peptidomimetic which has a length of less than 400 residues and includes the amino acid sequence CKRAVR (SEQ ID NO: 7) or a peptidomimetic thereof.

Further provided by the invention is an isolated peptide or peptidomimetic which includes the amino acid sequence RNSWKPN (SEQ ID NO: 16) or a peptidomimetic thereof. In one embodiment, the invention provides an isolated peptide or peptidomimetic which includes the amino acid sequence CXRNSWKPNZC (SEQ ID NO: 17) or a peptidomimetic thereof, where X=0 to 20 independently selected residues and Z=0 to 20 independently selected residues.

Further provided herein is an isolated peptide or peptidomimetic which includes the amino acid sequence RGSSS (SEQ ID NO: 9) or a peptidomimetic thereof.

The present invention also provides an isolated peptide or peptidomimetic which has a length of less than 400 residues and includes the amino acid sequence RSTRANP (SEQ ID NO: 18) or a peptidomimetic thereof. In one embodiment, an isolated peptide or peptidomimetic of the invention includes the amino acid sequence CXRSTRANPZC (SEQ ID NO: 19) or a peptidomimetic thereof, where X=0 to 20 independently selected residues and Z=0 to 20 independently selected residues.

The present invention additionally provides an isolated peptide or peptidomimetic which has a length of less than 400 residues and includes the amino acid sequence PKTRRVP (SEQ ID NO: 20) or a peptidomimetic thereof. In one embodiment, an isolated peptide or peptidomimetic includes the amino acid sequence CXPKTRRVPZC (SEQ ID NO: 21) or a peptidomimetic thereof, where X=0 to 20 independently selected residues and Z=0 to 20 independently selected residues.

Further provided herein is an isolated peptide or peptidomimetic which has a length of less than 400 residues and includes the amino acid sequence SGMARTK (SEQ ID NO: 22) or a peptidomimetic thereof. In one embodiment, the invention provides an isolated peptide or peptidomimetic which includes the amino acid sequence CXSGMARTKZC (SEQ ID NO: 23) or a peptidomimetic thereof, where X=0 to 20 independently selected residues and Z=0 to 20 independently selected residues.

Also provided herein is a method of isolating one or more homing molecules that selectively homes to heart vasculature by contacting HLP/CRIP2, or a fragment thereof, with a library of molecules under conditions suitable for specific binding of a molecule to HLP/CRIP2; assaying for specific binding; and separating one or more HLP/CRIP2-binding molecules from the library, thereby isolating one or more homing molecules that selectively homes to heart vasculature and specifically binds HLP/CRIP2.

Further provided by the present invention is a method of isolating one or more homing molecules that selectively homes to heart vasculature by contacting receptor clone 9, or a fragment thereof, with a library of molecules under conditions suitable for specific binding of a molecule to receptor clone 9; assaying for specific binding; and separating one or more receptor clone 9-binding molecules from the library, thereby isolating one or more homing molecules that selectively homes to heart vasculature and specifically binds receptor clone 9.

The present invention also provides a method of isolating one or more homing molecules that selectively homes to heart vasculature by contacting Sigirr/TIR8, or a fragment thereof, with a library of molecules under conditions suitable for specific binding of a molecule to Sigirr/TIR8; assaying for specific binding; and separating one or more Sigirr/TIR8-binding molecules from the library, thereby isolating one or more homing molecules that selectively homes to heart vasculature and specifically binds Sigirr/TIR8.

Further provided herein is a method of isolating one or more homing molecules that selectively homes to heart vasculature by contacting MpcII-3-related protein, or a fragment thereof, with a library of molecules under conditions suitable for specific binding of a molecule to MpcII-3-related protein; assaying for specific binding; and separating one or more MpcII-3-related protein-binding molecules from the library, thereby isolating one or more homing molecules that selectively homes to heart vasculature and specifically binds MpcII-3-related protein.

The present invention further provides a method of isolating one or more homing molecules that selectively homes to heart vasculature by contacting bc10, or a fragment thereof, with a library of molecules under conditions suitable for specific binding of a molecule to bc10; assaying for specific binding; and separating one or more bc10-binding molecules from the library, thereby isolating one or more homing molecules that selectively homes to heart vasculature and specifically binds bc10.

Also provided herein is a method of directing a moiety to heart vasculature in a subject by administering to the subject a conjugate which contains a moiety linked to an antibody, or antigen-binding fragment thereof, that selectively homes to heart vasculature and that specifically binds HLP/CRIP2 (SEQ ID NO: 25), thereby directing the moiety to heart vasculature.

The present invention further provides a method of directing a moiety to heart vasculature in a subject in which a conjugate is administered to a subject, the conjugating containing a moiety linked to an antibody, or antigen-binding fragment thereof, that selectively homes to heart vasculature and specifically binds SEQ ID NO:27, thereby directing the moiety to heart vasculature.

Also provided herein is a method of directing a moiety to heart vasculature in a subject by administering to the subject a conjugate which contains a moiety linked to an antibody, or antigen-binding fragment thereof, that selectively homes to heart vasculature and that specifically binds Sigirr/TIR8 (SEQ ID NO: 29), thereby directing the moiety to heart vasculature.

Further provided herein is a method of directing a moiety to heart vasculature in a subject by administering to the subject a conjugate which contains a moiety linked to an antibody, or antigen-binding fragment thereof, that selectively homes to heart vasculature and that specifically binds SEQ ID NO: 33, thereby directing the moiety to heart vasculature.

The present invention additionally provides a method of directing a moiety to heart vasculature in a subject by administering to the subject a conjugate which contains moiety linked to an antibody, or antigen-binding fragment thereof, that selectively homes to heart vasculature and that specifically binds bc10 (SEQ ID NO: 35), thereby directing the moiety to heart vasculature.

The present invention also provides a conjugate containing a therapeutic agent linked to a homing molecule that selectively homes to heart vasculature and specifically binds cysteine-rich protein 2 (HLP/CRIP2; SEQ ID NO: 25). Also provided herein is a method of directing a moiety to heart vasculature in a subject by administering to the subject a conjugate containing a moiety linked to a homing molecule that selectively homes to heart vasculature and specifically binds HLP/CRIP2 (SEQ ID NO: 25), thereby directing the moiety to heart vasculature.

The present invention further provides a conjugate containing a therapeutic agent linked to a homing molecule that selectively homes to heart vasculature and specifically binds receptor clone 9 (SEQ ID NO: 27). Also provided herein is a method of directing a moiety to heart vasculature in a subject by administering to the subject a conjugate containing a moiety linked to a homing molecule that selectively homes to heart vasculature and specifically binds receptor clone 9 (SEQ ID NO: 27), thereby directing the moiety to heart vasculature.

Further provided herein is a conjugate containing a therapeutic agent linked to a homing molecule that selectively homes to heart vasculature and specifically binds single Ig IL-2 receptor related protein (Sigirr/TIR8; SEQ ID NO: 29). Such a conjugate can be useful, for example, in a method of the invention for directing a moiety to heart vasculature in a subject by administering to the subject a conjugate which contains a moiety linked to a homing molecule that selectively homes to heart vasculature and specifically binds Sigirr/TIR8 (SEQ ID NO: 29), thereby directing the moiety to heart vasculature.

The present invention also provides a conjugate which contains a therapeutic agent linked to a homing molecule that selectively homes to heart vasculature and specifically binds SEQ ID NO: 33, a protein product having putative similarity to integral membrane protein CII-3 (MpcII-3). The invention additionally provides methods of directing a moiety to heart vasculature in a subject by administering to the subject a conjugate containing a moiety linked to a homing molecule that selectively homes to heart vasculature and specifically binds SEQ ID NO: 33, thereby directing the moiety to heart vasculature.

Also provided herein is a conjugate containing a therapeutic agent linked to a homing molecule that selectively homes to heart vasculature and specifically binds murine bladder cancer-associated protein homolog (bc10; SEQ ID NO: 35). The invention additionally provides methods of directing a moiety to heart vasculature in a subject by administering to the subject a conjugate containing a moiety linked to a homing molecule that selectively homes to heart vasculature and specifically binds bc10 (SEQ ID NO: 35), thereby directing the moiety to heart vasculature.

BRIEF DESCRIPTION OF THE DRAWINGS

The patent or application file contains at least one drawing executed in color. Copies of this patent or patent application publication with color drawings will be provided by the Office upon request and payment of the necessary fee.

FIG. 8 shows (A) the nucleotide (SEQ ID NO: 24) and (B) the amino acid (SEQ ID NO: 25) sequence of murine cysteine-rich protein 2 (HLP/CRIP2). Genbank accession NM_024223.

FIG. 9 shows (A) the nucleotide (SEQ ID NO: 26) and (B) the amino acid (SEQ ID NO: 27) sequence of the murine RIKEN EST identified as receptor clone 9. Genbank accession BC026536.

FIG. 10 shows (A) the nucleotide (SEQ ID NO: 28) and (B) the amino acid (SEQ ID NO: 29) sequence of murine single Ig IL-2 receptor related protein (Sigirr/TIR8). Genbank accession BC010806.

FIG. 11 shows the nucleotide sequence (SEQ ID NO: 30) of the murine olfactory cDNA which is a glutamine-rich region containing protein identified as receptor clone 27. Genbank accession AK032239.

FIG. 12 shows (A) the nucleotide (SEQ ID NO: 32) and (B) the amino acid (SEQ ID NO: 33) sequence of the murine polypeptide having putative similarity to integral membrane protein CII-3 (MpcII-3). Genbank accession AK032458.

FIG. 13 shows (A) the nucleotide (SEQ ID NO: 34) and (B) the amino acid (SEQ ID NO: 35) sequence of murine bladder cancer-associated protein homolog (bc10). Genbank accession BC026935.

DETAILED DESCRIPTION OF THE INVENTION

The present invention relates to the identification of molecules which home to heart vasculature with high selectivity and which can be useful in the form of conjugates for selectively targeting a systemically administered therapeutic or imaging agent to heart vasculature. Such selective targeting of a therapeutic agent increases the effective amount of the agent delivered to heart vasculature while reducing the likelihood that the agent will have an adverse effect on other organs. The present invention further relates to identification of cognate receptors for the homing molecules of the invention. As disclosed further below, these receptors are expressed on heart endothelium and can be useful for screening for optimizing the characteristics of peptides or other molecules that selectively home to heart vasculature.

Figure 1:
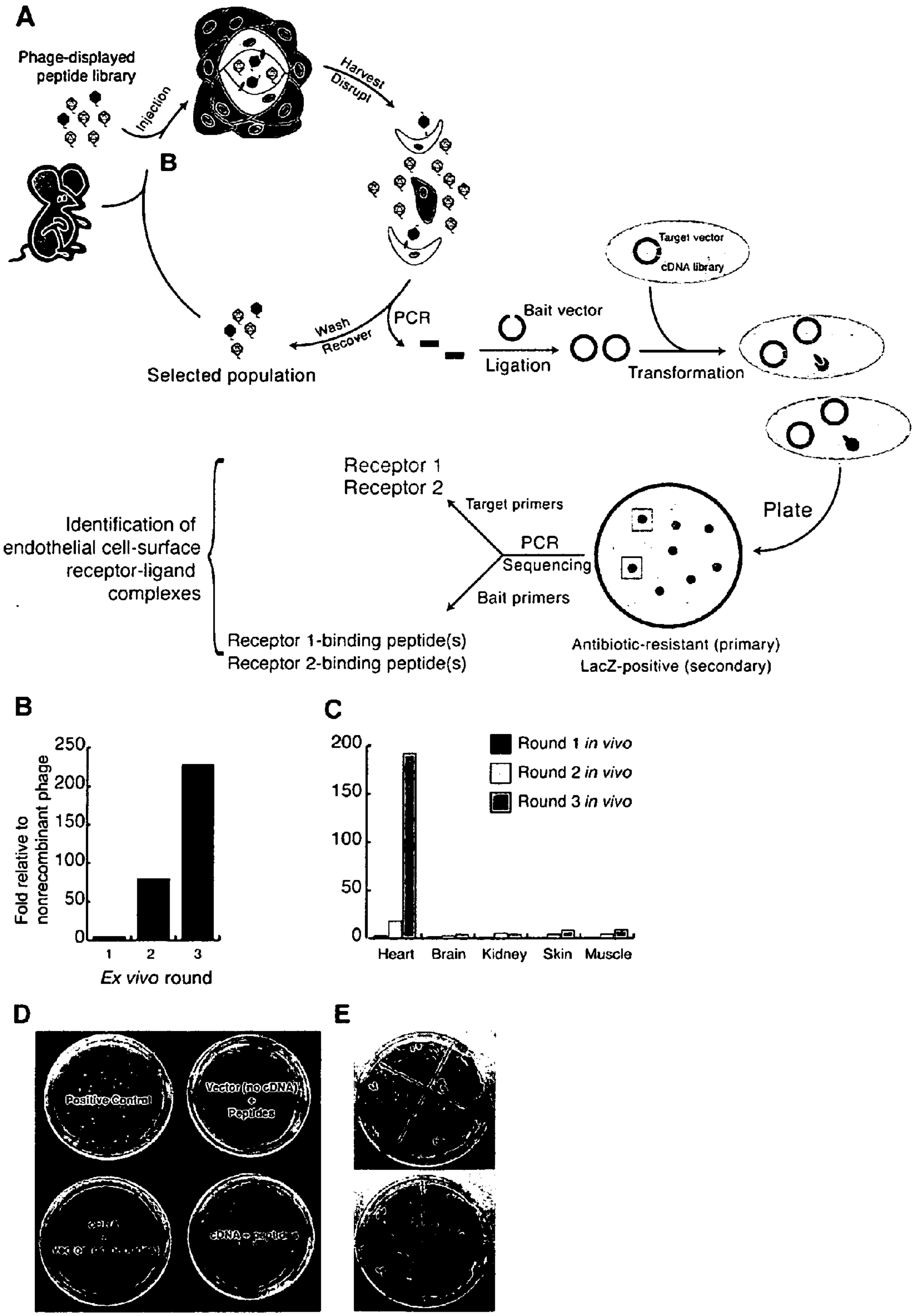
FIG. 1 shows identification of homing peptide/receptor pairs by ex vivo and in vivo phage display combined with bacterial two-hybrid analysis. (A) The principle of parallel homing peptide isolation and receptor identification. A phage-displayed peptide library is injected into a mouse and allowed to circulate; tissues are harvested and then disrupted into single cells with bound phage. Non-bound phage are washed away, and bound phage are recovered, grown up in bacteria, and the process is either repeated or the peptide-encoding inserts are amplified by PCR and shuttled into the bait vector component of the bacterial two-hybridization system. Once in the bacteria, the pool enriched for the ability to home to the selected tissue can interact with possible receptors, resulting in carbenicillin-resistance. Resistant clones are plated on X-gal-containing agar for a secondary screen; target and bait inserts are amplified and sequenced from carbenicillin-resistant, LacZ-expressing cells. (B) By the third round of ex vivo selection with anti-CD31 magnetic beads, the selected pool bound ex vivo heart cells about 230-fold more than non-recombinant T7 phage. (C) When further selected for homing to the heart in vivo, the ex vivo/in vivo selected pool accumulated in the heart vasculature about 190 times more than non-recombinant control phage. (D) Peptide-encoding inserts from the final pool were subcloned into the bait vector, and bacteria transformed with both peptide-bait vectors and a heart cDNA library in a target vector. Transformed bacteria were selected for growth on 500 μg/ml carbenicillin. (E) Some clones were also positive for the secondary marker, LacZ, as evidenced by the production of the blue color on plates containing X-gal.

As disclosed herein in Example I, a novel combination of ex vivo and in vivo phage selection and bacterial two-hybridization analysis was used to identify peptides that selectively home to heart vasculature, and to identify the endothelial molecules which serve as receptors for these peptides. Following ex vivo phage selection with murine heart cell suspensions and anti-CD31 magnetic beads, in vivo selection for homing to the heart was performed, resulting in a phage pool that homed to the heart with an increase of nearly 200-fold relative to non-recombinant phage (FIGS. 1A and 1B). Furthermore, as shown in FIG. 1C, the ex vivo/in vivo selected phage preferentially localized to the heart as compared to other tissues; the enrichment in heart was 20 to 50-fold greater than the accumulation in brain, kidney, skin and skeletal muscle.

Of 25 putative receptor clones identified by bacterial two-hybrid analysis with the pool of heart-homing phage, the majority were proteins abundantly expressed in cardiac muscle. As summarized in Table 1, the remaining six clones represented membrane or cell surface proteins and were putative receptors for the homing peptides. A first clone, denoted receptor clone 5, represents the carboxy-terminal 92 amino acids (residues 117 to 208) of heart LIM-protein (HLP), also designated cysteine-rich protein 2 (CRIP2). The full length murine HLP/CRIP2 nucleic acid and amino acid sequences are provided herein as SEQ ID NOS: 24 and 25, respectively (see Genbank accession NM_024223). Two-hybrid analysis yielded several potential heart-homing peptides which bound this receptor. When assayed individually, CRPPR (SEQ ID NO: 1)-displaying phage homed to the heart with more than 300 fold selectivity relative to non-recombinant phage (FIG. 2A), and CGRKSKTVC (SEQ ID NO: 2)-phage displayed about 50-fold selectivity in heart-homing relative to non-recombinant phage. These results indicate that peptides SEQ ID NO: 1 and SEQ ID NO: 2 are heart-homing peptides and further suggest that HLP/CRIP2 serves as the receptor for homing of these peptides.

As further disclosed herein, an unannotated RIKEN EST (receptor clone 9), was also identified as a membrane or cell surface-expressed protein which binds to one or more heart-homing peptides. The full-length murine nucleic acid and amino acid sequences of the RIKEN EST represented by receptor clone 9 are provided herein as SEQ ID NOS: 26 and 27, respectively (see Genbank accession BC026536). Of three distinct peptides identified through two-hybrid analysis, two peptides, CARPAR (SEQ ID NO: 5) and CPKRPR (SEQ ID NO: 6), exhibited selective homing to the heart when displayed on phage (FIG. 2B).

Figure 2:
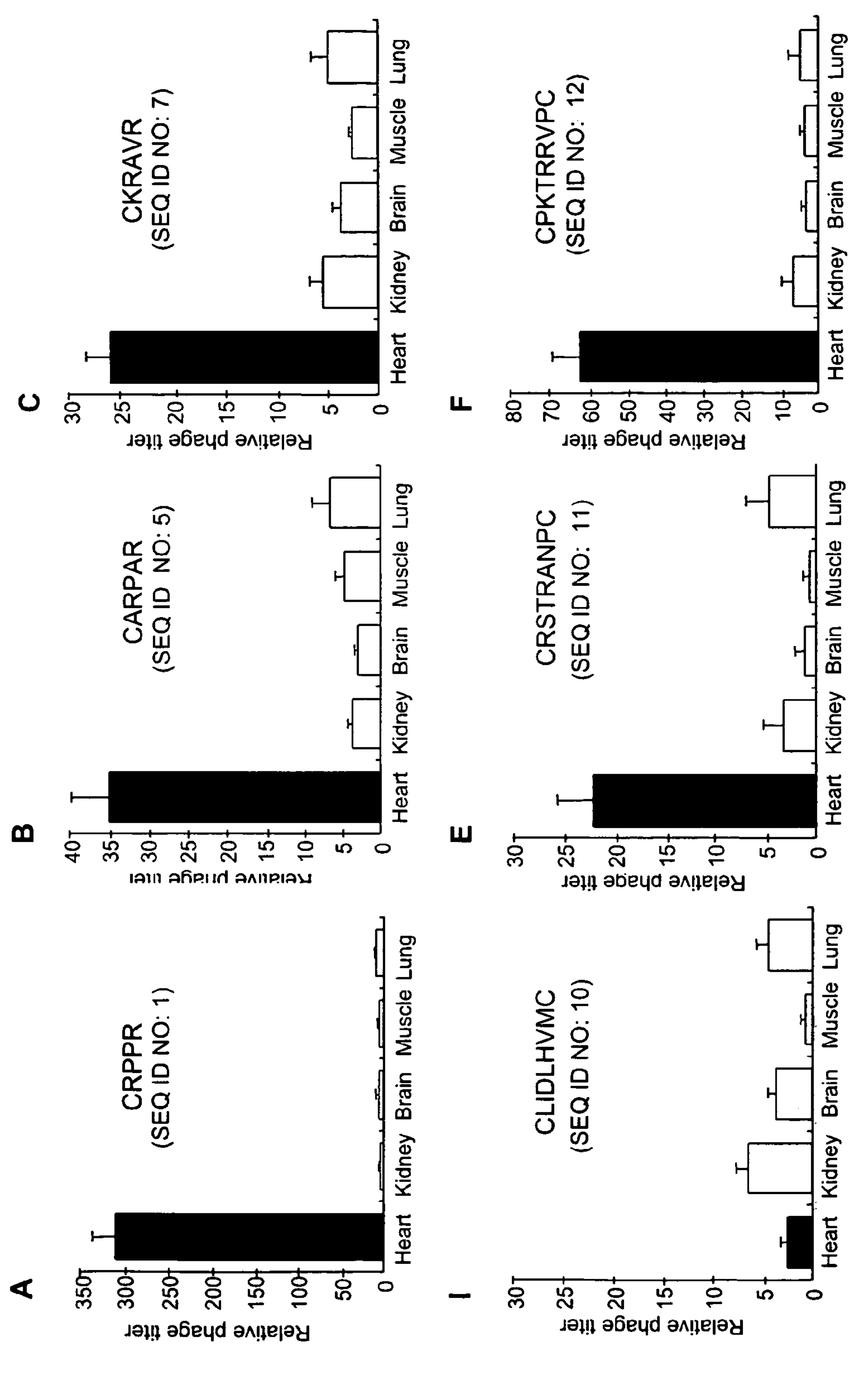
FIG. 2 shows that individual phage-displayed peptides home selectively to the heart. The indicated peptides identified from a combined screen for heart endothelial homing were reconstituted in T7 phage and individually administered by intravenous injection into mice. With the exception of SEQ ID NO: 10, phage displaying heart homing peptides significantly homed to the heart relative to non-recombinant phage; furthermore, homing was specific for the heart among the major organs tested. The highest specificity (over 300-fold) was recorded for the CRPPR (SEQ ID NO: 1)-displaying phage. (A) CRPPR (SEQ ID NO: 1) phage homing to heart, kidney, brain, muscle and lung. (B) CARPAR (SEQ ID NO: 5) phage homing to heart, kidney, brain, muscle and lung. (C) CKRAVR (SEQ ID NO: 7) phage homing to heart, kidney, brain, muscle and lung. (D) CLIDLHVMC (SEQ ID NO: 10) phage homing to heart, kidney, brain, muscle and lung. (E) CRSTRANPC (SEQ ID NO: 11) phage homing to heart, kidney, brain, muscle and lung. (F) CPKTRRVPC (SEQ ID NO: 12) phage homing to heart, kidney, brain, muscle and lung.

Results disclosed herein further identified the single Ig IL-1 receptor related protein designated Sigirr or TIR8 (receptor clone 15), as a receptor for heart homing peptides. The full length murine Sigirr/TIR8 nucleic acid and amino acid sequences are provided herein as SEQ ID NOS: 28 and 29, respectively (see Genbank accession BC010806). As summarized in Table 1, three peptides identified by binding Sigirr/TIR8 through two-hybrid analysis, CKRAVR (SEQ ID NO:

7), CRNSWKPNC (SEQ ID NO: 8), and RGSSS (SEQ ID NO: 9), showed 20 to 30-fold heart homing selectivity when displayed on phage and assayed in vivo (see Table 1 and FIG. 2C).

Also disclosed herein as a heart-homing receptor is receptor clone 36, which represents an unnamed protein product from the RIKEN Fantom set with putative similarity to integral membrane protein CII-3 (MpcII-3), a mitochondrial membrane protein which is part of the succinate dehydrogenase complex. The nucleic acid and amino acid sequences of this MpcII-3-related protein are provided herein as SEQ ID NOS: 32 and 33, respectively (see Genbank accession 26328274). Through two-hybrid analysis, the peptide CRSTRANPC (SEQ ID NO: 11) was identified as binding to this receptor; phage displaying SEQ ID NO: 11 homed to the heart with about 20-fold selectivity when assayed individually in vivo (Table 1 and FIG. 2E). Additional results disclosed herein indicate that murine bladder cancer-associated protein homolog 10 (bc10), a small membrane protein which is down regulated as cancer develops from pre-malignant lesions in the bladder, can serve as a heart homing receptor. The identified receptor clone 46 represents a portion of the mouse homolog of bc10. The full length murine bc10 nucleic acid and amino acid sequences are provided herein as SEQ ID NOS: 34 and 35, respectively (see Genbank accession 20072483). As shown in Table 1 and FIG. 2F, phage expressing two peptides that bound clone 46, CPKTRRVPC (SEQ ID NO: 12) and CSGMARTKC (SEQ ID NO: 13), demonstrated about 60- and 10-fold selectivity in heart homing, respectively.

Figure 3:
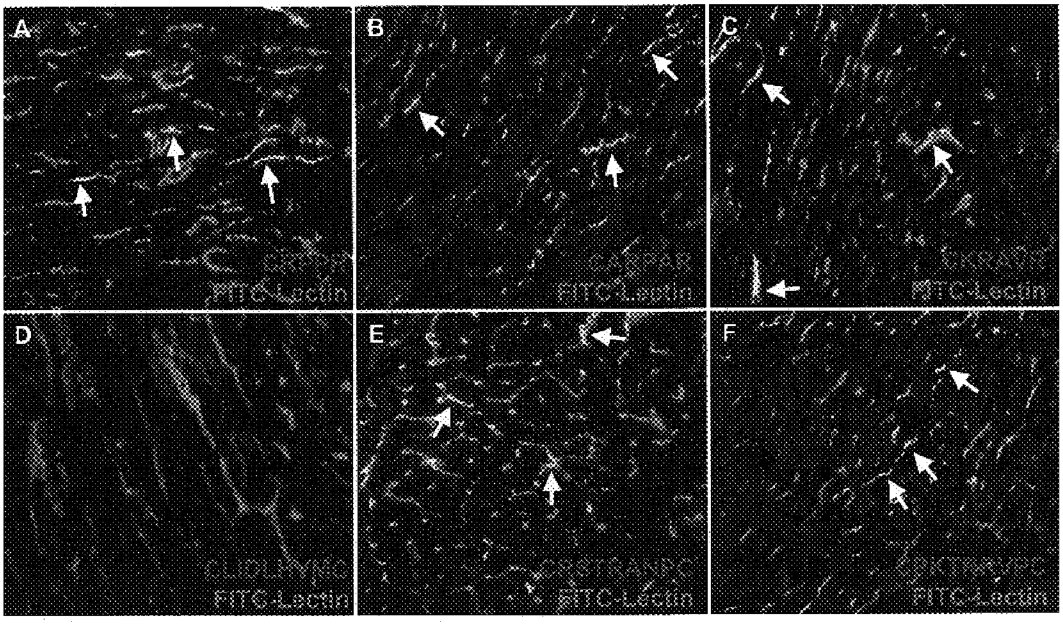
FIG. 3 shows that phage displaying heart-homing peptides co-localize with a marker of vascular endothelial cells in the heart. Phage were intravenously injected into mice together with fluorescein-conjugated tomato lectin (green), and sections of heart tissue stained with rabbit anti-T7 antibody and anti-rabbit-Alexa594 (red). (A) CRPPR (SEQ ID NO: 1) phage staining. (B) CARPAR (SEQ ID NO: 5) phage staining. (C) CKRAVR (SEQ ID NO: 7) phage staining. (D) CLIDLHVMC (SEQ ID NO: 10) phage staining. (E) CRSTRANPC (SEQ ID NO: 11) phage staining. (F) CPKTRRVPC (SEQ ID NO: 12) phage staining. Arrows indicate some representative double-positive blood vessels (yellow). Magnification 200×.

As additionally disclosed herein, several heart-homing peptides were analyzed for the ability to bind heart endothelia in vivo and for specific binding to their putative receptors. Phage-displaying the heart homing peptides SEQ ID NO: 1, SEQ ID NO: 5, SEQ ID NO: 7, SEQ ID NO: 11 and SEQ ID NO: 12 were individually injected into mice with fluorescein-conjugated tomato lectin, a blood vessel marker, and localization of the phage observed with anti-T7 antibody. As shown in FIGS. 3A to C, E and F, phage displaying SEQ ID NOS: 1, 5, 7, 11 or 12 were present in heart endothelia and absent from other tissues, while a negative control phage, which displayed peptide SEQ ID NO: 10, was absent from the heart and other tissues. These results demonstrate that phage displaying peptides CRPPR (SEQ ID NO: 1), CARPAR (SEQ ID NO: 5), CKRAVR (SEQ ID NO: 7), CRSTRANPC (SEQ ID NO: 11) or CPKTRRVPC (SEQ ID NO: 12) localize to heart vasculature in vivo. In addition, real time (RT)-PCR and in situ hybridization analysis showed that four cognate receptors for heart homing peptides, HLP/CRIP2, Sigirr/TIR8, MpcII-3-related protein and bc10, were expressed in the heart endothelia. These receptors were also preferentially expressed in the heart as compared to other tissues assayed (see FIG. 5). Although the heart endothelial receptors HLP/CRIP2, Sigirr/TIR8, MpcII-3-related protein and bc10 were not expressed exclusively in the heart, their preferential expression in the heart resulted in homing peptides which concentrated test phage in the heart with a selectivity of about 20- to 300-fold. This 20- to 300-fold selectivity in heart homing is significantly increased as compared to the heart homing previously observed with other molecules.

Figure 4:
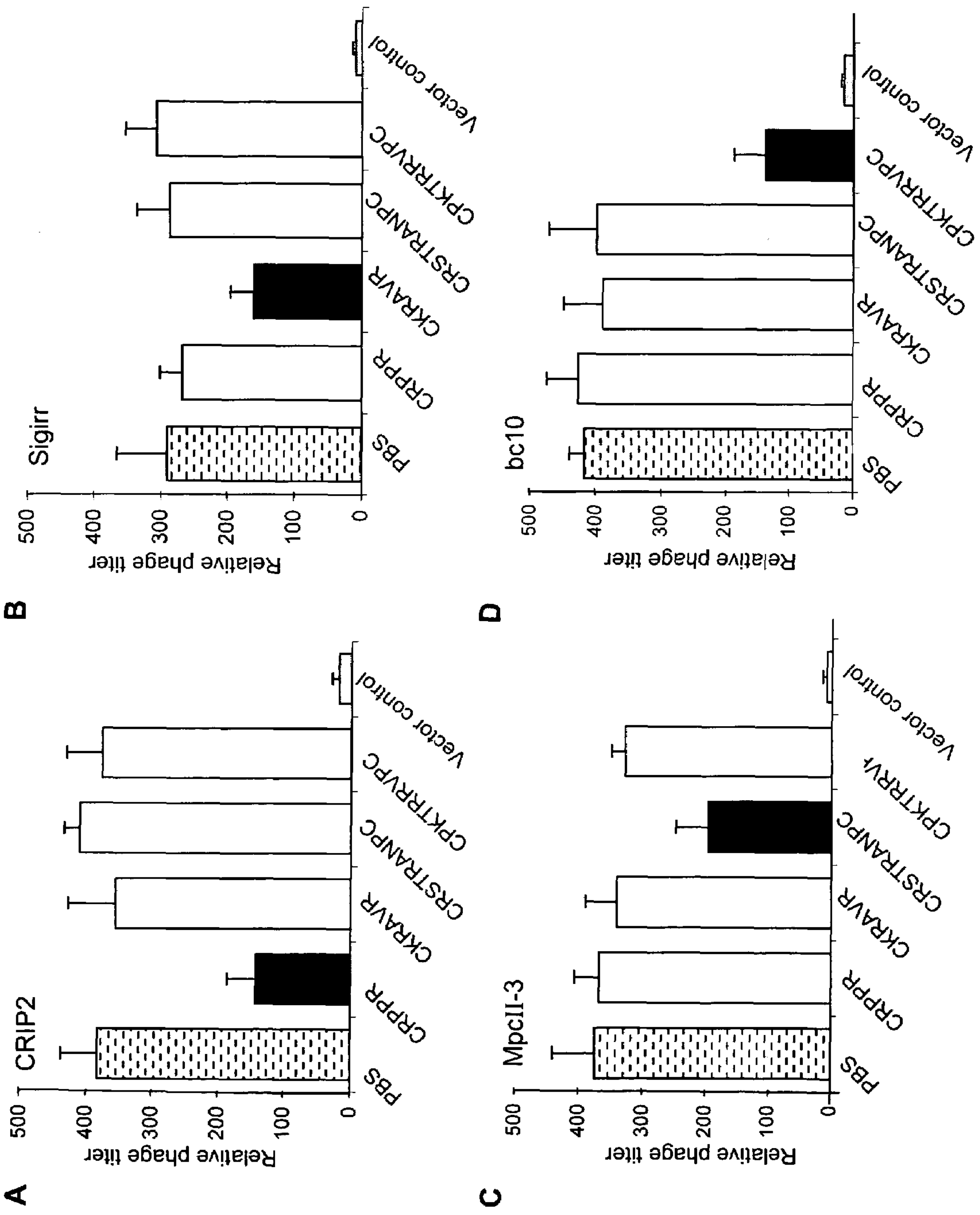
FIG. 4 shows that phage displaying heart-homing peptides specifically bind to cells transfected with cognate receptor. Putative receptors for heart homing peptides identified in the two-hybrid screen (Table 1) were expressed in 293T cells from transfected cDNA; transfected cells were used to test binding of cognate phage displaying the relevant heart homing peptide either in buffer or in the presence of synthetic peptides representing each of the corresponding peptides (100 mg/ml). Each phage bound to cells expressing its putative cognate receptor (striped column) 300 to 500-fold more than to cells transfected with the empty vector control (gray column). In each case, binding of phage to transfected cells was inhibited by competition with an excess of cognate peptide (black column), but not by competition with unrelated heart homing peptides (white columns). Each of the four transfected cell lines was assayed with free peptide CRPPR (SEQ ID NO: 1), CKRAVR (SEQ ID NO: 7), CRSTRANPC (SEQ ID NO: 11) and CPKTRRVPC (SEQ ID NO: 12). (A) Binding of phage expressing cognate peptide CRPPR (SEQ ID NO: 1) to CRIP2-transfected cells; (B) Binding of phage expressing cognate peptide CKRAVR (SEQ ID NO: 7) to Sigirr-transfected cells; (C) Binding of phage expressing cognate peptide CRSTRANPC (SEQ ID NO: 11) to cells transfected with the MpcII-3-related protein SEQ ID NO: 33; (D) Binding of phage expressing cognate peptide CPKTRRVPC (SEQ ID NO: 12) to bc10 transfected cells.

As further disclosed herein, phage displaying cognate peptides were assayed for the ability to bind to cells transfected with full-length cognate receptor. As shown in FIG. 4, phage expressing the heart homing peptides bound to cells transfected with the corresponding cognate receptor 300 to 500-fold more than control phage, and phage binding was inhibited in the presence of 100 μg/ml cognate peptide but not by unrelated homing peptide. These results confirm that the heart homing peptide CRPPR (SEQ ID NO: 1) specifically binds the receptor HLP/CRIP2; the heart homing peptide CKRAVR (SEQ ID NO: 7) specifically binds the receptor Sigirr/TIR8; the heart homing peptide CRSTRANPC (SEQ ID NO: 11) specifically binds the MpcII-3-related protein receptor; and the heart homing peptide CPKTRRVPC (SEQ ID NO: 12) specifically binds the receptor bc10.

Figure 6:
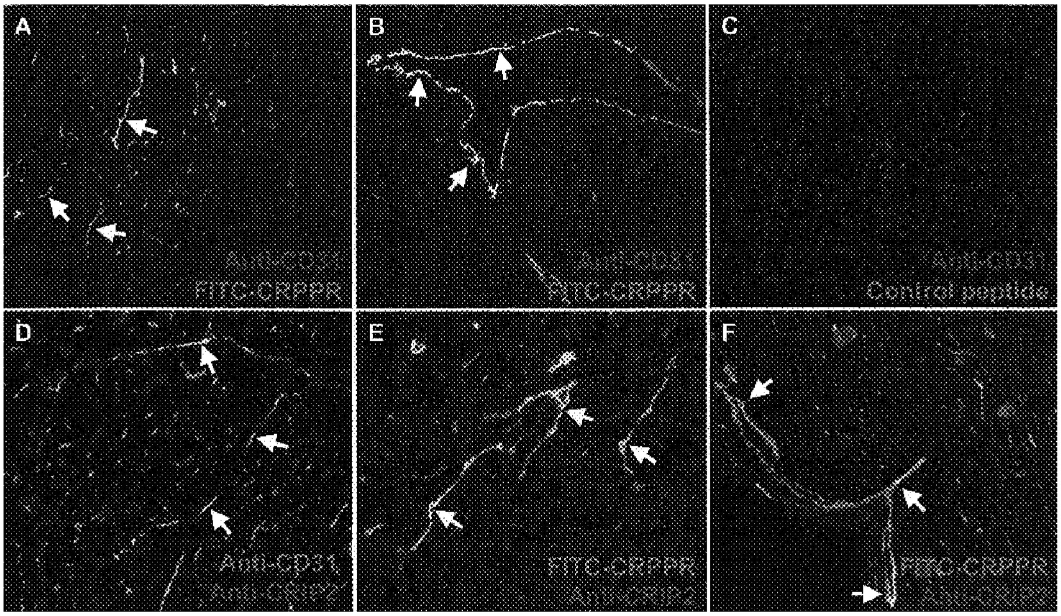
FIG. 6 shows that the CRPPR (SEQ ID NO: 1) peptide and cognate receptor CRIP2 co-localize with CD31 in endothelial cells of heart vessels. Fluorescein-conjugated CRPPR (SEQ ID NO: 1) peptide was intravenously injected into mice, and tissues collected two hours later for staining with antibodies against the endothelial marker, CD31. The fluorescent peptide is shown in green while the CD31 marker is shown in red. (A) Co-localization of SEQ ID NO: 1 and CD31 in heart blood vessels. (B) Co-localization of SEQ ID NO: 1 and CD31 in endocardium. (C) Control peptide is not observed in the heart. (D) Anti-CRIP2 antibody stains heart endothelial cells (red), co-localizing with CD31. (E) Anti-CRIP2 antibody co-localizes with injected CRPPR (SEQ ID NO: 1) peptide in heart blood vessels. (F) Anti-CRIP2 antibody co-localizes with injected CRPPR (SEQ ID NO: 1) peptide in endocardium.
Figure 7:
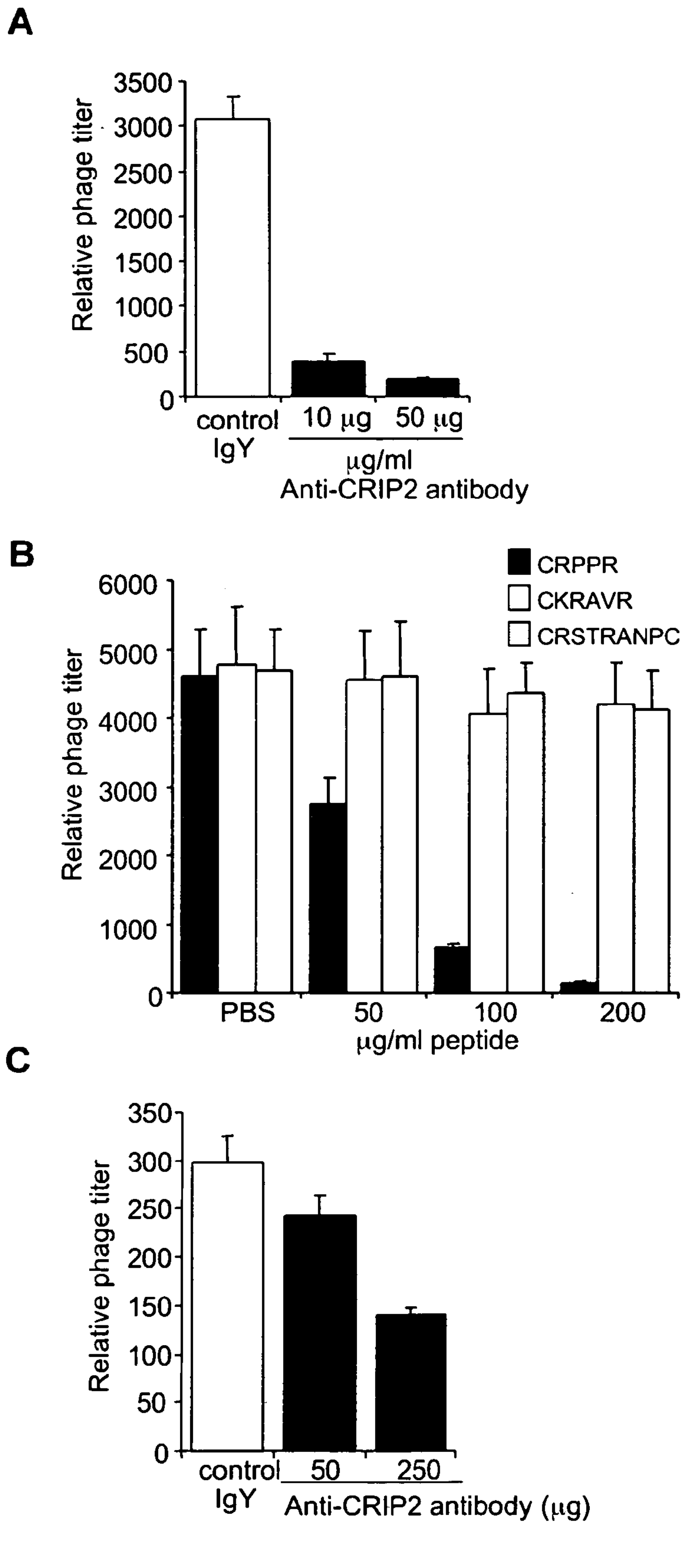
FIG. 7 shows that CRPPR (SEQ ID NO: 1)-displaying phage bind to heart cells and that the homing of the SEQ ID NO: 1-displaying phage is blocked by anti-CRIP2 antibodies. CRPPR (SEQ ID NO: 1)-displaying phage were incubated with cell suspensions prepared from the heart; phage binding was measured in the presence and absence of various concentrations of the indicated antibodies or peptides. (A) A chicken anti-CRIP2 antibody blocked SEQ ID NO: 1-displaying phage binding to heart cells; normal IgY was used as the negative control. (B) Dose dependent inhibition of SEQ ID NO: 1-displaying phage binding by free CRPPR (SEQ ID NO: 1) peptide and lack of inhibition by two unrelated heart-homing peptides confirmed the specificity of the ex vivo phage binding system. (C) In vivo homing of the CRPPR (SEQ ID NO: 1)-displaying phage to the heart was inhibited by co-injected anti-CRIP2 antibody. Shown are the mean and standard deviation from three separate experiments.

Additional results disclosed herein demonstrate co-localization of peptide CRPPR (SEQ ID NO: 1) with cognate receptor HLP/CRIP2. As shown herein in FIG. 6, fluorescence from intravenously injected CRPPR (SEQ ID NO: 1) peptide co-localized extensively with the vascular marker CD31 in both heart blood vessels and endocardium, while a fluorescein-labeled control peptide was not detected in the heart. Anti-HLP/CRIP2 antibody staining also co-localized with the vascular marker (FIG. 6D) and peptide CRPPR (SEQ ID NO: 1; FIGS. 6E and 6F) in heart vessels and heart endocardium. The specificity of CRPPR (SEQ ID NO: 1)-phage binding to heart vessels with HLP/CRIP2 was demonstrated using competition assays with free CRPPR (SEQ ID NO: 1) peptide, which blocked binding of CRPPR (SEQ ID NO: 1)-displaying phage to heart-derived cell suspensions in a dose-dependent manner (FIGS. 7A and B). In addition, anti-HLP/CRIP2 antibody inhibited CRPPR (SEQ ID NO: 1)-phage homing when co-injected with the phage (FIG. 7C). These results substantiate that peptide CRPPR (SEQ ID NO: 1) selectively homes to heart vasculature through specific binding to HLP/CRIP2.

Based on the above findings, the present invention provides a conjugate containing a therapeutic agent linked to a homing molecule that selectively homes to heart vasculature and specifically binds cysteine-rich protein 2 (HLP/CRIP2; SEQ ID NO: 25). In such a conjugate, the homing molecule can home to the heart in vivo with a selectivity, for example, of at least 5-fold relative to non-recombinant phage, and can be, for example, a peptide or peptidomimetic. In one embodiment, a conjugate of the invention includes a homing peptide or peptidomimetic containing the amino acid sequence CRPPR (SEQ ID NO: 1) or a conservative variant or peptidomimetic thereof. In another embodiment, a conjugate of the invention includes a homing peptide or peptidomimetic that contains the amino acid sequence CGRKSKTVC (SEQ ID NO: 2) or a conservative variant or peptidomimetic thereof. Such a homing peptide or peptidomimetic optionally can be conformationally constrained.

A variety of therapeutic agents are useful in the conjugates of the invention which incorporate a homing molecule that selectively homes to heart vasculature and specifically binds HLP/CRIP2 (SEQ ID NO: 25). Useful therapeutic agents include, without limitation, angiogenic agents, anti-thrombotic agents, anti-inflammatory agents, immunosuppressive agents, anti-arrhythmic agents, tumor necrosis factor inhibitors, endothelin inhibitors, angiotensin-converting enzyme (ACE) inhibitors, calcium antagonists, antibiotic agents, antiviral agents and viral vectors. In one embodiment, the invention provides a conjugate which contains an angiogenic agent linked to a homing molecule that selectively homes to heart vasculature and specifically binds HLP/CRIP2 (SEQ ID NO: 25). In another embodiment, the invention provides a conjugate which contains an anti-thrombotic agent linked to a homing molecule that selectively homes to heart vasculature and specifically binds HLP/CRIP2 (SEQ ID NO: 25).

The present invention additionally provides a conjugate containing a therapeutic agent linked to a homing molecule that selectively homes to heart vasculature and specifically binds receptor clone 9 (SEQ ID NO: 27). In one embodiment, a conjugate of the invention includes a homing peptide or peptidomimetic containing the amino acid sequence CARPAR (SEQ ID NO: 5) or a conservative variant or peptidomimetic thereof. In another embodiment, a conjugate of the invention includes a homing peptide or peptidomimetic that contains the amino acid sequence CPKRPR (SEQ ID NO: 6) or a conservative variant or peptidomimetic thereof. Any of a variety of therapeutic agents are useful in the conjugates of the invention which incorporate a homing molecule that selectively homes to heart vasculature and specifically binds receptor clone 9 (SEQ ID NO: 27). Useful therapeutic agents include, without limitation, angiogenic agents, anti-thrombotic agents, anti-inflammatory agents, immunosuppressive agents, anti-arrhythmic agents, tumor necrosis factor inhibitors, endothelin inhibitors, angiotensin-converting enzyme inhibitors, calcium antagonists, antibiotic agents, antiviral agents and viral vectors. In one embodiment, the invention provides a conjugate which contains an angiogenic agent linked to a homing molecule that selectively homes to heart vasculature and specifically binds receptor clone 9 (SEQ ID NO: 27). In another embodiment, the invention provides a conjugate which contains an anti-thrombotic agent linked to a homing molecule that selectively homes to heart vasculature and specifically binds receptor clone 9 (SEQ ID NO: 27).

Further provided herein is a conjugate containing a therapeutic agent linked to a homing molecule that selectively homes to heart vasculature and specifically binds single Ig IL-2 receptor related protein (Sigirr/TIR8; SEQ ID NO: 29). As a non-limiting example, a homing molecule useful in such a conjugate can home to the heart in vivo with a selectivity of at least 5-fold relative to non-recombinant phage. As a further non-limiting example, a homing molecule that specifically binds Sigirr/TIR8 can be a homing peptide or peptidomimetic.

A variety of homing peptides and peptidomimetics that specifically bind Sigirr/TIR8 (SEQ ID NO: 29) are useful in the conjugates of the invention, including, without limitation, homing peptides or peptidomimetics containing the amino acid sequence CKRAVR (SEQ ID NO: 7) or a conservative variant or peptidomimetic thereof. Homing peptides and peptidomimetics useful in the invention further include, without limitation, peptides and peptidomimetics containing the amino acid sequence CRNSWKPNC (SEQ ID NO: 8) or a conservative variant or peptidomimetic thereof, such peptides and peptidomimetics may or may not be conformationally constrained. Additional homing peptides and peptidomimetics useful in the invention include, without limitation, those containing the amino acid sequence RGSSS (SEQ ID NO: 9) or a conservative variant or peptidomimetic thereof.

Any of a variety of therapeutic agents are useful in conjugates that contain a therapeutic agent linked to a homing molecule that selectively homes to heart vasculature and specifically binds Sigirr/TIR8 (SEQ ID NO: 29). Therapeutic agents useful in the invention include, yet are not limited to, angiogenic agents, anti-thrombotic agents, anti-inflammatory agents, immunosuppressive agents, anti-arrhythmic agents, tumor necrosis factor inhibitors, endothelin inhibitors, angiotensin-converting enzyme inhibitors, calcium antagonists, antibiotic agents, antiviral agents and viral vectors. In one embodiment, the invention provides a conjugate which contains an angiogenic agent linked to a homing molecule that selectively homes to heart vasculature and specifically binds Sigirr/TIR8 (SEQ ID NO: 29). In another embodiment, the invention provides a conjugate which contains an anti-thrombotic agent linked to a homing molecule that selectively homes to heart vasculature and specifically binds Sigirr/TIR8 (SEQ ID NO: 29).

Also provided herein is a conjugate which contains a therapeutic agent linked to a homing molecule that selectively homes to heart vasculature and specifically binds SEQ ID NO: 33. In one embodiment, a conjugate of the invention includes a homing molecule that homes to the heart in vivo with a selectivity of at least 5-fold relative to non-recombinant phage. In another embodiment, a conjugate of the invention includes a homing molecule which is a homing peptide or peptidomimetic. In further embodiments, a conjugate of the invention includes a homing peptide or peptidomimetic that contains the amino acid sequence CRSTRANPC (SEQ ID NO: 11) or a conservative variant or peptidomimetic thereof. Such a homing molecule can optionally be conformationally constrained. It is understood that any of a variety of therapeutic agents can be useful in the conjugates of the invention including, without limitation, angiogenic agents, anti-thrombotic agents, anti-inflammatory agents, immunosuppressive agents, anti-arrhythmic agents, tumor necrosis factor inhibitors, endothelin inhibitors, angiotensin-converting enzyme inhibitors, calcium antagonists, antibiotic agents, antiviral agents and viral vectors. As one example, a conjugate of the invention can contain an angiogenic agent linked to a homing molecule that selectively homes to heart vasculature and specifically binds SEQ ID NO: 33. As another example, a conjugate of the invention can contain an anti-thrombotic agent linked to a homing molecule that selectively homes to heart vasculature and specifically binds SEQ ID NO: 33.

Also provided herein is a conjugate containing a therapeutic agent linked to a homing molecule that selectively homes to heart vasculature and specifically binds murine bladder cancer-associated protein homolog (bc10; SEQ ID NO: 35). In such a conjugate, the homing molecule can home to the heart in vivo with a selectivity, for example, of at least 5-fold relative to non-recombinant phage. The homing molecule can be, without limitation, a peptide or peptidomimetic. Any of a variety of homing molecules that specifically bind bc10 (SEQ ID NO: 35) can be useful in the conjugates of the invention including, without limitation, homing peptides and peptidomimetics that contain the amino acid sequence CPKTRRVPC (SEQ ID NO: 12) or a conservative variant or peptidomimetic thereof. Useful homing molecules that specifically bind bc10 (SEQ ID NO: 35) further include, without limitation, homing peptides and peptidomimetics that contain the amino acid sequence CSGMARTKC (SEQ ID NO: 13) or a conservative variant or peptidomimetic thereof. Useful homing molecules further include, without limitation, conformationally constrained forms of homing peptides and peptidomimetics including the amino acid sequence SEQ ID NO: 12 or SEQ ID NO: 13 or a conservative variant or peptidomimetic thereof.

One skilled in the art understands that any of a variety of therapeutic agents can be useful in the conjugates of the invention including, without limitation, angiogenic agents, anti-thrombotic agents, anti-inflammatory agents, immunosuppressive agents, anti-arrhythmic agents, tumor necrosis factor inhibitors, endothelin inhibitors, angiotensin-converting enzyme inhibitors, calcium antagonists, antibiotic agents, antiviral agents and viral vectors. In one embodiment, a conjugate of the invention contains an angiogenic agent linked to a homing molecule that selectively homes to heart vasculature and specifically binds bc10 (SEQ ID NO: 35). In another embodiment, a conjugate of the invention contains an anti-thrombotic agent linked to a homing molecule that selectively homes to heart vasculature and specifically binds bc10 (SEQ ID NO: 35).

In particular embodiments, the peptide or peptidomimetic portion of a conjugate of the invention has a defined length. The peptide or peptidomimetic portion of the conjugate can have, without limitation, a length of at most 10, 20, 30, 40, 50, 100, 150, 200, 250, 300, 400, 500, 600, 700, 800, 900, 1000 or 2000 residues. In other embodiments, the peptide or peptidomimetic portion of the conjugate has a length of at least 5, 10, 20, 30, 50, 100, 150, 200, 250, or 300 residues. It is understood that the term "peptide or peptidomimetic portion of the conjugate" means the total number of residues in the homing peptide or peptidomimetic and any contiguous protein, peptide or peptidomimetic, such as a therapeutic protein or pro-apoptotic peptide.

As disclosed herein, peptides SEQ ID NOS: 1 and 2 recognize a target "receptor" which is expressed on heart endothelium and which is not expressed to the same extent in other tissues. The endothelial and tissue selective expression of this target receptor, identified herein as HLP/CRIP2, form the basis for the selective homing activity of peptides SEQ ID NOS: 1 and 2 and related peptides and peptidomimetics, as well as other molecules with similar binding specificity. Based on these discoveries, it is clear that molecules structurally unrelated to SEQ ID NOS: 1 and 2 but with specific HLP/CRIP2 binding activity also will share the characteristic of selectively homing to heart vasculature. Such molecules can be identified, for example, by the ability to specifically bind to, or to compete with SEQ ID NO: 1 or 2 for binding to, HLP/CRIP2-expressing cells such as the 293T cells transfected with HLP/CRIP2 disclosed herein. Selective homing to heart vasculature can be readily confirmed, for example, as described herein in Example II.

Thus, the present invention provides a homing molecule that selectively homes to heart vasculature and specifically binds cysteine-rich protein 2 (HLP/CRIP2; SEQ ID NO: 25). In one embodiment, the homing molecule which specifically binds HLP/CRIP2 (SEQ ID NO: 25) is a molecule other than an antibody or antigen-binding fragment thereof. In a further embodiment, the homing molecule which specifically binds HLP/CRIP2 (SEQ ID NO: 25) is a peptide or peptidomimetic. In addition to the HLP/CRIP2 (SEQ ID NO: 25)-binding molecules disclosed herein, CRPPR (SEQ ID NO: 1) and CGRKSKTVC (SEQ ID NO: 2), screening methods for identification of additional, structurally related or unrelated, homing molecules also are provided herein below.

Additional target receptors for molecules that selectively home to heart vasculature also have been identified herein. Receptor clone 9 (SEQ ID NO: 27) has been identified as a receptor which specifically binds the heart homing peptides SEQ ID NOS: 5 and 6, and forms the basis for the ability of these peptides and additional peptides, peptidomimetics and other molecules with similar binding activity to selectively home to heart vasculature. From the above, it is clear that molecules structurally unrelated to SEQ ID NOS: 5 or 6 but with specific receptor clone 9 (SEQ ID NO: 27)-binding activity also share the characteristic of selectively homing to heart vasculature. Such homing molecules can be identified by the ability to specifically bind to, or to compete with SEQ ID NO: 5 or 6 for binding to, receptor clone 9 (SEQ ID NO: 27). Specific binding can be assayed using purified SEQ ID NO: 27 or, for example, cells transfected with a SEQ ID NO: 27-encoding nucleic acid molecule such as SEQ ID NO: 26.

Based on the above, the invention provides a homing molecule that selectively homes to heart vasculature and specifically binds receptor clone 9 (SEQ ID NO: 27). In one embodiment, the homing molecule which specifically binds receptor clone 9 (SEQ ID NO: 27) is a molecule other than an antibody or antigen-binding fragment thereof. In a further embodiment, the homing molecule which specifically binds receptor clone 9 (SEQ ID NO: 27) is a peptide or peptidomimetic. Exemplary peptides and peptidomimetics which specifically bind receptor clone 9 (SEQ ID NO: 27) are disclosed herein, and screening methods suitable for identification of additional homing molecules that selectively home to heart vasculature and specifically bind receptor clone 9 (SEQ ID NO: 27) are provided below.

As further disclosed herein, the endothelial and heart-selective expression of Sigirr/TIR8, a polypeptide which specifically binds SEQ ID NOS: 7, 8 and 9, forms the basis for the ability of these peptides and additional peptides, peptidomimetics and other molecules with similar binding activity to selectively home to heart vasculature. From the above, it is clear that molecules structurally unrelated to SEQ ID NOS: 7, 8 or 9 but with specific Sigirr/TIR8 binding activity also share the characteristic of selectively homing to heart vasculature. Such homing molecules can be identified by the ability to specifically bind to, or to compete with SEQ ID NO: 7, 8 or 9 for binding to, Sigirr/TIR8. Specific binding can be assayed using purified Sigirr/TIR8 or, for example, cells such as Sigirr/TIR8-transfected 293T cells disclosed in the examples below.

Based on identification of Sigirr/TIR8 as a heart-homing receptor, the present invention provides a homing molecule that selectively homes to heart vasculature and specifically binds Sigirr/TIR8 (SEQ ID NO: 29). In one embodiment, the homing molecule which specifically binds Sigirr/TIR8 (SEQ ID NO: 29) is a molecule other than an antibody or antigen-binding fragment thereof. In a further embodiment, the homing molecule which specifically binds Sigirr/TIR8 (SEQ ID NO: 29) is a peptide or peptidomimetic. Exemplary peptides and peptidomimetics which specifically bind Sigirr/TIR8 (SEQ ID NO: 29) are disclosed herein. Furthermore, screening methods suitable for routine identification of additional homing molecules that selectively home to heart vasculature and specifically bind Sigirr/TIR8 (SEQ ID NO: 29) are provided herein below.

Peptide CRSTRANPC (SEQ ID NO: 11) recognizes another target "receptor" which is selectively expressed on heart endothelium. Due to the endothelial and tissue selective expression of the MpcII-3-related protein SEQ ID NO: 33, peptide SEQ ID NO: 11 as well as related peptides, peptidomimetics and other molecules with similar binding specificity can selectively home to heart vasculature. Such homing molecules include those which are structurally unrelated to peptide SEQ ID NO: 11 but which also specifically bind to the MpcII-3 related protein SEQ ID NO: 33. In view of the above, it is clear that additional molecules which selectively home to heart vasculature can be identified by their ability to specifically bind to, or to compete with SEQ ID NO: 11 for binding to, a MpcII-3-related protein, including purified MpcII-3-related protein or cells expressing a MpcII-3-related protein on the cell surface.

From the finding that MpcII-3-related protein (SEQ ID NO: 33) is a heart-homing receptor, the present invention provides a homing molecule that selectively homes to heart vasculature and specifically binds SEQ ID NO: 33. In one embodiment, the homing molecule which specifically binds SEQ ID NO: 33 is a molecule other than an antibody or antigen-binding fragment thereof. In another embodiment, the homing molecule which specifically binds SEQ ID NO: 33 is a peptide or peptidomimetic. Exemplary peptides and peptidomimetics which specifically bind SEQ ID NO: 33 are disclosed herein, as are screening methods suitable for identification of additional homing molecules that selectively home to heart vasculature and specifically bind SEQ ID NO: 33.

Another target receptor, bc10, was further identified herein through the specific binding activity of SEQ ID NOS: 12 and 13. The endothelial and heart-selective expression of this receptor form the basis for the selective homing activity of peptides SEQ ID NOS: 12 and 13 as well as related peptides, peptidomimetics and other molecules with similar binding specificity. Based on the findings disclosed herein, one skilled in the art understands that molecules structurally unrelated to SEQ ID NOS: 12 and 13 also can selectively home to heart vasculature when they share the characteristic of specifically binding bc10. Thus, additional homing molecules can be identified, for example, by the ability to specifically bind to, or to compete with SEQ ID NO: 12 or 13 for binding to, target receptor bc10, which can be provided, for example, in the form of purified bc10 or bc10-expressing cells such as bc10-transfected 293T cells. Selective homing to heart vasculature can be readily confirmed, for example, as described herein in Example II.

Based on the discovery that bc10 is the cognate receptor for peptides SEQ ID NOS: 12 and 13, the present invention provides a homing molecule that selectively homes to heart vasculature and specifically binds bc10 (SEQ ID NO: 35). In one embodiment, the invention provides a homing molecule which specifically binds bc10 (SEQ ID NO: 35) and which is a molecule other than an antibody or antigen-binding fragment thereof. In another embodiment, the invention provides a homing molecule which specifically binds bc10 (SEQ ID NO: 35) and which is a peptide or peptidomimetic. Peptides SEQ ID NOS: 12 and 13 and conservative variants thereof are disclosed herein as molecules which specifically bind bc10 (SEQ ID NO: 35). In addition, the screening methods disclosed further below are suitable for identification of other homing molecules, including but not limited to, homing peptides and peptidomimetics.

For convenience, the five target receptors identified herein, HLP/CRIP2, receptor clone 9, Sigirr/TIR8, MpcII-3-related protein, and bc10, are collectively termed "heart-homing receptors."

As indicated above, the present invention provides a variety of homing molecules that selectively home to heart vasculature. As used herein, the term "molecule" is used broadly to mean a polymeric or non-polymeric organic chemical such as a small molecule drug; a nucleic acid molecule such as an RNA, a cDNA or an oligonucleotide; a peptide or peptidomimetic; or a protein such as an antibody or a growth factor receptor or a fragment thereof such as an Fv, Fd, or Fab fragment of an antibody containing the antigen-binding domain. In one embodiment, the molecule is an organic chemical other than an antibody or antigen-binding fragment thereof. In another embodiment, the molecule is a peptide or peptidomimetic.

The term "homing molecule" as used herein, means any molecule that selectively localizes in vivo to heart vasculature in preference to most other tissues and vasculature. Similarly, the term "homing peptide" or "homing peptidomimetic" means a peptide or peptidomimetic that selectively localizes in vivo to the heart vasculature in preference to most other tissues and vasculature.

The term "selectively homes," as used herein in reference to a molecule, means that, in vivo, the homing molecule localizes preferentially to heart vasculature as compared to most other tissues or vasculature. Selective homing generally is characterized by at least a two-fold greater localization in heart vasculature as compared to other tissues such as brain, lung, kidney and muscle. A homing molecule can be characterized by 5-fold, 10-fold, 20-fold or more preferential localization to heart vasculature as compared to many or most non-tumor tissues. It is understood that a homing molecule can home, in part, to vasculature or tissue outside the heart or to a small population of cells outside of the heart in addition to selectively homing to heart vasculature.

As discussed above, a homing molecule of the invention specifically binds one of the heart-homing receptors of the invention. As used herein, the term "specifically binds" or "specifically binding" means binding that is measurably different from a non-specific interaction. Specific binding can be measured, for example, by determining binding of a molecule compared to binding of a control molecule, which generally is a molecule of similar structure that does not have binding activity. Specific binding also can be indicated if the homing molecule has measurably higher affinity for cells transfected with cognate heart-homing receptor (HLP/CRIP2, receptor clone 9, Sigirr/TIR8, MpcII-3-related protein or bc10) than for cells that do not express the cognate receptor. The measurably higher affinity can be, for example, an increase of at least 100-fold, 200-fold, 300-fold, 500-fold or more for cells transfected with cognate receptor as compared to control cells. Binding specificity also can be confirmed, for example, by competitive inhibition with a known receptor-binding molecule.

Furthermore, the term specifically binding, as used herein, encompasses both low and high affinity specific binding. Specific binding can be exhibited, for example, by a low affinity homing molecule having a Kd of at least about $10^{-4}$ M. For example, if a heart-homing receptor has more than one binding site, a homing molecule having low affinity can be useful for targeting heart vasculature. Specific binding also can be exhibited by a high affinity homing molecule, for example, a homing molecule having a Kd of at least about $10^{-5}$ M. Such a molecule can have, for example, a Kd of at least about $10^{-6}$ M, at least about $10^{-7}$ M, at least about $10^{-8}$ M, at least about $10^{-9}$ M, at least about $10^{-10}$ M, or can have a Kd of at least about $10^{-11}$ M or $10^{-12}$ M or greater. Both low and high affinity homing molecules are useful and encompassed by the invention. Low affinity homing molecules can be useful in targeting, without limitation, multivalent conjugates including viruses and other particles. High affinity homing molecules are useful in targeting, without limitation, multivalent and univalent conjugates.

Also provided herein are multivalent conjugates, which incorporate at least two homing molecules that each selectively homes to heart vasculature. In particular embodiments, a multivalent conjugate of the invention includes at least ten or at least 100 of such homing molecules. A variety of therapeutic agents are useful in the multivalent conjugates of the invention including, but not limited to, phage and other therapeutic agents described further below. In one embodiment, the invention provides a multivalent conjugate containing at least two homing peptides or peptidomimetics that each selectively homes to heart vasculature and specifically binds HLP/CRIP2 (SEQ ID NO: 25), receptor clone 9 (SEQ ID NO: 27), Sigirr/TIR8 (SEQ ID NO: 29), MpcII-3-related protein (SEQ ID NO: 33) or bc10 (SEQ ID NO: 35). In another embodiment, such a conjugate contains at least ten homing peptides or peptidomimetics that each selectively homes to heart vasculature and specifically binds HLP/CRIP2 (SEQ ID NO: 25), receptor clone 9 (SEQ ID NO: 27), Sigirr/TIR8 (SEQ ID NO: 29), MpcII-3-related protein (SEQ ID NO: 33) or bc10 (SEQ ID NO: 35). In still another embodiment, a conjugate of the invention contains at least 100 homing peptides or peptidomimetics that each selectively homes to heart vasculature and specifically binds HLP/CRIP2 (SEQ ID NO: 25), receptor clone 9 (SEQ ID NO: 27), Sigirr/TIR8 (SEQ ID NO: 29), MpcII-3-related protein (SEQ ID NO: 33) or bc10 (SEQ ID NO: 35).

In specific embodiments, a multivalent conjugate of the invention includes two or more, three or more, five or more, ten or more, twenty or more, thirty or more, forty or more, fifty or more, 100 or more, 200 or more, 300 or more, 400 or more, 500 or more or 100 or more homing molecules that selectively home to heart vasculature and specifically bind HLP/CRIP2 (SEQ ID NO: 25), receptor clone 9 (SEQ ID NO: 27), Sigirr/TIR8 (SEQ ID NO: 29), MpcII-3-related protein (SEQ ID NO: 33) or bc10 (SEQ ID NO: 35). In one embodiment, the homing molecules specifically bind the same heart-homing receptor. In another embodiment, the homing molecules have an identical amino acid sequence. In a further embodiment, the multivalent conjugate includes homing molecules having non-identical amino acid sequences. Moieties useful in a multivalent conjugate of the invention that incorporates multiple homing molecules include, but are not limited to, phage; retroviruses; adenoviruses; adeno-associated viruses and other viruses; cells; liposomes; polymeric matrices; non-polymeric matrices or particles such as gold particles; microdevices; nanodevices; and nano-scale semiconductor materials.

A multivalent conjugate of the invention can contain, for example, a liposome or other polymeric matrix linked to at least two homing molecules that each selectively homes to heart vasculature and specifically binds HLP/CRIP2 (SEQ ID NO: 25), receptor clone 9 (SEQ ID NO: 27), Sigirr/TIR8 (SEQ ID NO: 29), MpcII-3-related protein (SEQ ID NO: 33) or bc10 (SEQ ID NO: 35). If desired, the liposome or other polymeric matrix can be linked to at least ten or at least 100 of such homing molecules. Homing molecules useful in such a multivalent conjugate can independently include, for example, the amino acid sequence SEQ ID NO: 1, 2, 7, 8, 9, 11, 12 or 13 or a conservative variant or peptidomimetic of such a sequence. Liposomes composed, for example, of phospholipids or other lipids, are nontoxic, physiologically acceptable and metabolizable carriers that are relatively simple to make and administer (Gregoriadis, *Liposome Technology*, Vol. 1 (CRC Press, Boca Raton, Fla. (1984)). One skilled in the art understands that, in a multivalent conjugate of the invention, the liposome or other polymeric matrix additionally can include another component if desired such as, without limitation, a therapeutic agent, anti-angiogenic agent, anti-inflammatory agent or immunosuppressive agent.

The present invention provides a method of treating a cardiovascular disease in a subject by administering to the subject an antibody, or antigen-binding fragment thereof, that selectively homes to heart vasculature and that specifically binds HLP/CRIP2 (SEQ ID NO: 25). The invention further provides a method of directing a moiety to heart vasculature in a subject by administering to the subject a conjugate which contains a moiety linked to an antibody, or antigen-binding fragment thereof, that selectively homes to heart vasculature and that specifically binds HLP/CRIP2 (SEQ ID NO: 25), thereby directing the moiety to heart vasculature. Antibodies useful in the methods of the invention include, without limitation, monoclonal antibodies and antibodies with biological activity. Where a method of the invention is used to direct a moiety to heart vasculature, the moiety can be, without limitation, a detectable moiety or a therapeutic agent such as, without limitation, an angiogenic agent, anti-thrombotic agent, anti-inflammatory agent, immunosuppressive agent, anti-arrhythmic agent, tumor necrosis factor inhibitor, endothelin inhibitor, angiotensin-converting enzyme inhibitor, calcium antagonist, antibiotic agent, antiviral agent or viral vector. Moieties and cardiovascular diseases are described further herein below.

The present invention also provides a method of treating a cardiovascular disease in a subject by administering to the subject an antibody, or antigen-binding fragment thereof, that selectively homes to heart vasculature and that specifically binds SEQ ID NO: 27. The invention additionally provides a method of directing a moiety to heart vasculature in a subject in which a conjugate is administered to a subject, the conjugate containing a moiety linked to an antibody, or antigen-binding fragment thereof, that selectively homes to heart vasculature and specifically binds SEQ ID NO:27, thereby directing the moiety to heart vasculature. In such methods of the invention, the antibody can be, without limitation, a monoclonal antibody or an antibody with biological activity. Where a method of the invention is used to direct a moiety to heart vasculature, the moiety can be, without limitation, a detectable moiety or a therapeutic agent such as, without limitation, an angiogenic agent, anti-thrombotic agent, anti-inflammatory agent, immunosuppressive agent, anti-arrhythmic agent, tumor necrosis factor inhibitor, endothelin inhibitor, angiotensin-converting enzyme inhibitor, calcium antagonist, antibiotic agent, antiviral agent or viral vector.

The present invention also provides a method of treating a cardiovascular disease in a subject by administering to the subject an antibody, or antigen-binding fragment thereof, that selectively homes to heart vasculature and that specifically binds Sigirr/TIR8 (SEQ ID NO: 29). In addition, there is provided herein a method of directing a moiety to heart vasculature in a subject by administering to the subject a conjugate which contains a moiety linked to an antibody, or antigen-binding fragment thereof, that selectively homes to heart vasculature and that specifically binds Sigirr/TIR8 (SEQ ID NO: 29), thereby directing the moiety to heart vasculature. In the methods of the invention, the antibody can be, without limitation, a monoclonal antibody or an antibody with biological activity. As discussed above, where a method of the invention is used to direct a moiety to heart vasculature, the moiety can be, without limitation, a detectable moiety or a therapeutic agent such as, without limitation, an angiogenic agent, anti-thrombotic agent, anti-inflammatory agent, immunosuppressive agent, anti-arrhythmic agent, tumor necrosis factor inhibitor, endothelin inhibitor, angiotensin-converting enzyme inhibitor, calcium antagonist, antibiotic agent, antiviral agent or viral vector.

Further provided herein is a method of treating a cardiovascular disease in a subject by administering to the subject an antibody, or antigen-binding fragment thereof, that selectively homes to heart vasculature and that specifically binds SEQ ID NO: 33. Also provided by the invention is a method of directing a moiety to heart vasculature in a subject by administering to the subject a conjugate which contains a moiety linked to an antibody, or antigen-binding fragment thereof, that selectively homes to heart vasculature and that specifically binds SEQ ID NO: 33, thereby directing the moiety to heart vasculature. Antibodies useful in the invention include, without limitation, monoclonal antibodies as well as antibodies with biological activity. In the methods of the invention for directing a moiety to heart vasculature, the moiety can be, without limitation, a detectable moiety or a therapeutic agent such as, without limitation, an angiogenic agent, anti-thrombotic agent, anti-inflammatory agent, immunosuppressive agent, anti-arrhythmic agent, tumor necrosis factor inhibitor, endothelin inhibitor, angiotensin-converting enzyme inhibitor, calcium antagonist, antibiotic agent, antiviral agent or viral vector.

The present invention additionally provides a method of treating a cardiovascular disease in a subject by administering to the subject an antibody, or antigen-binding fragment thereof, that selectively homes to heart vasculature and that specifically binds bc10 (SEQ ID NO: 35). The invention also provides a method of directing a moiety to heart vasculature in a subject by administering to the subject a conjugate which contains a moiety linked to an antibody, or antigen-binding fragment thereof, that selectively homes to heart vasculature and that specifically binds bc10 (SEQ ID NO: 35), thereby directing the moiety to heart vasculature. A method of the invention can be practiced, for example, with a monoclonal antibody or an antibody with biological activity. In the methods of the invention for directing a moiety to heart vasculature, any of a variety of moieties can be linked to an antibody that specifically binds bc10 (SEQ ID NO: 35). Such moieties include, yet are not limited to, detectable moieties and therapeutic agents such as angiogenic agents, anti-thrombotic agents, anti-inflammatory agents, immunosuppressive agents, anti-arrhythmic agents, tumor necrosis factor inhibitors, endothelin inhibitors, angiotensin-converting enzyme inhibitors, calcium antagonists, antibiotic agents, antiviral agents and viral vectors.

As used herein, the term "antibody" is used in its broadest sense to include polyclonal and monoclonal antibodies, as well as polypeptide fragments of antibodies that retain binding activity for a heart homing receptor of at least about $1\times10^5$ $M^{-1}$. One skilled in the art understands that antibodies that selectively home to heart vasculature, including, without limitation, Fab, $F(ab')_2$ and Fv fragments, can retain binding activity for a heart homing receptor and, thus, are included within the definition of antibody. In addition, the term "antibody," as used herein, encompasses non-naturally occurring antibodies and fragments usually containing, at a minimum, one $V_H$ and one $V_L$ domain, such as chimeric antibodies, humanized antibodies and single chain Fv fragments (scFv) that specifically bind a heart homing receptor. Such non-naturally occurring antibodies can be constructed using solid phase peptide synthesis, produced recombinantly or obtained, for example, by screening phage-displayed or other combinatorial libraries such as those consisting of variable heavy and light chains as described in Borrebaeck (Ed.), *Antibody Engineering* (Second edition) New York: Oxford University Press (1995)) using, for example, an assay described herein below.

Antibodies which selectively home to heart vasculature also can be prepared, for example, using an HLP/CRIP2, receptor clone 9, Sigirr/TIR8, MpcII-3-related protein or bc10 fusion protein or a synthetic peptide encoding a portion of HLP/CRIP2, receptor clone 9, Sigirr/TIR8, MpcII-3-related protein or bc10 as an immunogen. One skilled in the art understands that purified human, murine or other HLP/CRIP2, receptor clone 9, Sigirr/TIR8, MpcII-3-related protein or bc10, which can be produced recombinantly, for example, using the nucleic acid sequences disclosed herein as SEQ ID NO: 24, 26, 28, 32 and 34, as well as fragments and peptide portions of HLP/CRIP2, receptor clone 9, Sigirr/TIR8, MpcII-3-related protein or bc10, can be useful as immunogens for raising anti-HLP/CRIP2, anti-Sigirr/TIR8, anti-MpcII-3-related protein or anti-bc10 antibodies that selectively home to heart vasculature. It is understood that fragments of HLP/CRIP2, receptor clone 9, Sigirr/TIR8, MpcII-3-related protein or bc10 useful as immunogens include, without limitation, fragments that serve to produce antibodies. One skilled in the art further understands that non-immunogenic fragments or synthetic peptides of a heart homing receptor can be made immunogenic by coupling the hapten to a carrier molecule such as bovine serum albumin (BSA) or keyhole limpet hemocyanin (KLH). In addition, various other carrier molecules and methods for coupling a hapten to a carrier molecule are well known in the art as described, for example, by Harlow and Lane, *Antibodies: A Laboratory Manual* (Cold Spring Harbor Laboratory Press, 1988)).

Based on the identification of molecules that selectively home to heart vasculature and their ability to target a linked therapeutic agent to heart vasculature, the present invention provides methods for directing a moiety to heart vasculature and methods of treating a cardiovascular disease. The present invention provides, for example, methods of directing a moiety to heart vasculature in a subject by administering to the subject a conjugate containing a moiety linked to a homing molecule that selectively homes to heart vasculature and specifically binds HLP/CRIP2 (SEQ ID NO: 25), thereby directing the moiety to heart vasculature. In a method of the invention, a homing molecule can home to the heart in vivo with a selectivity, for example, of at least 5-fold relative to non-recombinant phage, and can be, for example, a homing peptide or peptidomimetic. In one embodiment, a method of the invention for directing a moiety to heart vasculature relies on a homing peptide or peptidomimetic containing the amino acid sequence CRPPR (SEQ ID NO: 1) or a conservative variant or peptidomimetic thereof. In another embodiment, a method of the invention relies on a homing peptide or peptidomimetic that contains the amino acid sequence CGRKSKTVC (SEQ ID NO: 2) or a conservative variant or peptidomimetic thereof. A homing peptide or peptidomimetic useful in the invention may optionally be conformationally constrained. Furthermore, any of a variety of moieties can be useful in the methods of the invention including, without limitation, detectable moieties such as radionuclides and fluorescent molecules. Moieties useful in the invention further encompass, without limitation, therapeutic agents such as angiogenic agents, anti-thrombotic agents, anti-inflammatory agents, immunosuppressive agents, anti-arrhythmic agents, tumor necrosis factor inhibitors, endothelin inhibitors, angiotensin-converting enzyme inhibitors, calcium antagonists, antibiotic agents, antiviral agents and viral vectors.

The present invention further provides a method of directing a moiety to heart vasculature in a subject by administering to the subject a conjugate containing a moiety linked to a homing molecule that selectively homes to heart vasculature and specifically binds SEQ ID NO: 27, thereby directing the moiety to heart vasculature. A homing molecule useful in the invention can home to the heart in vivo with a selectivity, for example, of at least 5-fold relative to non-recombinant phage and can be a homing peptide or peptidomimetic. It is understood that any of a variety of homing molecules that specifically bind SEQ ID NO: 27 can be useful for directing a moiety to heart vasculature. Such homing molecules include, but are not limited to, homing peptides and peptidomimetics containing the amino acid sequence CARPAR (SEQ ID NO: 5) or a conservative variant or peptidomimetic thereof; and homing peptides and peptidomimetics containing the amino acid sequence CPKRPR (SEQ ID NO: 6) or a conservative variant or peptidomimetic thereof. Moieties useful in the invention include, without limitation, detectable moieties such as radionuclides and fluorescent molecules as well as therapeutic agents such as angiogenic agents, anti-thrombotic agents, anti-inflammatory agents, immunosuppressive agents, anti-arrhythmic agents, tumor necrosis factor inhibitors, endothelin inhibitors, angiotensin-converting enzyme inhibitors, calcium antagonists, antibiotic agents, antiviral agents and viral vectors.

Further provided herein are methods of directing a moiety to heart vasculature in a subject by administering to the subject a conjugate which contains a moiety linked to a homing molecule that selectively homes to heart vasculature and specifically binds Sigirr/TIR8 (SEQ ID NO: 29), thereby directing the moiety to heart vasculature. As a non-limiting example, a homing molecule useful in a method of the invention can home to the heart in vivo with a selectivity of at least 5-fold relative to non-recombinant phage. As a further non-limiting example, a homing molecule useful in a method of the invention can be a homing peptide or peptidomimetic.

Any of a variety of homing molecules that specifically bind Sigirr/TIR8 (SEQ ID NO: 29) are useful in the methods of the invention including, without limitation, homing peptides or peptidomimetics containing the amino acid sequence CKRAVR (SEQ ID NO: 7) or conservative variants or peptidomimetics thereof; peptides and peptidomimetics containing the amino acid sequence CRNSWKPNC (SEQ ID NO: 8) or conservative variants or peptidomimetics thereof; and peptides and peptidomimetics containing the amino acid sequence RGSSS (SEQ ID NO: 9) or conservative variants or peptidomimetics thereof. Such homing peptides and peptidomimetics can be, without limitation, linear, cyclic, or otherwise conformationally constrained. Furthermore, any of a variety of moieties can be useful in the methods of the invention which rely on a homing molecule that specifically binds Sigirr/TIR8 (SEQ ID NO: 29). Such moieties include, without limitation, detectable moieties such as radionuclides and fluorescent molecules, and therapeutic agents such as angiogenic agents, anti-thrombotic agents, anti-inflammatory agents, immunosuppressive agents, anti-arrhythmic agents, tumor necrosis factor inhibitors, endothelin inhibitors, angiotensin-converting enzyme inhibitors, calcium antagonists, antibiotic agents, antiviral agents and viral vectors.

The present invention further provides methods of directing a moiety to heart vasculature in a subject by administering to the subject a conjugate containing a moiety linked to a homing molecule that selectively homes to heart vasculature and specifically binds SEQ ID NO: 33, thereby directing the moiety to heart vasculature. As non-limiting examples, the methods of the invention can be practiced with a homing molecule that homes to the heart in vivo with a selectivity of at least 5-fold relative to non-recombinant phage, or with a homing molecule which is a peptide or peptidomimetic. In one embodiment, a method of the invention is practiced with a conjugate containing a homing peptide or peptidomimetic that includes the amino acid sequence CRSTRANPC (SEQ ID NO: 11) or a conservative variant or peptidomimetic thereof. In such a method, the homing peptide or peptidomimetic containing the amino acid sequence CRSTRANPC (SEQ ID NO: 11) can optionally be conformationally constrained. Any of a variety of moieties can be useful in the methods of the invention, including, without limitation, detectable moieties, such as radionuclides and fluorescent molecules, and therapeutic agents such as angiogenic agents, anti-thrombotic agents, anti-inflammatory agents, immunosuppressive agents, anti-arrhythmic agents, tumor necrosis factor inhibitors, endothelin inhibitors, angiotensin-converting enzyme inhibitors, calcium antagonists, antibiotic agents, antiviral agents and viral vectors.

Further provided herein are methods of directing a moiety to heart vasculature in a subject by administering to the subject a conjugate containing a moiety linked to a homing molecule that selectively homes to heart vasculature and specifically binds bc10 (SEQ ID NO: 35), thereby directing the moiety to heart vasculature. A homing molecule useful in the invention can home to the heart in vivo with a selectivity, for example, of at least 5-fold relative to non-recombinant phage and can be a peptide or peptidomimetic. Any of a variety of homing molecules that specifically bind bc10 (SEQ ID NO: 35) can be useful in the methods of the invention. Such homing molecules include, but are not limited to, homing peptides and peptidomimetics containing the amino acid sequence CPKTRRVPC (SEQ ID NO: 12) or a conservative variant or peptidomimetic thereof, and homing peptides and peptidomimetics that contain the amino acid sequence CSGMARTKC (SEQ ID NO: 13) or a conservative variant or peptidomimetic thereof. Such homing peptides and peptidomimetics can be useful as linear, cyclic or otherwise conformationally constrained structures. The methods of the invention which rely on a conjugate that incorporates a homing molecule which specifically binds bc10 (SEQ ID NO: 35) can be practiced with any of a variety of moieties. Useful moieties include, without limitation, detectable moieties such as radionuclides and fluorescent molecules as well as therapeutic agents such as angiogenic agents, anti-thrombotic agents, anti-inflammatory agents, immunosuppressive agents, anti-arrhythmic agents, tumor necrosis factor inhibitors, endothelin inhibitors, angiotensin-converting enzyme inhibitors, calcium antagonists, antibiotic agents, antiviral agents and viral vectors.

The present invention also provides a method of treating a cardiovascular disease in a subject by administering to the subject a conjugate containing a therapeutic agent linked to a homing molecule that selectively homes to heart vasculature and specifically binds HLP/CRIP2 (SEQ ID NO: 25). In such a method of the invention, a homing molecule can home to the heart in vivo with a selectivity, for example, of at least 5-fold relative to non-recombinant phage, and can be, for example, a homing peptide or peptidomimetic. Any of a variety of homing molecules that specifically bind HLP/CRIP2 (SEQ ID NO: 25) can be useful in a method of the invention including, without limitation, homing peptides or peptidomimetics containing the amino acid sequence CRPPR (SEQ ID NO: 1) or conservative variants or peptidomimetics thereof, and homing peptides or peptidomimetics containing the amino acid sequence CGRKSKTVC (SEQ ID NO: 2) or conservative variants or peptidomimetics thereof. A homing peptide or peptidomimetic useful in the invention may optionally be conformationally constrained. Any of a variety of therapeutic agents can be useful for treating a cardiovascular disease according to a method of the invention, including, but not limited to, angiogenic agents, anti-thrombotic agents, anti-inflammatory agents, immunosuppressive agents, anti-arrhythmic agents, tumor necrosis factor inhibitors, endothelin inhibitors, angiotensin-converting enzyme inhibitors, calcium antagonists, antibiotic agents, antiviral agents and viral vectors.

Further provided herein are methods of treating a cardiovascular disease in a subject by administering to the subject a conjugate containing a therapeutic agent linked to a homing molecule that selectively homes to heart vasculature and specifically binds SEQ ID NO: 27. A homing molecule useful for treating a cardiovascular disease can home to the heart in vivo with a selectivity, for example, of at least 5-fold relative to non-recombinant phage. Any of a variety of homing molecules that specifically bind SEQ ID NO: 27 can be useful in a method of the invention, including homing peptides or peptidomimetics such as those containing the amino acid sequence CARPAR (SEQ ID NO: 5) or conservative variants or peptidomimetics thereof, and those containing the amino acid sequence CPKRPR (SEQ ID NO: 6) or conservative variants or peptidomimetics thereof. Any of a variety of therapeutic agents can be useful for treating a cardiovascular disease according to a method of the invention. Such therapeutic agents include, but are not limited to, angiogenic agents, anti-thrombotic agents, anti-inflammatory agents, immunosuppressive agents, anti-arrhythmic agents, tumor necrosis factor inhibitors, endothelin inhibitors, angiotensin-converting enzyme inhibitors, calcium antagonists, antibiotic agents, antiviral agents and viral vectors.

Also provided herein are methods of treating a cardiovascular disease in a subject by administering to the subject a conjugate which contains a therapeutic agent linked to a homing molecule that selectively homes to heart vasculature and specifically binds Sigirr/TIR8 (SEQ ID NO: 29). In a method of the invention, the homing molecule can home to the heart in vivo with a selectivity of, for example, at least 5-fold relative to non-recombinant phage. Any of a variety of homing molecules that specifically bind Sigirr/TIR8 (SEQ ID NO: 29) are useful in the methods of the invention including, but not limited to, homing peptides and peptidomimetics. Such homing peptides or peptidomimetics can be, for example, homing peptides and peptidomimetics having the amino acid sequence CKRAVR (SEQ ID NO: 7) or conservative variants or peptidomimetics thereof; homing peptides and peptidomimetics having the amino acid sequence CRNSWKPNC (SEQ ID NO: 8) or conservative variants or peptidomimetics thereof; or homing peptides and peptidomimetics having peptides and peptidomimetics having the amino acid sequence RGSSS (SEQ ID NO: 9) or conservative variants or peptidomimetics thereof. Homing peptides and peptidomimetics useful in a method of the invention for treating a cardiovascular disease can be, for example, linear, cyclic, or otherwise conformationally constrained. Any of a variety of therapeutic agents can be linked to the homing molecule that specifically binds Sigirr/TIR8 (SEQ ID NO: 29) in a method of the invention; such therapeutic agents include, without limitation, angiogenic agents, anti-thrombotic agents, anti-inflammatory agents, immunosuppressive agents, anti-arrhythmic agents, tumor necrosis factor inhibitors, endothelin inhibitors, angiotensin-converting enzyme inhibitors, calcium antagonists, antibiotic agents, antiviral agents and viral vectors.

The present invention further provides methods of treating a cardiovascular disease in a subject by administering to the subject a conjugate containing a therapeutic agent linked to a homing molecule that selectively homes to heart vasculature and specifically binds SEQ ID NO: 33. As non-limiting examples, such methods can be practiced with a homing molecule that homes to the heart in vivo with a selectivity of at least 5-fold relative to non-recombinant phage, or with a homing molecule which is a peptide or peptidomimetic. In particular embodiments, a method of the invention for treating a cardiovascular disease is practiced using a homing peptide or peptidomimetic which includes the amino acid sequence CRSTRANPC (SEQ ID NO: 11) or a conservative variant or peptidomimetic thereof. Therapeutic agents which can be useful in a method of the invention include, without limitation, angiogenic agents, anti-thrombotic agents, anti-inflammatory agents, immunosuppressive agents, anti-arrhythmic agents, tumor necrosis factor inhibitors, endothelin inhibitors, angiotensin-converting enzyme inhibitors, calcium antagonists, antibiotic agents, antiviral agents and viral vectors.

The present invention further provides methods of treating a cardiovascular disease in a subject by administering to the subject a conjugate containing a therapeutic agent linked to a homing molecule that selectively homes to heart vasculature and specifically binds murine bladder cancer-associated protein homolog (bc10; SEQ ID NO: 35). Homing molecules useful in the invention include, but are not limited to, those which can home to the heart in vivo with a selectivity of at least 5-fold relative to non-recombinant phage such as, without limitation, homing peptides and peptidomimetics. Any of a variety of homing molecules that specifically bind bc10 (SEQ ID NO: 35) can be useful for treating a cardiovascular disease according to a method of the invention. Such homing molecules include, but are not limited to, homing peptides and peptidomimetics containing the amino acid sequence CPKTRRVPC (SEQ ID NO: 12) or a conservative variant or peptidomimetic thereof, and homing peptides and peptidomimetics containing the amino acid sequence CSGMARTKC (SEQ ID NO: 13) or a conservative variant or peptidomimetic thereof. As discussed above, such homing peptides and peptidomimetics optionally can be conformationally constrained. Therapeutic agents suitable for use in a method of the invention include, but are not limited to, angiogenic agents, anti-thrombotic agents, anti-inflammatory agents, immunosuppressive agents, anti-arrhythmic agents, tumor necrosis factor inhibitors, endothelin inhibitors, angiotensin-converting enzyme inhibitors, calcium antagonists, antibiotic agents, antiviral agents and viral vectors.

As discussed further below, the conjugates and methods of the invention can be useful for treating any of a variety of cardiopathies and cardiovascular diseases. Such cardiopathies and cardiovascular diseases include, but are not limited to, coronary artery disease (CAD); atherosclerosis; thrombosis; restenosis; vasculitis including autoimmune and viral vasculitis such as polyarteritis nodosa, Churg-Strass syndrome, Takayasu's arteritis, Kawasaki Disease and Rickettsial vasculitis; atherosclerotic aneurisms; myocardial hypertrophy; congenital heart diseases (CHD); ischemic heart disease and anginas; acquired valvular/endocardial diseases; primary myocardial diseases including myocarditis; arrhythmias; and transplant rejection. Cardiopathies and cardiovascular diseases to be treated according to a method of the invention further include, but are not limited to, metabolic myocardial diseases and myocardiomyopathies such as congestive, hypertrophic and restrictive cardiomyopathies, and heart transplants. A therapeutic agent linked to a homing molecule of the invention will concentrate in the heart blood vessels and can further accumulate in the myocardium. Thus, the conjugates and methods of the invention are useful for treating these and other disorders of heart blood vessels or myocardium.

Angiogenesis-based therapy using a therapeutic agent that stimulates new blood vessel formation (angiogenesis) can be useful for treating a cardiovascular disease according to a method of the invention. Angiogenic agents can be useful for treating, without limitation, ischemic heart disease including chronic myocardial ischemia and acute myocardial infarction (Ware and Simons, *Nature Med.* 3:158-164 (1997)). Many patients with severe vascular disease that are not candidates for mechanical revascularization can benefit from angiogenesis-based therapy, including those patients with occlusion of vessels too small to be bypassed, those without conduits and those who are not surgical candidates because of concomitant disease. It has been calculated that 314 million disease cases in the U.S. and European Union may benefit from angiogenesis-based therapy (Miller and Abrams, *Gen. Engin. News* 18:1 (1998)). Thus, a molecule that selectively homes to heart vasculature can be linked to an angiogenic agent and delivered to a patient, thereby stimulating angiogenesis and alleviating the cardiovascular disease.

An angiogenic agent useful in the invention also can be a naturally occurring angiogenic growth factor or cytokine that induces or promotes angiogenesis by stimulating endothelial cell growth or migration. Angiogenic agents useful in the invention encompass, without limitation, isoforms of vascular endothelial growth factor (VEGF) such as VEGF-A, including $VEGF_{121}$ and $VEGF_{165}$, and forms of fibroblast growth factor including, but not limited to, forms of FGF-1 and FGF-2 (Ruel and Selike, *Sem. Thor. Cardiovasc. Surg.* 15:222-235 (2003). As discussed further below, angiogenic agents and other therapeutic agents of the invention can be delivered as protein therapeutics or as nucleic acid therapeutic via gene therapy vectors.

VEGF-A, which is additionally known as vascular permeability factor (VPF), also can be useful in the invention (Dvorak et al., *Am. J. Pathol.* 146:1029-1039 (1995); Thomas et al., *J. Biol. Chem.* 271:603-606 (1996); Olofsson et al., *Proc. Natl. Acad. Sci., USA* 93:2576-2581 (1996); Joukov et al., *EMBO J.* 15:290-298 (1996); and Harada et al., *Am. J. Physiol.* 270:H1791-H1802 (1996)). Other VEGFs (B, C and D) have angiogenic activity without effecting endothelial permeability. Transfer of plasmid DNA encoding VEGF has been shown to result in significant reduction in thrombus formation and intimal thickening following stent implantation (*J. Am. Coll. Cardiol.* 29:1371-1379 (1997)). Angiogenic agents useful in the invention include, without limitation, a recombinant 165 kDa isoform of VEGF, designated rhVEGF, developed by Genentech; a nucleic acid molecule encoding the 121 amino acid isoform of VEGF (BIOBYPASS™; GenVec/Parke Davis); and nucleic acids encoding VEGF-B, VEGF-C and VEGF-D. See, for example, Miller and Abrams, supra, 1998.

An angiogenic agent useful in the invention also can be a member of the fibroblast growth factor (FGF) family such as FGF-1 (acidic), FGF-2 (basic), FGF-4 or FGF-5 (Slavin et al., *Cell Biol. Int.* 19:431-444 (1995); Folkman and Shing, *J. Biol. Chem.* 267:10931-10934 (1992)). An FGF to be linked to a molecule that selectively homes to heart vasculature in a conjugate or method of the invention can be, for example, FIBLAST® (trafermin), a recombinant form of FGF-2 being developed by Scios, Inc. (Mountain View, Calif.) and Wyeth Ayerst Laboratories (Radnor, Pa.), or GENERX™, or an adenoviral gene therapy vector encoding FGF-4 developed by Collateral Therapeutics (San Diego, Calif.) and Schering AG (Miller and Abrams, supra, 1998).

An angiogenic agent useful in the invention also can be angiopoietin-1, an angiogenic factor that signals through the endothelial cell-specific Tie2 receptor tyrosine kinase (Davis et al., *Cell* 87:1161-1169 (1996)). Like VEGF, angiopoietin-1 is essential for normal vascular development, and its overexpression leads to increased angiogenesis (Suri et al., *Cell* 87:1171-1180 (1996)).

A therapeutic agent useful in a conjugate or method of the invention also can be an anti-thrombotic agent that prevents the formation of a thrombus, which is an aggregation of blood factors, primarily platelets and fibrin with entrapment of cellular elements. Thrombus formation is stimulated by the presence of atheromatous plaques and is the main cause of episodes of acute ischemic heart disease. An anti-thrombotic agent useful in the invention can be, without limitation, an inhibitor of the IIb/IIIa integrin (Coller, *Circulation* 92:2373 (1995); a tissue factor inhibitor; a plasminogen activator or an anti-thrombin agent.

An immunosuppressive agent also can be useful in the conjugates and methods of the invention, for example, for treating a heart transplant recipient. It is understood that an immunosuppressive agent can be useful in chronic prophylactic treatment, which organ transplant recipients typically require for their entire lives, or for treating patients exhibiting one or more symptoms consistent with transplant rejection, or for use as a rescue agent in severe rejection. Immunosuppressive agents useful in the conjugates and methods of the invention encompass, without limitation, steroids including corticosteroids and prednisolone; calcineurin inhibitors such as PROGRAF®, NEORAL®, RAPAMUNE®, cyclosporine A and other cyclosporines; anti-proliferative agents including CELLCEPT®, IMURAN® (azathioprine) and CERTICAN™ (everolimus); and therapeutic monoclonal antibodies such as OKT3, ATGAM, thymoglobulin and anti-thymocyte globulins, dicluzimab and basiliximab. These and other immunosuppressive agents can be useful alone or in combination with another immunosuppressive agent or other therapeutic agent in the conjugates and methods of the invention.

Anti-inflammatory agents, which are molecules that reduce one or more symptoms of inflammation, also are useful in the conjugates and methods of the invention. Such anti-inflammatory agents include, without limitation, steroids including corticosteroids and immunoglobulins as well as cyclooxygenase inhibitors and other non-steroidal anti-inflammatory drugs. In one embodiment, the anti-inflammatory agent is AGI-1067, a cholesterol-lowering anti-inflammatory agent (AtheroGenics; Atlanta, Ala.).

An anti-arrhythmic agent also can be useful in the conjugates and methods of the invention, for example, for treating a cardiac arrhythmia, which is a disorder in which the normal periodicity and regular electromechanical activity of the heart are disrupted. Thus, in a conjugate or method of the invention, a therapeutic agent can be an antiarrhythmic agent such as a local anesthetic (class I agent), sympathetic antagonist (class II agent), antifibrillatory agent (class III agent), calcium channel agent (class IV agent) or anion antagonist (class V agent) as described, for example, in Vukmir, *Am. J. Emer. Med.* 13:459-470 (1995); Grant, *PACE* 20:432-444 (1997); Mann, *Curr. Med. Res. Opin.* 13:325-343 (1995); or Lipka et al., *Am. Heart J.* 130:632-640 (1995). An antiarrhythmic agent that is a local anesthetic acts as a fast sodium channel antagonist; such an antiarrhythmic agent can be, without limitation, procainamide, quinidine or disopyramide; lidocaine, phenytoin, tocainide or mexiletine; or encainide; flecainide; lorcainide; propafenone (III) or moricizine (Vukmir, supra, 1995). An antiarrhythmic agent also can be sympathetic antagonist (β-adrenergic antagonist) such as, without limitation, propranolol, esmolol, metoprolol, atenelal, acebutolol, or an antifibrillatory agent that acts by prolonging action potential duration (APD), for example, bretylium, amiodarone, sotalol (II) or N-acetylprocainamide (Vukmir, supra, 1995). Additional antiarrhythmic agents that can be useful as therapeutic agents in the conjugates or methods of the invention include, but are not limited to, calcium channel agents such as verapamil, diltiazem, and bepridil, and anion antagonists such as alinidine (Vukmir, supra, 1995). The skilled person understands that these and other antiarrhythmic drugs known in the art can be therapeutic agents which are useful for treating cardiac arrhythmias in a conjugate or method of the invention.

Calcium antagonists, also known as calcium channel blockers (CBBs), have beneficial effects in many cardiovascular diseases, acting as potent inhibitors of smooth muscle cell proliferation and migration. Additional properties that make these therapeutic agents useful in treating atherosclerosis and other cardiovascular disease include their ability to inhibit calcium influx into the vascular wall; reduce extracellular matrix synthesis; promote uptake and breakdown of low-density lipoproteins; protect lipoproteins from oxidative modification; maintain endothelial cell function; and inhibit platelet activation. Among the calcium antagonists, amlodipine is a therapeutic agent with vascular selectivity (Marche et al., *Int. J. Cardiol.* 62 (Suppl.): S17-S22 (1997); Schachter, *Int. J. Cardiol.* 62 (Suppl.): S85-S90 (1997)). Additional calcium antagonists which can serve as therapeutic agents useful in the invention include, without limitation, nicardipine, nifedipine, propanolol, isosorbide dinitrate, diltiazem, and isradipine (Nayler (Ed.) *Calcium Antagonists* pages 157-260 London: Academic Press (1988); Schachter, *Int. J. Cardiol.* 62 (Suppl.): S9-S15 (1997)). Therapeutic agents that elevate cAMP or cGMP content reduce vascular smooth muscle cell responsiveness or proliferation and also can be useful when linked to a molecule that selectively homes to heart vasculature. Such therapeutic agents include, yet are not limited to, the cAMP phosphodiesterase inhibitor cilostasol and endothelium-derived nitric oxide (NO) or NO-generating vasodilators. See, for example, Takahashi et al., *J. Cardiovas. Pharm.* 20:900-906 (1992); and Cornwell et al., *Am. J. Physiol.* 267:C1405-1413 (1994).

A therapeutic agent useful in the invention also can be an antiviral or antibiotic agent. Numerous studies have reported an association of endocarditis, atherosclerosis and restenosis with particular bacterial and viral infections, especially cytomegalovirus and *Chlamydia pneumoniae* (Cheng and Rivera, *Annals of Pharmacotherapy* 32:1310-1316 (1998)). For prophylactic use in a heart transplant or other patient at high risk of developing atherosclerosis, the patient can be administered a conjugate containing a molecule that selectively homes to heart vasculature linked to an antiviral agent such as ganciclovir. Additional antiviral agents that can be included in a conjugate or method of the invention include, without limitation, Ribavirin (Virazole, 1-β-D-ribofuranosyl-1,2,4-triazole-3-carboximide) and recombinant human leukocyte IFN-α A/D (Matsumori et al., *Circulation* 71:834-839 (1985); Matsumori et al., *J. Am. Coll. Cardiol.* 9:1320-1325 (1987)).

The conjugates and methods also can be useful for treating atherosclerosis, which, in conjunction with its consequences, constitutes the most common and important cause of disease and death in the western world. Like other occlusive vascular disease, atherosclerosis is characterized by the abnormal accumulation of lipid, inflammatory cells, vascular smooth muscle cells, and extracellular matrix proteins within the intimal space between the endothelial lining and the medial layer (plaque formation). In particular, damage to the endothelium allows entry of cholesterol-rich low-density lipoproteins (LDLs) into the intima. Lipid is taken up by macrophages in the intima, with excessive lipid accumulating in the intimal macrophages through a receptor-independent pathway that takes up oxidized LDL. Macrophages release lipid into the intima and secrete cytokines that stimulate proliferation. Intimal cells with features of myofibroblasts secrete collagen, causing the plaque to become fibrotic in some cases. As the lesion develops, there is pressure atrophy of the media, and the elastic lamina is disrupted. Further collagen deposition forms a dense fibrous cap to the plaque (fibrolipid plaque), which contains free lipid as well as lipid in macrophages. The fragile endothelium of the plaques often ulcerates, allowing platelet aggregation and thrombosis. Growth factors such as platelet-derived growth factor cause further plaque development by stimulating cell proliferation.

Increased proliferation of intimal smooth muscle cells causes myointimal hyperplasia and luminal narrowing. The abnormal cell proliferation which plays a role in neointima formation can result from specific growth factors such as platelet derived growth factor (PDGF), transforming growth factor-β1 (TGF-β1) or angiotensin II (Ross, *Annu. Rev. Physiol.* 57:791 (1995); Schwartz et al., *Circ. Res.* 77:445 (1995); and Gibbons and Dzau, *New Eng. J. Med.* 330:1431 (1994)).

A therapeutic agent useful in the conjugates and methods of the invention for treating a cardiovascular disease such as intimal hyperplasia following angioplasty can be a growth inhibitory agent that reduces or prevents vascular disease by limiting neointimal smooth muscle cell proliferation. For example, a herpes virus thymidine kinase (tk) gene and systemic ganciclovir can be used to kill proliferating cells and limit neointimal formation. In one study, porcine iliofemoral arteries were infected with an adenoviral vector encoding tk and, after exposure to ganciclovir, the neointimal thickening seen following balloon injury was reduced by 50-87% (Ohno et al., *Science* 265:781-784 (1994); see, also, Guzman et al., *Proc. Natl. Acad. Sci., USA* 91:10732-10736 (1994); Chang et al., *Mol. Med.* 1:172-181 (1995); and Simari et al., *Circulation* 92:1-501 (1995)). Thus, a therapeutic agent useful in the invention can be a cytostatic agent such as, without limitation, thymidine kinase combined with ganciclovir.

Additional therapeutic agents for limiting neointimal formation also are known in art and include genes that inhibit cell cycle proteins and proto-oncogenes (Simari and Nabel, *Semin. Intervent. Cardiol.* 1:77-83 (1996)). Such therapeutic agents include, without limitation, tumor suppressor genes such as p53 and retinoblastoma as well as genes encoding bcl-x, mutant forms of ras and nitric oxide synthetase. As a non-limiting example, the retinoblastoma gene product (Rb) inhibits cell proliferation in many mammalian cell types, and transfer of a recombinant adenovirus encoding active Rb into injured rat carotid and porcine iliac arteries decreases neointimal formation (Chang et al., *Science* 267:518-522 (1994)). Gene transfer of p53 similarly has been shown to inhibit vascular smooth muscle cell proliferation (Yonemitsu et al., *Circ. Res.* 82:147-156 (1998); see, also, Muller, *Prog. Cardiovas. Dis.* 40:117-128 (1997)). Direct gene transfer of dominant negative ras variants also inhibited intima development following balloon injury in rat carotid and porcine iliofemoral models (Chang et al., *J. Clin. Invest.* 96:2260-2268 (1995)). In a rat carotid injury model, gene transfer of nitric oxide synthetase also limited intimal formation (von der Leyen et al., *Proc. Natl. Acad. Sci., USA* 92:1137-1141 (1995). One skilled in the art understands that a cytostatic agents also can be useful as a therapeutic agent in a conjugate or method of the invention.

A decoy or antisense oligonucleotide against a cellular target such as E2F or one of various cyclins also can be a therapeutic agent useful for limiting neointima proliferation in a method of the invention (Morishita et al., *Circ. Res.* 82:1023-1028 (1998); and Mann et al., *Circulation* 96:1-4 1997)). The growth arrest homeobox gene gax, which is rapidly downregulated in vascular smooth muscle cells after vascular injury in vivo also can be a therapeutic agent useful for inhibiting intimal hyperplasia (Smith et al., *Genes Dev.* 11:1674-1689 (1997); and Skopicki et al., *Circ. Res.* 80:452-462 (1997)). Additional therapeutic agents that can be useful in limiting intimal hyperplasia in a conjugate or method of the invention also are known in the art (see, for example, Laitinen and Ylä-Herttuala, *Current Opin. Lipid.* 9:465-469 (1998).

A conjugate or method of the invention also can be useful for treating restenosis, which is the re-narrowing of lumen dimensions that may follow angioplasty, a procedure in which a balloon is inserted into an occluded vessel and then inflated to dilate the area of narrowing. Restenosis occurs in about 30 to 50% of cases over a time course of three to six months and involves cellular hyperplasia within the neointima, the organization of thrombus within the vessel wall, and shrinkage of overall vessel dimensions. Angioplasty denudes the vessel of endothelial cells that would normally generate paracrine inhibitors of vascular smooth muscle migration and proliferation.

Nitric oxide deficiency is associated with impaired vasorelaxation and increased adhesiveness, predisposing vascular tissue to the formation of atherosclerotic lesions (Gibbons and Dzau, *Science* 272:689-693 (1996)). Therapeutic agents useful in the conjugates and methods of the invention include, without limitation, endothelial cell-type nitric oxide (NO) synthase agents, which are agents that enhance nitric oxide synthase activity. Such therapeutic agents which enhance nitric oxide (NO) activity encompass, without limitation, nitric oxide synthase genes and nitric oxide-donor drugs. Transfection of a nitric oxide synthase gene into the vessel wall after balloon injury in a rat model of neointima formation resulted in generation of nitric oxide and a substantial inhibition of cell proliferation, migration and matrix production required for neointima formation (von der Leyen et al., supra, 1995). Clinical studies also indicate that a nitric oxide-donor drug can be used to augment nitric oxide activity and treat restenosis (Ferguson, *Circulation* 90:4 (1994)).

The conjugates and methods of the invention also can be used to treat congestive heart failure (CHF), a disorder affecting nearly five million people in the United States alone. Congestive heart failure results when the heart is damaged from atherosclerosis or other conditions such as high blood pressure, myocardial infarction or defective heart valves. The failing heart works inefficiently, causing fluid retention, shortness of breath and fatigue. Thus, for treatment of congestive heart failure, a molecule that selectively homes to heart vasculature can be linked to a therapeutic agent such as, without limitation, a TNF inhibitor such as the recombinant soluble TNF decoy receptor, EMBREL™ (Immunex Corp.; Seattle, Wash.).

Endothelins, which are polypeptides that constrict blood vessels, also are elevated in congestive heart failure. Thus, a molecule of the invention which selectively homes to heart vasculature can be linked to a therapeutic agent that is an endothelin inhibitor, for example, the small molecule drug, TBC11251. This drug, which was developed by Texas Biotechnology Corp., inhibits endothelin A-receptor binding and promotes relaxation of smooth muscle cells. TBC11251 has resulted in significant improvement in patients with moderate to severe congestive heart failure (Potera, *Gen. Engin. News* 18:12 (1998)).

A therapeutic agent for use in a conjugate or method of the invention also can be a replacement gene therapy vector for an inherited heart disease. Such an inherited disease can be, for example, an inherited disease of the myocardium such as X-linked dilated cardiomyopathy, hypertrophic cardiomyopathy, Long QT Syndrome or another disease for which the disease-causing mutation has been identified (Bowles et al., *Cardiovas. Res.* 35:422-430 (1997)). In one embodiment, a conjugate or method of the invention is practiced with a molecule that selectively homes to heart vasculature linked to an adenoviral gene therapy vector containing a nucleic acid molecule encoding a desired replacement gene product.

A therapeutic agent can be delivered, for example, as a protein as described in Harada et al., *J. Clin. Invest.* 94:623-630 (1994). Microspheres, for example, microspheres of 7 μm diameter to which an angiogenic factor such as bFGF is reversibly adsorbed through $SO_3$ residues, also can be linked to a molecule that selectively homes to heart vasculature in order to selectively deliver the microspheres for treatment of a cardiovascular disease. Such microspheres lodge in the peripheral microcirculation without interfering with total flow and are slowly released over a period of a week (Arras et al., *Nature Biotech.* 16:159-162 (1998); see, also, Tice and Staas, *Nature Biotech.* 16:134 (1998)). A single injection of a biodegradable microsphere can be used to deliver an angiogenic or other therapeutic agent, which is released over one or several months following the injection, with the rate and duration of drug release controlled by factors such as the polymer type and microparticle size (Maulding, *Controlled Release* 6:167-176 (1987); Tice and Tabibi, pages 315-339 in Kydonieus (Ed.), *Treatise on Controlled Drug Delivery* Marcel Dekker, New York (1992)). A gene therapy vector also can be linked to a homing molecule that selectively homes to heart vasculature to deliver a nucleic acid molecule encoding an angiogenic or other therapeutic agent (see, for example, Isner et al., *Lancet* 348:370-374 (1996); Giordano et al., *Nature Med.* 2:534-539 (1996))

A variety of suitable gene therapy methodologies are known in the art for treating a cardiopathy or cardiovascular disease in a method of the invention (see, for example, Li et al., *Cardiol.* 41:39-46 (1997)). As non-limiting examples, viral vectors, including retroviral and adenoviral vectors, can be useful for gene delivery when linked to a molecule that selectively homes to heart vasculature. Such a gene therapy vector can include a nucleic acid molecule encoding a therapeutic agent such as, without limitation, an angiogenic agent such as a VEGF or FGF. Gene therapy with forms of VEGF, FGF and other angiogenic agents are well known in the art as described, for example, in Sylven, *Drugs of Today* 38:819-827 (2002); Symes, *J. Card. Surg.* 15:283-290 (2000); and Grines et al., *Am. J. Cardiol.* 92 (Suppl.): 24N-31N (2003). Angiogenic gene therapy with a replication-incompetent, serotype 5 adenovirus in which the E1A and E1B genes have been replaced by the human fibroblast growth factor-4 (FGF-4) gene under control of a cytomegalovirus promoter, denoted Ad5FGF-4, has had beneficial effects in placebo-controlled trials in humans with chronic stable angina (Grines et al., supra, 2003). See, also, Simari and Nabel, supra, 1996; and Indolfi and Chiariello, *Cardiologia* 43:365-373 (1998)). Thus, in one embodiment, a method of the invention relies on a replication deficient recombinant adenoviral vector which expresses a therapeutic gene product.

In view of the above, it is understood that a variety of therapeutic agents are useful for treating a cardiovascular disease according to a method of the invention. Useful therapeutic agents encompass, yet are not limited to, angiogenic agents, anti-thrombotic agents, anti-inflammatory agents, immunosuppressive agents, anti-arrhythmic agents, tumor necrosis factor inhibitors, endothelin inhibitors, angiotensin-converting enzyme inhibitors, calcium antagonists, antibiotic agents, antiviral agents and viral vectors. One skilled in the art understands that these as well as additional known or other therapeutic agents can be selectively directed to heart vasculature when incorporated into a conjugate or method of the invention. Furthermore, one skilled in the art of medicinal cardiology understands that these and other therapeutic agents can be used separately or together in the conjugates and methods of the invention. It further is understood that a conjugate of the invention can contain one or more of such therapeutic agents and that additional components can optionally be included in a conjugate of the invention. As an example, in some cases, it can be desirable to utilize an oligopeptide spacer between the homing molecule and the therapeutic agent. See, for example, Fitzpatrick and Garnett, *Anticancer Drug Design* 10:1-9 (1995).

It is further understood that a variety of routes of administration are useful in the methods of the invention. Such routes encompass systemic and local administration and include, without limitation, oral administration, intravenous injection, intraperitoneal injection, intramuscular injection, subcutaneous injection, transdermal diffusion or electrophoresis, local injection, and extended release delivery devices including locally implanted extended release devices such as bioerodible or reservoir-based implants.

The present invention further provides methods of imaging heart vasculature in a subject by administering to the subject a conjugate containing a detectable moiety linked to a homing molecule that selectively homes to heart vasculature and specifically binds HLP/CRIP2 (SEQ ID NO: 25); and detecting the conjugate. In the methods of the invention for imaging heart vasculature, a homing molecule can home to the heart in vivo with a selectivity, for example, of at least 5-fold relative to non-recombinant phage, and can be, for example, a homing peptide or peptidomimetic. A variety of homing molecules that specifically bind HLP/CRIP2 (SEQ ID NO: 25) can be useful for imaging heart vasculature according to a method of the invention. Such homing molecules encompass, without limitation, homing peptides or peptidomimetics containing the amino acid sequence CRPPR (SEQ ID NO: 1) or conservative variants or peptidomimetics thereof, and homing peptides or peptidomimetics containing the amino acid sequence CGRKSKTVC (SEQ ID NO: 2) or conservative variants or peptidomimetics thereof. A variety of detectable moieties are useful in the above methods of the invention, including, for example, radionuclides and paramagnetic ions.

Further provided herein are methods of imaging heart vasculature in a subject by administering to the subject a conjugate containing a detectable moiety linked to a homing molecule that selectively homes to heart vasculature and that specifically binds SEQ ID NO: 27; and detecting the conjugate. In the methods of the invention for imaging heart vasculature, a homing molecule can home to the heart in vivo with a selectivity, for example, of at least 5-fold relative to non-recombinant phage. A variety of homing molecules that specifically bind SEQ ID NO: 27 can be useful for imaging heart vasculature according to a method of the invention. Such homing molecules encompass, without limitation, homing peptides or peptidomimetics such as those containing the amino acid sequence CARPAR (SEQ ID NO: 5) or conservative variants or peptidomimetics thereof, and those containing the amino acid sequence CPKRPR (SEQ ID NO: 6) or conservative variants or peptidomimetics thereof. A variety of detectable moieties are useful for imaging heart vasculature including, for example, radionuclides and paramagnetic ions.

The present invention additionally provides methods of imaging heart vasculature in a subject by administering to the subject a conjugate which contains a detectable moiety linked to a homing molecule that selectively homes to heart vasculature and specifically binds Sigirr/TIR8 (SEQ ID NO: 29); and detecting the conjugate. In such imaging methods of the invention, the homing molecule can home to the heart in vivo with a selectivity of, for example, at least 5-fold relative to non-recombinant phage. Furthermore, any of a variety of homing molecules that specifically bind Sigirr/TIR8 (SEQ ID NO: 29) are useful for imaging heart vasculature according to a method of the invention; such homing molecules include, without limitation, homing peptides and peptidomimetics having the amino acid sequence CKRAVR (SEQ ID NO: 7) or conservative variants or peptidomimetics thereof, homing peptides and peptidomimetics having the amino acid sequence CRNSWKPNC (SEQ ID NO: 8) or conservative variants or peptidomimetics thereof; and homing peptides and peptidomimetics having the amino acid sequence RGSSS (SEQ ID NO: 9) or conservative variants or peptidomimetics thereof. It is recognized that the homing peptides and peptidomimetics useful in the imaging methods of the invention can be, for example, linear, cyclic, or otherwise conformationally constrained. Detectable moieties useful for imaging include, but are not limited to, radionuclides and paramagnetic ions.

Further provided herein is a method of imaging heart vasculature in a subject by administering to the subject a conjugate containing a detectable moiety linked to a homing molecule that selectively homes to heart vasculature and specifically binds SEQ ID NO: 33; and detecting the conjugate. As non-limiting examples, the imaging methods of the invention can be practiced with a homing molecule that homes to the heart in vivo with a selectivity of at least 5-fold relative to non-recombinant phage, or with a homing molecule which is a peptide or peptidomimetic. Homing molecules useful in the imaging methods of the invention include, without limitation, homing peptides and peptidomimetics such as those having the amino acid sequence CRSTRANPC (SEQ ID NO: 11) or a conservative variant or peptidomimetic thereof. The methods of the invention for imaging heart vasculature can be practiced with any of a variety of detectable moieties including, for example, radionuclides and paramagnetic ions.

Also provided herein is a method of imaging heart vasculature in a subject by administering to the subject a conjugate containing a detectable moiety linked to a homing molecule that selectively homes to heart vasculature and specifically binds murine bladder cancer-associated protein homolog (bc10; SEQ ID NO: 35); and detecting the conjugate. Homing molecules useful for imaging according to a method of the invention include, but are not limited to, those which can home to the heart in vivo with a selectivity of at least 5-fold relative to non-recombinant phage. Any of a variety of homing molecules that specifically bind bc10 (SEQ ID NO: 35) can be useful for imaging heart vasculature according to a method of the invention, including homing peptides and peptidomimetics such as those containing the amino acid sequence CPKTRRVPC (SEQ ID NO: 12) or a conservative variant or peptidomimetic thereof, or those containing the amino acid sequence CSGMARTKC (SEQ ID NO: 13) or a conservative variant or peptidomimetic thereof. Homing peptides and peptidomimetics useful in the invention can be utilized in linear, cyclic or otherwise conformationally constrained form. As indicated above, detectable moieties useful for imaging include, yet are not limited to, radionuclides and paramagnetic ions.

The imaging methods of the invention rely on a detectable moiety. As used herein, the term "detectable moiety" refers to any molecule which can be administered in vivo and subsequently detected. Exemplary detectable moieties useful in the conjugates and imaging methods of the invention include paramagnetic ions, radionuclides and fluorescent molecules. Exemplary radionuclides include indium-111, technetium-99, carbon-11, and carbon-13. Fluorescent molecules include, without limitation, fluorescein, allophycocyanin, phycoerythrin, rhodamine, and Texas red. Where a detectable moiety is a gamma ray emitting radionuclide such as indium-113, indium-115 or technetium-99, the conjugate can be visualized using a solid scintillation detector following administration to the subject.

Also provided herein is a method of isolating one or more homing molecules that selectively homes to heart vasculature by contacting HLP/CRIP2, or a fragment thereof, with a library of molecules under conditions suitable for specific binding of a molecule to HLP/CRIP2; assaying for specific binding; and separating one or more HLP/CRIP2-binding molecules from the library, thereby isolating one or more homing molecules that selectively homes to heart vasculature and specifically binds HLP/CRIP2. Cells that express HLP/CRIP2 on the cell surface as well as purified HLP/CRIP2, or a fragment thereof, can be useful in the screening methods of the invention. As non-limiting examples, native, recombinant, human, murine (SEQ ID NO: 25) and other variants and homologs of HLP/CRIP2, and fragments thereof such as, without limitation, CRPPR (SEQ ID NO: 1) or CGRKSKTVC (SEQ ID NO: 2)-binding fragments of HLP/CRIP2, whether purified or expressed on the surface of a cell, can be useful in the screening methods of the invention. Libraries that can be screened according to a method of the invention include, but are not limited to, libraries of peptides and peptidomimetics, libraries of small molecules, and libraries of antibodies and antigen-binding fragments thereof, including synthetic, single-chain or other antibody libraries. In one embodiment, a method of the invention includes a further step of assaying for localization of one or more of the separated molecules of the library subsequent to intravenous injection. Where a fragment of HLP/CRIP2 is utilized in place of full-length HLP/CRIP2, it is understood that such a fragment can be, without limitation, a fragment which specifically binds SEQ ID NO: 1 or SEQ ID NO: 2.

Any of a variety of HLP/CRIP2 polypeptides can be useful in the methods of the invention for isolating molecules that selectively home to heart vasculature. As used herein, the term "HLP/CRIP2" means a polypeptide which is selectively expressed in heart vasculature and which has at least 60% amino acid identity with SEQ ID NO: 25. In particular embodiments, HLP/CRIP2 has at least 70%, 80%, 90%, 95% or more amino acid identity with SEQ ID NO: 25.

Further provided by the present invention is a method of isolating one or more homing molecules that selectively homes to heart vasculature by contacting receptor clone 9, or a fragment thereof, with a library of molecules under conditions suitable for specific binding of a molecule to receptor clone 9; assaying for specific binding; and separating one or more receptor clone 9-binding molecules from the library, thereby isolating one or more homing molecules that selectively homes to heart vasculature and specifically binds receptor clone 9. The methods of the invention can be practiced with cells that express receptor clone 9 on the cell surface as well as purified receptor clone 9 or a fragment thereof. As non-limiting examples, native, recombinant, human, murine (SEQ ID NO: 27) and other variants and homologs of murine receptor clone 9 (SEQ ID NO: 27), and fragments thereof such as, without limitation, SEQ ID NO: 5 and SEQ ID NO: 6-binding fragments of receptor clone 9, whether purified or expressed on the surface of a cell, can be useful in the screening methods of the invention. Any of a variety of libraries can be screened according to a method of the invention including, but not limited to, those described hereinabove.

As used herein, the term "receptor clone 9" means a polypeptide which is selectively expressed in heart vasculature and which has at least 60% amino acid identity with SEQ ID NO: 27. In particular embodiments, receptor clone 9 has at least 70%, 80%, 90%, 95% or more amino acid identity with SEQ ID NO: 27.

The present invention also provides a method of isolating one or more homing molecules that selectively homes to heart vasculature by contacting Sigirr/TIR8, or a fragment thereof, with a library of molecules under conditions suitable for specific binding of a molecule to Sigirr/TIR8; assaying for specific binding; and separating one or more Sigirr/TIR8-binding molecules from the library, thereby isolating one or more homing molecules that selectively homes to heart vasculature and specifically binds Sigirr/TIR8. Cells that express Sigirr/TIR8 on the cell surface as well as purified Sigirr/TIR8, or a fragment thereof, can be useful in the screening methods of the invention. As non-limiting examples, native, recombinant, human, murine (SEQ ID NO: 29) and other variants and species homologs of Sigirr/TIR8, as well as fragments thereof such, without limitation, SEQ ID NO: 7 or SEQ ID NO: 8-binding fragments, whether purified or expressed on the surface of a cell, can be useful in the screening methods of the invention. It is further understood that, as indicated above, any of a variety of libraries can be useful in the screening methods of the invention.

The term "Sigirr/TIR8," as used herein, means a polypeptide which is selectively expressed in heart vasculature and which has at least 60% amino acid identity with SEQ ID NO: 29. In particular embodiments, Sigirr/TIR8 has at least 70%, 80%, 90%, 95% or more amino acid identity with SEQ ID NO: 29.

Further provided herein is a method of isolating one or more homing molecules that selectively homes to heart vasculature by contacting MpcII-3-related protein, or a fragment thereof, with a library of molecules under conditions suitable for specific binding of a molecule to MpcII-3-related protein; assaying for specific binding; and separating one or more MpcII-3-related protein-binding molecules from the library, thereby isolating one or more homing molecules that selectively homes to heart vasculature and specifically binds MpcII-3-related protein. A screening method of the invention can be practiced, for example, with cells that express MpcII-3-related protein on the cell surface or with purified MpcII-3-related protein or a fragment thereof. As non-limiting examples, native, recombinant, human, murine (SEQ ID NO: 33) and other variants and species homologs of MpcII-3-related protein, as well as fragments of SEQ ID NO: 33 or human or other MpcII-3-related proteins, including, without limitation, CRSTRANPC (SEQ ID NO: 11)-binding fragments, whether purified or expressed on the surface of a cell, can be useful in the screening methods of the invention. The methods of the invention can be used to screen any of a variety of libraries such as, without limitation, libraries of peptides and peptidomimetics, libraries of small molecules, and libraries of antibodies or antigen-binding fragments thereof, including synthetic, single-chain or other antibody libraries.

As used herein, the term "MpcII-3-related protein" means a polypeptide which is selectively expressed in heart vasculature and which has at least 60% amino acid identity with SEQ ID NO: 33. In particular embodiments, a MpcII-3-related protein has at least 70%, 80%, 90%, 95% or more amino acid identity with SEQ ID NO: 33.

The present invention further provides a method of isolating one or more homing molecules that selectively homes to heart vasculature by contacting bc10, or a fragment thereof, with a library of molecules under conditions suitable for specific binding of a molecule to bc10; assaying for specific binding; and separating one or more bc10-binding molecules from the library, thereby isolating one or more homing molecules that selectively homes to heart vasculature and specifically binds bc10. Cells that express bc10 on the cell surface as well as purified bc10, or a fragment of bc10, are useful in the screening methods of the invention. As non-limiting examples, native, recombinant, human, murine (SEQ ID NO: 35) as well as variants and other species homologs of bc10, and fragments thereof, including, without limitation, SEQ ID NO: 12-binding fragments or SEQ ID NO: 13-binding fragments, whether purified or expressed on the surface of a cell, can be useful in the screening methods of the invention. The methods of the invention are useful for screening any of a variety of libraries as discussed above.

The term "bc10," as used herein, means a polypeptide which is selectively expressed in heart vasculature and which has at least 60% amino acid identity with SEQ ID NO: 35. In particular embodiments, bc10 has at least 70%, 80%, 90%, 95% or more amino acid identity with SEQ ID NO: 35.

The present invention further provides a variety of isolated peptides and peptidomimetics, which can be useful, for example, in constructing the conjugates of the invention or, where the peptide itself has biological activity, in unconjugated form as a therapeutic for treating any cardiovascular disease or cardiomyopathy as described above. Other homing peptides with biological activity are known in the art as described, for example, in Ruoslahti, *Nat. Rev. Cancer* 2:83-90 (2002), and Laakkonen et al., *Proc. Natl. Acad. Sci. USA* 101:9381-9386 (2004). As one example, the present invention provides an isolated peptide or peptidomimetic which has a length of less than 60 residues and includes the amino acid sequence CRPPR (SEQ ID NO: 1) or a peptidomimetic thereof. In one embodiment, the invention provides an isolated peptide which has a length of less than 60 residues and includes the amino acid sequence CRPPR (SEQ ID NO: 1). An isolated peptide or peptidomimetic of the invention which includes the amino acid sequence CRPPR (SEQ ID NO: 1) can have, for example, a length of less than 40 residues or a length of less than 20 residues.

The invention further provides an isolated peptide or peptidomimetic which includes the amino acid sequence GRKSKTV (SEQ ID NO: 14) or a peptidomimetic thereof. In one embodiment, the invention provides an isolated peptide which includes the amino acid sequence GRKSKTV (SEQ ID NO: 14). An isolated peptide or peptidomimetic of the invention can be, for example, conformationally constrained or can include the amino acid sequence CGRKSKTVC (SEQ ID NO: 2). In further embodiments, an isolated peptide or peptidomimetic which includes the amino acid sequence GRKSKTV (SEQ ID NO: 14) or a peptidomimetic thereof has a length of less than 100 residues, a length of less than 60 residues or a length of less than 20 residues. In yet a further embodiment, the invention provides an isolated peptide or peptidomimetic which includes the amino acid sequence CXGRKSKTVZC (SEQ ID NO: 15) or a peptidomimetic thereof, where X=0 to 20 independently selected residues and Z=0 to 20 independently selected residues.

The present invention additionally provides an isolated peptide or peptidomimetic which has a length of less than 150 residues and includes the amino acid sequence CARPAR (SEQ ID NO: 5) or a peptidomimetic thereof. In one embodiment, the invention provides an isolated peptide which has a length of less than 150 residues and includes the amino acid sequence CARPAR (SEQ ID NO: 5). The isolated peptides and peptidomimetics of the invention which includes the amino acid sequence CARPAR (SEQ ID NO: 5) can have, without limitation, a length of less than 100 residues, 60 residues or 20 residues.

Also provided herein is an isolated peptide or peptidomimetic which has a length of less than 50 residues and includes the amino acid sequence CPKRPR (SEQ ID NO: 6) or a peptidomimetic thereof. In one embodiment, the invention provides an isolated peptide which has a length of less than 50 residues and includes the amino acid sequence CPKRPR (SEQ ID NO: 6). The isolated peptides and peptidomimetics of the invention which include the amino acid sequence SEQ ID NO: 6 can have a variety of lengths including, but not limited to, a length of less than 40 residues or a length of less than 20 residues.

The present invention additionally provides an isolated peptide or peptidomimetic which has a length of less than 400 residues and includes the amino acid sequence CKRAVR (SEQ ID NO: 7) or a peptidomimetic thereof. In one embodiment, the invention provides an isolated peptide which has a length of less than 400 residues and includes the amino acid sequence CKRAVR (SEQ ID NO: 7). A peptide or peptidomimetic of the invention including the amino acid sequence CKRAVR (SEQ ID NO: 7) can have, without limitation, a length of less than 100 residues, a length of less than 60 residues or a length of less than 20 residues.

Further provided by the invention is an isolated peptide or peptidomimetic which includes the amino acid sequence RNSWKPN (SEQ ID NO: 16) or a peptidomimetic thereof. In one embodiment, the invention provides an isolated peptide which includes the amino acid sequence RNSWKPN (SEQ ID NO: 16). As non-limiting examples, an isolated peptide or peptidomimetic of the invention can be conformationally constrained or can have a length of less than 100 residues, a length of less than 60 residues or a length of less than 20 residues. In one embodiment, the invention provides an isolated peptide or peptidomimetic which includes the amino acid sequence CXRNSWKPNZC (SEQ ID NO: 17) or a peptidomimetic thereof, where X=0 to 20 independently selected residues and Z=0 to 20 independently selected residues.

Further provided herein is an isolated peptide or peptidomimetic which includes the amino acid sequence RGSSS (SEQ ID NO: 9) or a peptidomimetic thereof. In one embodiment, the invention provides an isolated peptide containing the amino acid sequence RGSSS (SEQ ID NO: 9). In further embodiments, an isolated peptide or peptidomimetic of the invention containing the amino acid sequence SEQ ID NO: 9 has a length of less than 100 residues, a length of less than 60 residues or a length of less than 20 residues.

The present invention also provides an isolated peptide or peptidomimetic which has a length of less than 400 residues and includes the amino acid sequence RSTRANP (SEQ ID NO: 18) or a peptidomimetic thereof. The invention provides, for example, an isolated peptide which has a length of less than 400 residues and includes the amino acid sequence RSTRANP (SEQ ID NO: 18). As a non-limiting example, an isolated peptide or peptidomimetic of the invention can be conformationally constrained. As a further non-limiting example, an isolated peptide or peptidomimetic of the invention can include the amino acid sequence CRSTRANPC (SEQ ID NO: 11). An isolated peptide or peptidomimetic of the invention further can have any of a variety of lengths. As non-limiting examples, an isolated peptide or peptidomimetic of the invention can have a length of less than 100 residues, less than 60 residues or less than 20 residues. In one embodiment, an isolated peptide or peptidomimetic of the invention includes the amino acid sequence CXRSTRANPZC (SEQ ID NO: 19) or a peptidomimetic thereof, where X=0 to 20 independently selected residues and Z=0 to 20 independently selected residues.

The present invention additionally provides an isolated peptide or peptidomimetic which has a length of less than 400 residues and includes the amino acid sequence PKTRRVP (SEQ ID NO: 20) or a peptidomimetic thereof. In one embodiment, the invention provides a peptide which has a length of 400 residues and includes the amino acid sequence PKTRRVP (SEQ ID NO: 20). An isolated peptide or peptidomimetic of the invention can be, for example, conformationally constrained, or can include the amino acid sequence CPKTRRVPC (SEQ ID NO: 12). In particular embodiments, an isolated peptide or peptidomimetic of the invention containing the amino acid sequence SEQ ID NO: 20 has a length of less than 100 residues, less than 60 residues or less than 20 residues. In a further embodiment, an isolated peptide or peptidomimetic includes the amino acid sequence CXPKTR-RVPZC (SEQ ID NO: 21) or a peptidomimetic thereof, where X=0 to 20 independently selected residues and Z=0 to 20 independently selected residues.

Further provided herein is an isolated peptide or peptidomimetic which has a length of less than 400 residues and includes the amino acid sequence SGMARTK (SEQ ID NO: 22) or a peptidomimetic thereof. In one embodiment, the invention provides a peptide which has a length of less than 400 residues and includes the amino acid sequence SGMARTK (SEQ ID NO: 22). In another embodiment, an isolated peptide or peptidomimetic of the invention is conformationally constrained. In a further embodiment, an isolated peptide or peptidomimetic of the invention includes the amino acid sequence CSGMARTKC (SEQ ID NO: 13). An isolated peptide or peptidomimetic of the invention further can have any of a variety of lengths. As non-limiting examples, an isolated peptide or peptidomimetic of the invention having the amino acid sequence SEQ ID NO: 22 can have a length of less than 100 residues, 60 residues or 20 residues. In one embodiment, the invention provides an isolated peptide or peptidomimetic which includes the amino acid sequence CXSGMARTKZC (SEQ ID NO: 23) or a peptidomimetic thereof, where X=0 to 20 independently selected residues and Z=0 to 20 independently selected residues.

The peptides and peptidomimetics of the invention are provided in isolated form. As used herein in reference to a peptide or peptidomimetic of the invention, the term "isolated" means a peptide or peptidomimetic that is in a form that is relatively free from material such as contaminating polypeptides, lipids, nucleic acids and other cellular material that normally is associated with the peptide or peptidomimetic in a cell or that is associated with the peptide or peptidomimetic in a library or in a crude preparation.

Thus, the invention provides peptides and peptidomimetics including conformationally constrained, bifunctional and multivalent peptides and peptidomimetics as disclosed below. As used herein, the term "peptide" is used broadly to mean peptides, proteins, fragments of proteins and the like. The term "peptidomimetic," as used herein, means a peptide-like molecule that has the activity of the peptide upon which it is structurally based. Such peptidomimetics include chemically modified peptides, peptide-like molecules containing non-naturally occurring amino acids, and peptoids, and have an activity such as the selective homing activity of the peptide upon which the peptidomimetic is derived (see, for example, Goodman and Ro, *Peptidomimetics for Drug Design*, in "Burger's Medicinal Chemistry and Drug Discovery" Vol. 1 (ed. M. E. Wolff; John Wiley & Sons 1995), pages 803-861).

A variety of peptidomimetics are known in the art and are encompassed within the invention including, for example, peptide-like molecules which contain a constrained amino acid, a non-peptide component that mimics peptide secondary structure, or an amide bond isostere. A peptidomimetic that contains a constrained, non-naturally occurring amino acid can include, for example, an α-methylated amino acid; α,α-dialkylglycine or α-aminocycloalkane carboxylic acid; an $N^{\alpha}$-$C^{\alpha}$ cyclized amino acid; an $N^{\alpha}$-methylated amino acid; a β- or γ-amino cycloalkane carboxylic acid; an α,β-unsaturated amino acid; a β,β-dimethyl or β-methyl amino acid; a β-substituted-2,3-methano amino acid; an N-$C^{\delta}$ or $C^{\alpha}$-$C^{\delta}$ cyclized amino acid; a substituted proline or another amino acid mimetic. A peptidomimetic which mimics peptide secondary structure can contain, for example, a nonpeptidic β-turn mimic; γ-turn mimic; mimic of β-sheet structure; or mimic of helical structure, each of which is well known in the art. A peptidomimetic also can be a peptide-like molecule which contains, for example, an amide bond isostere such as a retro-inverso modification; reduced amide bond; methylenethioether or methylene-sulfoxide bond; methylene ether bond; ethylene bond; thioamide bond; trans-olefin or fluoroolefin bond; 1,5-disubstituted tetrazole ring; ketomethylene or fluoroketomethylene bond or another amide isostere. One skilled in the art understands that these and other peptidomimetics are encompassed within the meaning of the term "peptidomimetic" as used herein.

Methods for identifying a peptidomimetic are well known in the art and include, for example, the screening of databases that contain libraries of potential peptidomimetics. For example, the Cambridge Structural Database contains a collection of greater than 300,000 compounds that have known crystal structures (Allen et al., *Acta Crystallogr.* Section B, 35:2331 (1979)). This structural depository is continually updated as new crystal structures are determined and can be screened for compounds having suitable shapes, for example, the same shape as a peptide of the invention, as well as potential geometrical and chemical complementarity to a cognate receptor. Where no crystal structure of a peptide of the invention is available, a structure can be generated using, for example, the program CONCORD (Rusinko et al., *J. Chem. Inf. Comput. Sci.* 29:251 (1989)). Another database, the Available Chemicals Directory (Molecular Design Limited, Informations Systems; San Leandro Calif.), contains about 100,000 compounds that are commercially available and also can be searched to identify potential peptidomimetics of a peptide of the invention, for example, with activity in selectively homing to heart vasculature.

The peptides and peptidomimetics of the invention, including the conformationally constrained, bifunctional and multivalent peptides and peptidomimetics discussed below, can have a variety of lengths. A peptide or peptidomimetic of the invention can have, for example, a relatively short length of less than six, seven, eight, nine, ten, 12, 15, 20, 25, 30, 35, 40, 45, 50, 60, 70 or 80 residues. A peptide or peptidomimetic of the invention also can be useful in the context of a significantly longer sequence as described further below. As used herein, the term "residue" refers to amino acids or analogs thereof. It is understood that a peptide containing, for example, the amino acid sequence SEQ ID NO: 1 includes the specified amino acids as a contiguous sequence not separated by other amino acids.

An isolated peptide or peptidomimetic of the invention can be, without limitation, cyclic or otherwise conformationally constrained. As used herein in reference to a molecule, the term "conformationally constrained" means a molecule, such as a peptide or peptidomimetic, in which the three-dimensional structure is maintained substantially in one spatial arrangement over time. Conformationally constrained molecules can have improved properties such as increased affinity, metabolic stability, membrane permeability or solubility. Methods of conformational constraint are well known in the art and include, without limitation, cyclization.

As used herein in reference to a peptide or peptidomimetic, the term cyclic refers to a structure including an intramolecular bond between two non-adjacent amino acids or amino acid analogs. The cyclization can be effected through a covalent or non-covalent bond. Intramolecular bonds include, but are not limited to, backbone to backbone, side-chain to backbone, and side-chain to side-chain bonds. Methods of cyclization include, without limitation, formation of a disulfide bond between the side-chains of non-adjacent amino acids or amino acid analogs; formation of a lactam bond, for example, between a side-chain group of one amino acid or analog thereof to the N-terminal amine of the amino-terminal residue; and formation of lysinonorleucine and dityrosine bonds.

The present invention also provides an isolated peptide or peptidomimetic containing an amino acid sequence which is a conservative variant, for example, of the sequence CRPPR (SEQ ID NO: 1), CGRKSKTVC (SEQ ID NO: 2), CARPAR (SEQ ID NO: 5), CPKRPR (SEQ ID NO: 6), CKRAVR (SEQ ID NO: 7), CRNSWKPNC (SEQ ID NO: 8), RGSSS (SEQ ID NO: 9), CRSTRANPC (SEQ ID NO: 11), CPKTRRVPC (SEQ ID NO: 12) or CSGMARTKC (SEQ ID NO: 13). In particular embodiments, the invention provides an isolated peptide or peptidomimetic containing an amino acid sequence which is a conservative variant of SEQ ID NO: 1, 2, 5, 6, 7, 8, 9, 11, 12 or 13, in which exactly one amino acid is conservatively substituted. In further embodiments, the invention provides an isolated peptide or peptidomimetic containing an amino acid sequence which is a conservative variant of SEQ ID NO: 1, 2, 5, 6, 7, 8, 9, 11, 12 or 13, in which exactly two amino acids are conservatively substituted. In further embodiments, the invention provides an isolated peptide or peptidomimetic containing an amino acid sequence which is a conservative variant of SEQ ID NO: 1, 2, 5, 6, 7, 8, 9, 11, 12 or 13, in which exactly three, four or five amino acids are conservatively substituted.

As used herein, a "conservative variant" is an amino acid sequence in which a first amino acid is replaced by a second amino acid or amino acid analog having at least one similar biochemical property, which can be, for example, similar size charge hydrophobicity or hydrogen-bonding capacity. For example, a first hydrophobic amino acid can be conservatively substituted with a second (non-identical) hydrophobic amino acid such as alanine, valine, leucine, or isoleucine, or an analog thereof. Similarly, a first basic amino acid can be conservatively substituted with a second basic amino acid such as arginine or lysine, or an analog thereof. In the same way, a first acidic amino acid can be conservatively substituted with a second acidic amino acid such as aspartic acid or glutamic acid, or an analog thereof or an aromatic amino acid such as phenylalanine can be conservatively substituted with a second aromatic amino acid or amino acid analog, for example, tyrosine.

As disclosed herein, a peptide or peptidomimetic that selectively homes to heart vasculature can maintain homing activity in the context of a significantly longer sequence. For example, the 5-mer CRPPR (SEQ ID NO: 1) maintained the ability to home when fused to a phage coat protein, confirming that a peptide of the invention can have selective homing activity when embedded in a larger protein sequence. Thus, the invention provides chimeric proteins which contain a peptide or peptidomimetic of the invention fused to a heterologous protein. In certain embodiments, the invention provides a chimeric protein containing a homing peptide or peptidomimetic that selectively homes to heart vasculature and that specifically binds HLP/CRIP2, receptor clone 9, Sigirr/TIR8, MpcII-3-related protein, or bc-10 fused to a heterologous protein. Heterologous proteins useful in the invention include, without limitation, those having therapeutic activity as well antibodies or antigen-binding fragments thereof. In further embodiments, the invention provides a chimeric protein in which a peptide or peptidomimetic containing the amino acid sequence SEQ ID NO: 1, 2, 5, 6, 7, 8, 9, 11, 12 or 13, or a conservative variant or peptidomimetic of one of these sequences, is fused to a heterologous protein. The term "heterologous," as used herein in reference to a protein fused to a peptide or peptidomimetic of the invention, means a protein derived from a source other than the gene encoding the fused peptide or from which the fused peptidomimetic is derived. A chimeric protein of the invention can have a variety of lengths including, but not limited to, up to 100, 200, 300, 400, 500, 800, 1000 or 2000 residues.

Further provided herein are bifunctional peptides which contain a homing peptide that selectively homes heart vasculature and that specifically binds HLP/CRIP2 (SEQ ID NO: 25), receptor clone 9 (SEQ ID NO: 27), Sigirr/TIR8 (SEQ ID NO: 29), the MpcII-3 related protein SEQ ID NO: 33, or bc-10 (SEQ ID NO: 35), fused to a second peptide having a separate function. Such bifunctional peptides have at least two functions conferred by different portions of the peptide and can, for example, display pro-apoptotic activity in addition to selective homing activity.

The present invention further provides an isolated multivalent peptide or peptidomimetic that includes at least two motifs each independently binding HLP/CRIP2 (SEQ ID NO: 25). Such a multivalent peptide or peptidomimetic can have, for example, at least two motifs each independently containing the amino acid sequence SEQ ID NO: 1 or SEQ ID NO: 2, or a conservative variant or peptidomimetic thereof. The multivalent peptide or peptidomimetic can have, for example, at least three, at least five or at least ten of such motifs, each independently containing the amino acid sequence of SEQ ID NO: 1 or SEQ ID NO: 2, or a conservative variant or peptidomimetic thereof. In particular embodiments, the multivalent peptide or peptidomimetic has two, three, four, five, six, seven, eight, nine, ten, fifteen or twenty identical or non-identical motifs of the amino acid sequence of SEQ ID NO: 1 or SEQ ID NO: 2, or a conservative variant or peptidomimetic thereof. In another embodiment, the multivalent peptide or peptidomimetic contains identical motifs, which consist of the amino acid sequence SEQ ID NO: 1, or a conservative variant or peptidomimetic of this sequence. In yet another embodiment, the multivalent peptide or peptidomimetic contains identical motifs, which consist of the amino acid sequence SEQ ID NO: 2, or a conservative variant or peptidomimetic of this sequence. In still further embodiments, the multivalent peptide or peptidomimetic contains contiguous HLP/CRIP2-binding motifs, which can be identical or non-identical.

Also provided herein is an isolated multivalent peptide or peptidomimetic that includes at least two motifs each independently binding receptor clone 9 (SEQ ID NO: 27). The multivalent peptides or peptidomimetics of the invention can have, for example, at least two motifs each independently containing the amino acid sequence SEQ ID NO: 5 or 6, or a conservative variant or peptidomimetic of these sequences. It is understood that a multivalent peptide or peptidomimetic of the invention can include, for example, at least three, at least five or at least ten of such motifs, each independently containing the amino acid sequence of SEQ ID NO: 5 or 6, or a conservative variant or peptidomimetic thereof. In particular embodiments, the multivalent peptide or peptidomimetic has two, three, four, five, six, seven, eight, nine, ten, fifteen or twenty identical or non-identical motifs of the amino acid sequence of SEQ ID NO: 5 or 6, or a conservative variant or peptidomimetic thereof. A multivalent peptide or peptidomimetic of the invention can include, for example, identical motifs consisting of the amino acid sequence of SEQ ID NO: 5 or 6, or a conservative variant or peptidomimetic of such a sequence. In further embodiments, the multivalent peptide or peptidomimetic contains contiguous receptor clone 9 (SEQ ID NO: 27)-binding motifs, which are identical or non-identical.

The present invention further provides an isolated multivalent peptide or peptidomimetic that includes at least two motifs each independently binding Sigirr/TIR8 (SEQ ID NO: 29). The multivalent peptides or peptidomimetics of the invention can have, for example, at least two motifs each independently containing the amino acid sequence SEQ ID NO: 7, 8 or 9, or a conservative variant or peptidomimetic of these sequences. It is understood that a multivalent peptide or peptidomimetic of the invention can include, for example, at least three, at least five or at least ten of such motifs, each independently containing the amino acid sequence of SEQ ID NO: 7, 8 or 9, or a conservative variant or peptidomimetic thereof. In particular embodiments, the multivalent peptide or peptidomimetic has two, three, four, five, six, seven, eight, nine, ten, fifteen or twenty identical or non-identical motifs of the amino acid sequence of SEQ ID NO: 7, 8 or 9, or a conservative variant or peptidomimetic thereof. A multivalent peptide or peptidomimetic of the invention can include, for example, identical motifs consisting of the amino acid sequence of SEQ ID NO: 7, 8 or 9, or a conservative variant or peptidomimetic of such a sequence. In further embodiments, the multivalent peptide or peptidomimetic contains contiguous Sigirr/TIR8 (SEQ ID NO: 29)-binding motifs, which are identical or non-identical.

Further provided herein is an isolated multivalent peptide or peptidomimetic that includes at least two motifs each independently binding SEQ ID NO: 33. The multivalent peptides or peptidomimetics of the invention can have, for example, at least two motifs each independently containing the amino acid sequence CRSTRANPC (SEQ ID NO: 11), or a conservative variant or peptidomimetic of these sequences. As non-limiting examples, a multivalent peptide or peptidomimetic of the invention can include at least three, at least five or at least ten of such motifs, each independently containing the amino acid sequence of CRSTRANPC (SEQ ID NO: 11), or a conservative variant or peptidomimetic thereof. As further non-limiting examples, a multivalent peptide or peptidomimetic can have two, three, four, five, six, seven, eight, nine, ten, fifteen or twenty identical or non-identical motifs of the amino acid sequence of CRSTRANPC (SEQ ID NO: 11), or a conservative variant or peptidomimetic thereof. A multivalent peptide or peptidomimetic of the invention also can include, for example, identical motifs consisting of the amino acid sequence of SEQ ID NO: 11, or a conservative variant or peptidomimetic of such a sequence. It is understood that a multivalent peptide or peptidomimetic can include contiguous or non-contiguous SEQ ID NO: 33-binding motifs, which can be identical or non-identical.

Also provided by the present invention is an isolated multivalent peptide or peptidomimetic that includes at least two motifs which each independently bind bc10 (SEQ ID NO: 35). The (SEQ ID NO: 35)-binding motifs can be contiguous or non-contiguous, and further can be identical or non-identical. A multivalent peptide or peptidomimetic of the invention can have, for example, at least two motifs each independently containing the amino acid sequence of SEQ ID NO: 12 or SEQ ID NO: 13, or a conservative variant or peptidomimetic of these sequences. As non-limiting examples, a multivalent peptide or peptidomimetic of the invention can include at least three, at least five or at least ten of such motifs, each independently containing the amino acid sequence of SEQ ID NO: 12 or SEQ ID NO; 13, or a conservative variant or peptidomimetic thereof. As further non-limiting examples, a multivalent peptide or peptidomimetic can have two, three, four, five, six, seven, eight, nine, ten, fifteen or twenty identical or non-identical motifs of the amino acid sequence of SEQ ID NO: 12 or SEQ ID NO: 13, or a conservative variant or peptidomimetic thereof. In one embodiment, the invention provides a multivalent peptide or peptidomimetic of the invention which includes identical motifs consisting of the amino acid sequence of SEQ ID NO: 12 or SEQ ID NO: 13, or a conservative variant or peptidomimetic of SEQ ID NO: 12 or SEQ ID NO: 13.

The following examples are intended to illustrate but not limit the present invention.

EXAMPLE I

Identification of Peptides that Selectively Home to Heart Vasculature and Cognate Receptors for the Homing Peptides This example describes the use of ex vivo and in vivo phage selection for identification of peptides that selectively home to heart vasculature, combined with bacterial two-hybridization assays for identification of cognate receptors for the homing peptides.

Ex vivo phage selection for enrichment of cardiac endothelial cells was performed on cell suspensions obtained from murine heart tissue using anti-CD31 magnetic beads for isolation of vascular endothelial cells. A 230-fold enrichment in ex vivo binding to heart cells as compared to non-recombinant phage was observed following three rounds of ex vivo selection (FIG. 1B). Subsequent in vivo selection for homing to the heart resulted in a phage pool that homed to the heart in vivo with an increase of nearly 200-fold relative to the homing of non-recombinant phage. Furthermore, the ex vivo/in vivo selected phage preferentially localized to the heart as compared to other tissues. As shown in FIG. 1C, the enrichment in heart was 20 to 50-fold as compared to phage accumulation in brain, kidney, skin and skeletal muscle.

Isolation of putative receptors for the heart-homing peptides was performed as follows. Peptide-encoding DNA inserts of the heart-homing phage were amplified by polymerase chain reaction (PCR); introduced into a "bait vector" of a bacterial two-hybrid system; and co-transformed into bacteria with a target vector encoding a heart cDNA library. A high stringency screen revealed colonies indicative of a bait-target interaction at a frequency comparable to the positive control, while colony growth was not observed in the absence of either of the two vectors (FIG. 1D). Furthermore, a control for leakiness of the system eliminated 75 out of 100 colonies as likely false positives (FIG. 1E).

In-frame sequences from the 25 remaining candidate receptor cDNAs were analyzed using the NCBI non-redundant database. Of these 25 clones, 19 were proteins abundantly expressed in cardiac muscle, such as myosin, myoglobin, ferritin and oxoglutarate dehydrogenase. The remaining six clones, which represent membrane or cell surface proteins as summarized in Table 1, are putative receptors for heart homing molecules. These results indicate that the combination of ex vivo in vivo phage display and bacterial two-hybrid analysis can rapidly identify heart-homing peptides and their cognate receptors.

Ex vivo and in vivo phage selections were performed as follows. An NNK-encoded $CX_7C$ library displayed on T7Select415-1 phage (Novagen; San Diego, Calif.) was generated as described in Laakkonen et al., *Nat. Med.* 8:751-755 (2002). Phage selections and validations were performed as described in Hoffman et al., "In vivo and ex vivo selections using phage-displayed libraries," in Clarkson and Lowman (Eds.) *Phage Display: A Practical Approach* Oxford, U.K.: Oxford University Press (2004)). Following three rounds of ex vivo selection on heart cells, three rounds of selection were performed in vivo. For ex vivo selections, cell suspensions were prepared from murine heart tissue using collagenase IA at 1 mg/ml (Sigma; St. Louis, Mo.) to disperse the tissue. Cell suspensions were incubated overnight at 4° C. with $5\times10^{10}$ plaque forming units (pfu) of a $CX_7C$ library and subsequently washed to remove unbound phage. Magnetic beads (M450; Dynal; Oslo, Norway) and anti-mouse CD31 (PharMingen; San Diego, Calif.) were used to isolate vascular endothelial cells according to the manufacturer's instructions. Phage bound to the CD31-positive cell population were rescued and amplified in *E. coli* as described in Hoffman et al., supra, 2004.

In vivo panning was performed as follows. The ex vivo-selected phage pool ($5\times10^9$ p.f.u.) was intravenously injected into mice through the tail vein and allowed to circulate for ten minutes before mice were carefully perfused through the left ventricle with DMEM in order to remove unbound intravascular phage. The heart and control tissues (brain, kidney, skin and muscle) were excised, and phage recovered as described in Hoffman et al., supra, 2004. Phage recovered from the heart were reinjected into mice, and the cycle was repeated for a total of three rounds. Non-recombinant phage were injected into a separate mouse as a control in each experiment.

For bacterial two-hybridization experiments, a library of bait plasmids was constructed by PCR amplification of peptide-encoding DNA inserts from the heart-homing phage using primers 5'-TCAGGTGTGATGCTCGG-3' (SEQ ID NO: 36; forward primer) and 5'-GAGTAACTAGTTAACC-3' (SEQ ID NO: 31; reverse primer). PCR products were digested with EcoRI and XhoI, and subcloned into the bait pBT plasmid (Stratagene; La Jolla, Calif.) to generate a recombinant library of baits designated "pBT-hp." pBT-hp plasmids were transformed into XL1-Blue MRF' Kan competent cells, and 2 μl or 5 μl of cells plated on 100 mm LB-chloramphenicol plates to determine the total number of primary transformants. The remaining transformants were pooled and plated on 150 mm LB-chloramphenicol plates. Sequencing was performed on 20 clones, which were found to have proper peptide-encoding inserts. The plates were then scraped, and bacteria harvested. After plating 2 μl and 5 μl of the harvested library in order to determine the size of the amplified library, the pool of pBT-hp plasmids was purified from the pooled bacteria using a commercially available maxiprep DNA column. Purified DNA was used to transform BACTERIOMATCH® Two-Hybrid System reporter strain competent cells according to the manufacturer's instructions (Stratagene; La Jolla, Calif.).

Heart cDNA library plasmids were plate purified by diluting 2 μl of cells containing mouse heart plasmid cDNA library (Stratagene; #982303) into 25 ml SOC medium, and then spreading the cells onto twenty-five 25-cm×25-cm LB-tetracycline plates. Plates were incubated at 30° C. for 24 hours before harvesting of approximately $5\times10^6$ individual clones and subsequent plasmid purification.

Bacterial two-hybridization experiments were performed with the BACTERIOMATCH® Two-Hybrid System (Stratagene) according to the manufacturer's instructions. Briefly, pBT-hp and heart cDNA library plasmids were co-transformed using 50 ng each plasmid. Aliquots (100 μl) of co-transformants were plated on selective LB plates (500 μg/ml carbenicillin) and incubated at 37° C. for 20 hours before scoring the plates for growth. An interaction between a pair of hybrid proteins was indicated by growth on selective plates, as observed for the positive controls, Gal4 and Gal11P hybrid protein. Individual positive colonies from carbenicillin plates were subsequently streaked onto X-gal plates for a secondary screen. After incubation of the cells for 12 to 14 hours, cells were selected that showed a dark blue color with X-gal plates, and were able to grow in the presence of LB-chloramphenicol or LB-tetracycline (markers of the target and bait plasmids) overnight at 30° C. Plasmid DNA was purified, and the reporter strain re-transformed with the putative bait and target plasmids. Clones which grew reproducibly on selective plates were verified as positive. Bait and target inserts were amplified by PCR prior to sequence analysis. Sequences from target vectors were used as queries in a BLASTN search of the nonredundant mouse genome.

EXAMPLE II

Receptor-Peptide Pairs and Peptide Heart-Homing Activity

This example describes the membrane or cell surface expressed proteins which were identified as putative receptors for heart-homing peptides by bacterial two-hybrid analysis with a peptide pool displaying heart homing activity.

Receptor Clone 5

As summarized in Table 1, receptor clone 5 represents the carboxy-terminal 92 amino acids of heart LIM-protein (HLP), also designated cysteine-rich protein 2 (CRIP2) and ESP1. HLP, which is expressed in the vascular heart (Yu et al., *Mech. Dev.* 116:187-192 (2002)) is a LIM domain-containing protein having homology to Crp-1 (Karim et al., *Genomics* 31:167-176 (1996); and van Ham et al., *Genes Cells* 8:631-644 (2003)). Of the five positive colonies from the two-hybrid analysis with the HLP clone, three cognate peptides were identified: CRPPR (SEQ ID NO: 1) was present twice, CGRKSKTVC (SEQ ID NO: 2) once and CGNQVDSRC (SEQ ID NO: 3) twice. After cloning these peptides into the T7Select 415-1 display vector, they were assayed for their ability to home to heart vasculature following intravenous injection. Relative to non-recombinant phage, the CRPPR (SEQ ID NO: 1)-displaying phage homed with more than 300 fold selectivity to the heart (FIG. 2A). As summarized in Table 1, CGRKSKTVC (SEQ ID NO: 2)-phage displayed about 50-fold selectivity in heart-homing while no significant selective homing was observed for phage displaying CGNQVDSRC (SEQ ID NO: 3).

Receptor Clone 9

Receptor clone 9 was also identified as a membrane protein which binds to one or more heart-homing peptides. As indicated in Table 1, receptor clone 9 is an unannotated RIKEN EST. Of the five colonies identified through two-hybrid analysis with receptor clone 9, three peptides, CPSELLLP (SEQ ID NO: 4), CARPAR (SEQ ID NO: 5) and CPKRPR (SEQ ID NO: 6), were identified. The latter two peptides exhibited selective homing to the heart while the first did not (Table 1 and FIG. 2B).

Receptor Clone 15

Receptor clone 15 is a single Ig IL-1 receptor-related protein designated Sigirr or TIR8 (Thomassen et al., *Cytokine* 11:389-399 (1999)). The portion of the protein represented in clone 15 contained the transmembrane domain of Sigirr as well as an amino-terminal extracellular portion of about 190 amino acids. Sigirr is known to be expressed in the epithelia of the kidneys, lungs, gut and other tissues (Thomassen et al., supra, 1999; and Polentarutti et al., *Eur. Cytokine Netw.* 14:211-218 (2003)), although heart or endothelial cell expression has not been reported. As summarized in Table 1, three peptides were identified as binding Sigirr through two-hybrid analysis. These peptides, CKRAVR (SEQ ID NO: 7), CRNSWKPNC (SEQ ID NO: 8), and RGSSS (SEQ ID NO: 9), showed 20 to 30-fold heart homing selectivity (see Table 1 and FIG. 2C).

Receptor Clone 27

Receptor clone 27 is a hypothetical protein annotated as a glutamine-rich region containing protein identified from an olfactory cDNA library. The five bait clones analyzed all encoded the same peptide, CLIDLHVMC (SEQ ID NO: 10), which showed no specific homing to the heart (Table 1 and FIG. 2D).

Receptor Clone 36

Receptor clone 36 contains the entire coding sequence of an unnamed protein product from the RIKEN Fantom set. This receptor is putatively similar to integral membrane protein CII-3 (MpcII-3), a mitochondrial membrane protein that is part of the succinate dehydrogenase complex. Each of the five sequenced colonies identified though binding-activity to clone 36 encoded the same peptide, CRSTRANPC (SEQ ID NO: 5), which displayed about 20-fold heart homing selectivity (Table 1 and FIG. 2E).

Receptor Clone 46

Receptor clone 46 is a portion of the mouse homolog of the human bladder cancer-associated protein 10 (bc10), a small membrane protein which is down regulated as cancer develops from pre-malignant lesions in the bladder (Gromova et al., *Int. J. Cancer* 98:539-546 (2002)). The fragment isolated as receptor clone 46 contains the carboxy-terminal 32 amino acids of the predicted extracellular domain of bc10. Two-hybrid analysis identified two peptides which bound receptor clone 46: CPKTRRVPC (SEQ ID NO: 12) and CSGMARTKC (SEQ ID NO: 13), which demonstrated about 60- and 10-fold heart homing selectivity, respectively (Table 1 and FIG. 2F).

In sum, these results indicate that bacterial two-hybrid analysis, combined with in vivo panning, can be useful for identifying both organ-homing peptides and their cognate receptors.

Individual phage clones were reconstructed as follows. Oligonucleotides that encoded peptides from selected bait plasmids were synthesized, phosphorylated with T4 polynucleotide kinase (PNK; NEB) at 37° C. for one hour, and annealed at a concentration of 0.08 pmol/μl. The annealed inserts were diluted to 0.04 pmol/μl and ligated into T7Select 415-1 arms (Novagen) with T4 ligase overnight at 16° C. The next day, intact recombinant phage were prepared by mixing the ligation reaction with packaging extracts as described by the manufacturer. Inserts were confirmed by sequencing, and individual clones were amplified for ex vivo and in vivo testing as described in Example I above.

EXAMPLE III

Phage-Displayed Heart Homing Peptides Localize to Heart Vasculature

This example demonstrates that the disclosed peptides which selectively home to heart vasculature specifically bind receptors which are expressed in vivo by heart vasculature.

A. Phage-displayed Heart Homing Peptides Co-localize with a Vascular Marker

Further characterization was performed on the five most efficient homing peptides, as indicated by the fold-selectivity summarized in Table 1, and their putative receptors. These homing peptides were analyzed for the ability to selectively bind heart endothelia in vivo and for specific binding to their putative receptors, which also were analyzed for expression in heart endothelia. Each of the phage-displaying a particular homing peptide was individually injected intravenously into mice with fluorescein-conjugated tomato lectin, a blood vessel marker. Localization of phage with anti-T7 antibody showed that phage displaying peptide CRPPR (SEQ ID NO: 1), CARPAR (SEQ ID NO: 5), CKRAVR (SEQ ID NO: 7), CRSTRANPC (SEQ ID NO: 11) or CPKTRRVPC (SEQ ID NO: 12) were present in heart endothelia (FIGS. 3A to C, E and F). The CLIDLHVMC (SEQ ID NO: 10)-displaying phage served as a negative control (FIG. 3D), and was also absent from the heart by phage immunostaining (FIG. 3D). None of the six phage were detected in tissues other than heart under the same conditions.

These results demonstrate that phage displaying peptide CRPPR (SEQ ID NO: 1), CARPAR (SEQ ID NO: 5), CKRAVR (SEQ ID NO: 7), CRSTRANPC (SEQ ID NO: 11) or CPKTRRVPC (SEQ ID NO: 12) localize to heart vasculature in vivo.

Immunohistochemistry was performed as follows. Rat monoclonal anti-mouse CD31 (1:100) was obtained from BD Pharmingen (San Jose, Calif.), and rabbit polyclonal anti-T7 phage (1:500), and chicken anti-mouse CRIP2 IgY (1:100) were obtained from GenWay (San Diego, Calif.). Secondary antibodies, AlexaFluor-488 goat anti-rat IgG (1:1000) and AlexaFluor-594 goat anti-rat or rabbit IgG (1:1000) were obtained from Molecular Probes (Eugene, Oreg.); the secondary antibody GAYFC-AlexaFluor 594 goat anti-IgY Fc (1:250) was obtained from GenWay. Frozen sections were preincubated with blocking buffer (5% normal goat serum and 0.5% BSA in 1×PBS) for one hour, washed three times with PBS, and incubated with the primary antibody of interest overnight at 4° C. After the overnight incubation, secondary antibodies were added and incubated for one hour at room temperature. Slides were washed three times with PBS and mounted in Vectashield Mounting Medium with DAPI (Vector Laboratories; Burlingame, Calif.). Blood vessels were additionally visualized by intravenous injection with *Lycopersicon esculentum* (tomato) lectin conjugated to fluorescein (100 μg in 200 μl of PBS) purchased from Vector Laboratories.

B. Homing Peptides Binds to Cells Transfected with Their Putative Cognate Receptors Full-length cDNAs were constructed for four of the putative heart homing receptors, HLP/CRIP2, Sigirr/TIR8, and MpcII-3-related protein and bc10, and expressed in 293T cells. As shown in FIG. 4, phage displaying each of the four cognate peptides bound to cells transfected with its corresponding putative receptor 300 to 500-fold more than control phage (stippled bar). In addition, phage binding was inhibited in the presence of 100 μg/ml of cognate peptide (solid bar) but not by unrelated homing peptides (open bars). These results confirm that the homing peptide CRPPR (SEQ ID NO: 1) specifically binds to the receptor HLP/CRIP2; the homing peptide CKRAVR (SEQ ID NO: 7) specifically binds to the receptor Sigirr/TIR8; the homing peptide CRSTRANPC (SEQ ID NO: 11) specifically binds to MpcII-3-related protein receptor; and that the homing peptide CPKTRRVPC (SEQ ID NO: 12) specifically binds to the receptor bc10.

Receptor transfections and phage binding assays were performed as follows. 293T cells were transfected with pMH6-derived plasmids (Roche Diagnostics; Indianapolis, Ind.) encoding HLP/CRIP2, Sigirr/TIR8, MpcII-3-related protein and bc10 using the Fugene transfection reagent (Roche Diagnostics). Briefly, 10 μg of plasmid was mixed with 700 μl of serum-free DMEM and 30 μl of Fugene transfection reagent and incubated for 15 minutes at room temperature before the mixture was added to cells. After forty-eight hours, cells were detached from culture dishes using EDTA and washed once with PBS. Phage displaying CRPPR (SEQ ID NO: 1), CKRAVR (SEQ ID NO: 7), CRSTRANPC (SEQ ID NO: 11) or CPKTRRVPC (SEQ ID NO: 12) and nonrecombinant control phage ($1\times10^9$ p.f.u) were incubated with transfected cells for two hours at 4° C. Unbound phage were removed by five washes with 1% BSA in PBS. Bound phage were rescued by addition of bacteria; binding efficiencies were determined by plaque assay as described above.

Peptides for competition assays were synthesized at The Burnham Institute peptide facility using Fmoc chemistry in a solid-phase synthesizer prior to purification by HPLC and confirmation of their identity by mass spectrometry. Fluorescein-conjugated peptides were synthesized as described in Wender et al., *Proc. Natl. Acad. Sci. USA* 97:13003-13008 (2000). Competition assays were performed by addition of 100 μg peptide to the cells and phage, followed by incubation at 4° C. for two hours. After five washes with 1% PBS, bound phage were rescued and quantitated by plaque assay.

C. Receptor mRNAs are Present in Heart Endothelia

Expression of heart homing receptors was studied in tissues using real time PCR and in situ hybridization. Real time-PCR analysis (FIG. 5A) showed that the receptor for peptide SEQ ID NO: 1, HLP/CRIP2, was strongly expressed in the heart and at lower levels in lung and brain. Several other tissues including skeletal muscle were negative for HLP/CRIP2 mRNA. The other heart-homing receptors, Sigirr/TIR8, MpcII-3-related protein and bc10, were also most highly expressed in the heart with lower levels in other tissues (FIG. 5A). The specificity of RT-PCR analysis was confirmed by gel electrophoresis (FIG. 5B) coupled with melting curves and DNA sequence analysis.

In situ hybridization was used to confirm the RT-PCR analysis and determine whether the receptors of interest were expressed on endothelial cells of the heart and other tissues. As shown in FIG. 5C, first row, the HLP/CRIP2 signal was abundant throughout the heart and exhibited a vascular expression pattern (FIG. 5C; first row). Trace level expression was also observed in lung and brain but not in kidney. Although in situ hybridization detected HLP/CRIP2 mRNA expression in the lungs, little CRPPR (SEQ ID NO: 1) phage homing was detected in this tissue (see above).

Figure 5:
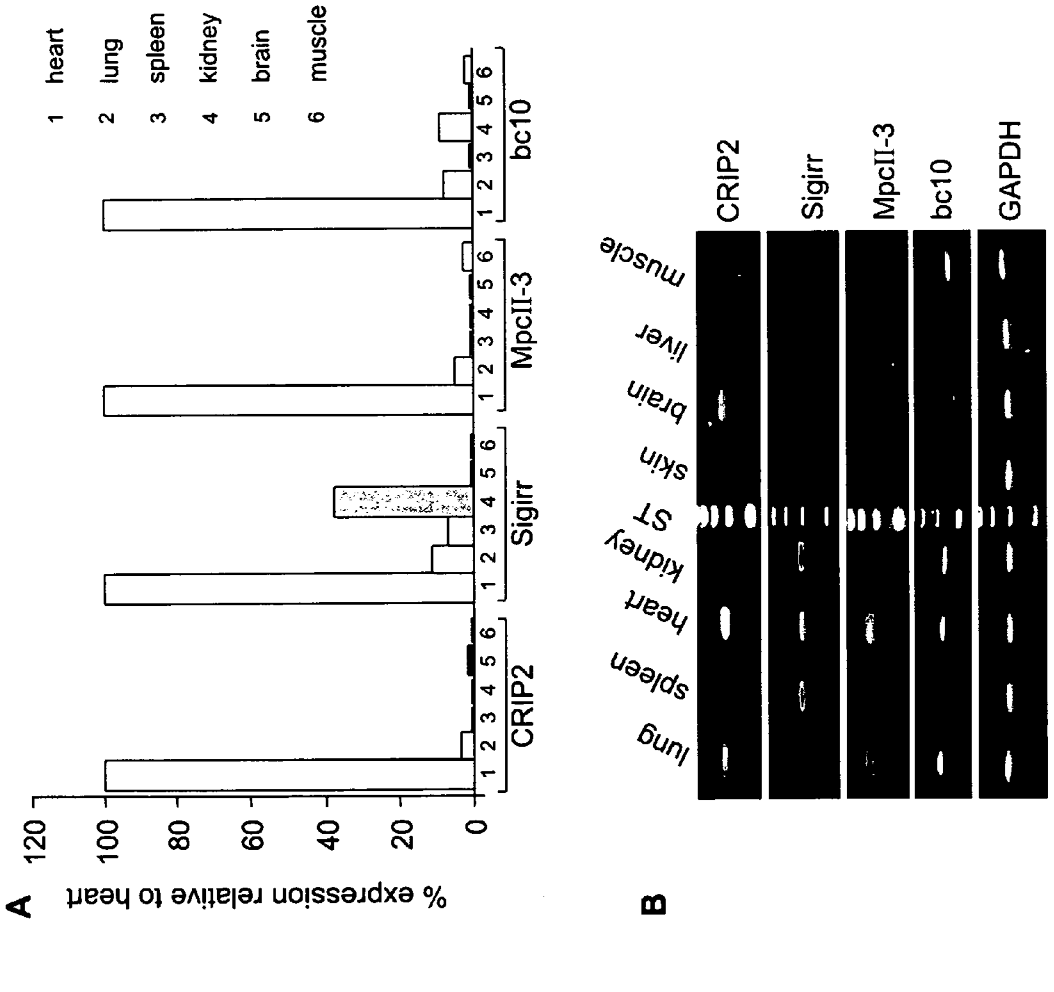
FIG. 5 shows that the receptors for heart-homing peptides are strongly expressed in the heart at the mRNA level and localize to endothelial cells. (A) Real-time PCR results of the four receptor mRNAs in different mouse heart, lung, spleen, kidney, brain and muscle expressed as percentage of the level of same mRNA in the heart (mean from two separate experiments). (B) Real-time PCR products recovered at the end of the analysis and analyzed by agarose gel electrophoresis. ST=100 bp DNA ladder. (C) Localization of receptors by in situ hybridization (red). HLP/CRIP2, Sigirr/TIR8, MpcII-3-related protein, and bc10 were all strongly expressed in endothelial cells in the heart. HLP/CRIP2, MpcII-3-related protein, and bc10 mRNAs were also strongly expressed in cardiac parenchymal. Lung capillaries were additionally clearly positive for Sigirr/TIR8 and MpcII-3-related protein, with some signal observed for HLP/CRIP2 and bc10. Traces of positive staining were occasionally found in other tissues. Magnification 200×.
Figure 5:
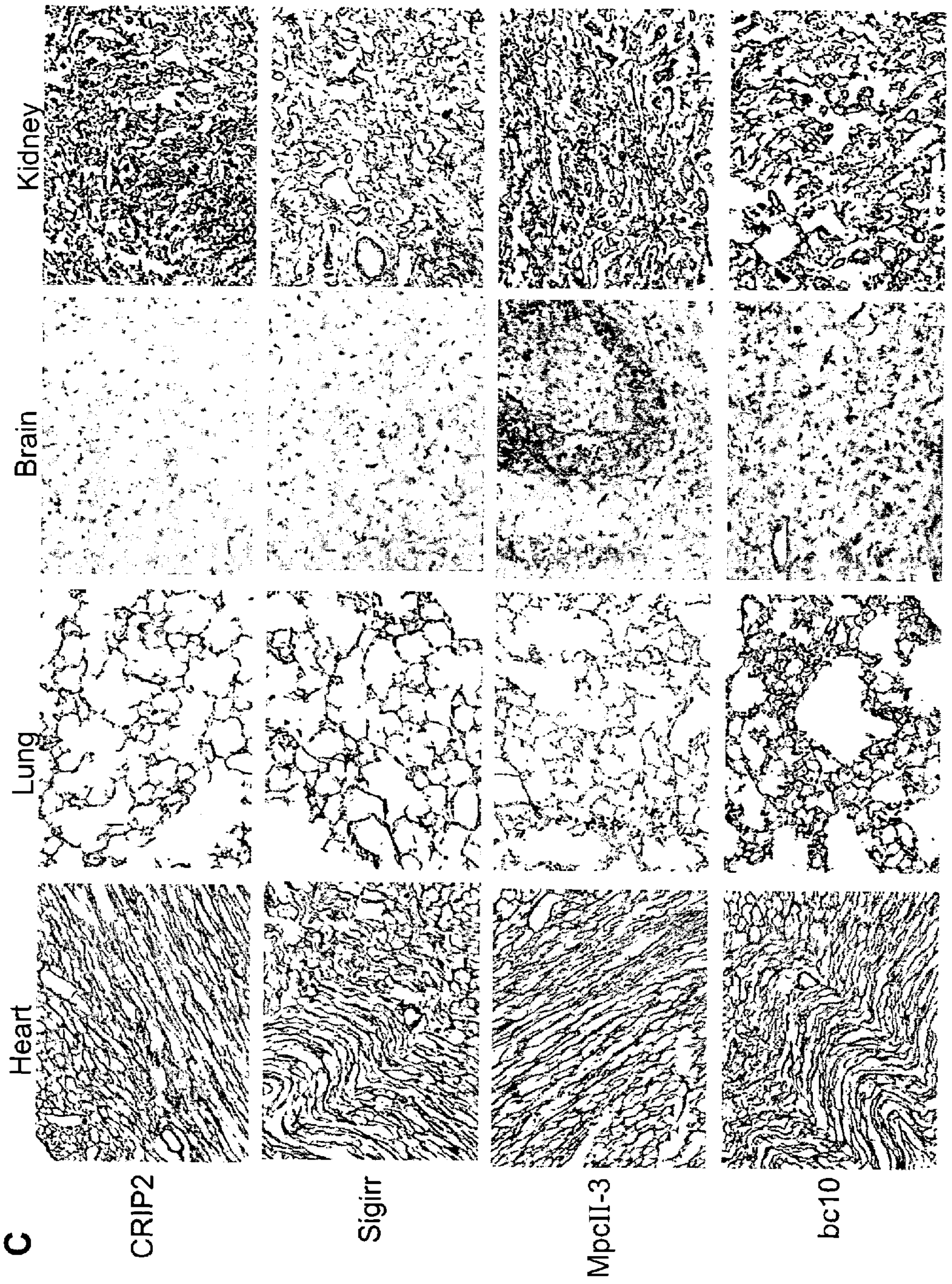

Sigirr/TIR8 in situ hybridization analysis also confirmed the RT-PCR results. The signal was strong in heart vasculature (FIG. 5, second row), weaker in lung and kidney, and absent from the brain. MpcII-3-related protein mRNA was present throughout the heart, most prominently in heart vessels (FIG. 5, third row). MpcII-3-related protein mRNA was also present in some lung blood vessels, although it was absent from brain and kidney. As further shown in FIG. 5C, last row, bc10 mRNA was present in heart blood vessels and was further present in some lung, kidney and muscle blood vessels but not in blood vessels of the brain. In sum, the in situ hybridization results large confirm the RT-PCR results: the four heart-homing receptors are most abundantly expressed in the heart. Furthermore, mRNA for the four heart-homing receptors is localized at the heart endothelium, consistent with localization of the disclosed peptides that selectively home to lung vasculature.

Nonradioactive in situ hybridization was performed essentially as described in St Croix et al., *Science* 289:1197-1202 (2000). Briefly, digoxigenin (DIG)-labeled antisense RNA probes were generated by PCR amplification using an SP6 promoter incorporated into the antisense primer and a T7 promoter incorporated into the sense primer. In vitro transcription was performed with DIG RNA labeling reagents and T7 RNA polymerase (Roche Diagnostics). Frozen tissue sections were fixed with 4% paraformaldehyde, permeabilized with pepsin, and incubated with the RNA probes (200 ng/ml) overnight at 55° C. A horseradish peroxidase (HRP) rabbit anti-DIG antibody (DAKO; Carpinteria, Calif.) was used to catalyze deposition of Biotin-Tyramide using a GenPoint kit for signal amplification (DAKO). Further amplification was achieved by adding horseradish peroxidase (HRP) rabbit anti-biotin (DAKO), biotin-tyramide, and alkaline phosphatase (AP) rabbit anti-biotin (DAKO). Signal was detected with the AP substrate Fast Red TR/Napthol AS-MX (Sigma) in tissue sections counterstained with hematoxylin.

Real time polymerase chain reaction (PCR) assays were performed essentially as described in Galang et al., *J. Biol. Chem.* 279:11281-11292 (2004). Briefly, total RNA was extracted from the organs of interest with the RNeasy kit (Qiagen; Valencia, Calif.), and cDNA prepared from 50 ng of whole RNA using the SuperScript II First-Strand Synthesis System kit (Invitrogen; Carlsbad, Calif.). Real time PCRs were performed using the LightCycler SYBR green DNA master mix (Roche Diagnostics) according to the manufacturer's instructions. For relative expression analysis, the level of the control gene glyceraldehyde phosphate dehydrogenase (GAPDH) was used to normalize receptor expression. GAPDH-normalized expression in heart was defined for each receptor as 100%, and used as the basis of comparison. The specificity of real-time PCR was confirmed by melting curves of each PCR product as well as agarose gel electrophoresis and DNA sequence analysis.

EXAMPLE IV

Intravenously Injected CRPPR (SEQ ID NO: 1) Peptide Co-Localizes with HLP/CRIP2 Protein in Heart Blood Vessels This example demonstrates co-localization of peptide CRPPR (SEQ ID NO: 1) with its cognate receptor, HLP/CRIP2.

The localization of CRPPR (SEQ ID NO: 1) peptide was compared with the expression of HLP/CRIP2 receptor in the heart using an anti-HLP/CRIP2 antibody. As shown in FIGS. 6A and 6B, fluorescence from intravenously injected CRPPR (SEQ ID NO: 1) peptide co-localized extensively with the vascular marker CD31 both in heart blood vessels and in the endocardium. Furthermore, a fluorescein-labeled control peptide was not detected in the heart (FIG. 6C). Anti-HLP/CRIP2 staining also co-localized with CD31 and peptide CRPPR (SEQ ID NO: 1) in heart vessels and heart endocardium (FIGS. 6D to 6F).

The specificity of CRPPR (SEQ ID NO: 1)-phage binding to heart vasculature was assayed using competition assays. As shown in FIGS. 7A and 7B, both CRPPR (SEQ ID NO: 1) peptide and anti-HLP/CRIP2 antibody blocked binding of the CRPPR (SEQ ID NO: 1)-displaying phage to heart-derived cell suspensions in a dose-dependent manner. As negative controls, two other heart-homing peptides had no effect on the CRPPR (SEQ ID NO: 1)-phage binding. Furthermore, co-injected anti-HLP/CRIP2 antibody inhibited in vivo homing of CRPPR (SEQ ID NO: 1)-phage (FIG. 7C). In sum, these results demonstrate that the peptide CRPPR (SEQ ID NO: 1) selectively homes to heart vasculature through specific binding to HLP/CRIP2.

All journal article, reference and patent citations provided above, in parentheses or otherwise, whether previously stated or not, are incorporated herein by reference in their entirety.

Although the invention has been described with reference to the examples provided above, it should be understood that various modifications can be made without departing from the spirit of the invention. Accordingly, the invention is limited only by the following claims.

We claim:

1. An isolated peptide which selectively homes to heart vasculature, said isolated peptide having a length of less than 40 residues and comprising the amino acid sequence CRPPR (SEQ ID NO:1).

2. The isolated peptide of claim 1, having a length of less than 35 residues.

3. The isolated peptide of claim 1, having a length of less than 30 residues.

4. The isolated peptide of claim 1, having a length of less than 25 residues.

5. The isolated peptide of claim 1, having a length of less than 20 residues.

6. The isolated peptide of claim 1, having a length of less than 15 residues.

7. The isolated peptide of claim 1, having a length of less than 12 residues.

8. The isolated peptide of claim 1, having a length of less than 10 residues.

9. The isolated peptide of claim 1, having a length of less than 9 residues.

10. The isolated peptide of claim 1, having a length of less than 8 residues.

11. The isolated peptide of claim 1, having a length of less than 7 residues.

12. The isolated peptide of claim 1, having a length of less than 6 residues.

* * * * *

SEQUENCE LISTING

<160> NUMBER OF SEQ ID NOS: 36

<210> SEQ ID NO 1
<211> LENGTH: 5
<212> TYPE: PRT
<213> ORGANISM: Artificial Sequence
<220> FEATURE:
<223> OTHER INFORMATION: synthetic construct

<400> SEQUENCE: 1

Cys Arg Pro Pro Arg
1 5

<210> SEQ ID NO 2
<211> LENGTH: 9
<212> TYPE: PRT
<213> ORGANISM: Artificial Sequence
<220> FEATURE:
<223> OTHER INFORMATION: synthetic construct

<400> SEQUENCE: 2

Cys Gly Arg Lys Ser Lys Thr Val Cys
1 5

<210> SEQ ID NO 3
<211> LENGTH: 9
<212> TYPE: PRT
<213> ORGANISM: Artificial Sequence
<220> FEATURE:
<223> OTHER INFORMATION: synthetic construct

<400> SEQUENCE: 3

Cys Gly Asn Gln Val Asp Ser Arg Cys
1 5

<210> SEQ ID NO 4
<211> LENGTH: 8
<212> TYPE: PRT
<213> ORGANISM: Artificial Sequence
<220> FEATURE:
<223> OTHER INFORMATION: synthetic construct

<400> SEQUENCE: 4

Cys Pro Ser Glu Leu Leu Leu Pro
1 5

<210> SEQ ID NO 5
<211> LENGTH: 6
<212> TYPE: PRT
<213> ORGANISM: Artificial Sequence
<220> FEATURE:
<223> OTHER INFORMATION: synthetic construct

<400> SEQUENCE: 5

Cys Ala Arg Pro Ala Arg
1 5

-continued

<210> SEQ ID NO 6
<211> LENGTH: 6
<212> TYPE: PRT
<213> ORGANISM: Artificial Sequence
<220> FEATURE:
<223> OTHER INFORMATION: synthetic construct

<400> SEQUENCE: 6

Cys Pro Lys Arg Pro Arg
1 5

<210> SEQ ID NO 7
<211> LENGTH: 6
<212> TYPE: PRT
<213> ORGANISM: Artificial Sequence
<220> FEATURE:
<223> OTHER INFORMATION: synthetic construct

<400> SEQUENCE: 7

Cys Lys Arg Ala Val Arg
1 5

<210> SEQ ID NO 8
<211> LENGTH: 9
<212> TYPE: PRT
<213> ORGANISM: Artificial Sequence
<220> FEATURE:
<223> OTHER INFORMATION: synthetic construct

<400> SEQUENCE: 8

Cys Arg Asn Ser Trp Lys Pro Asn Cys
1 5

<210> SEQ ID NO 9
<211> LENGTH: 5
<212> TYPE: PRT
<213> ORGANISM: Artificial Sequence
<220> FEATURE:
<223> OTHER INFORMATION: synthetic construct

<400> SEQUENCE: 9

Arg Gly Ser Ser Ser
1 5

<210> SEQ ID NO 10
<211> LENGTH: 9
<212> TYPE: PRT
<213> ORGANISM: Artificial Sequence
<220> FEATURE:
<223> OTHER INFORMATION: synthetic construct

<400> SEQUENCE: 10

Cys Leu Ile Asp Leu His Val Met Cys
1 5

<210> SEQ ID NO 11
<211> LENGTH: 9
<212> TYPE: PRT
<213> ORGANISM: Artificial Sequence
<220> FEATURE:
<223> OTHER INFORMATION: synthetic construct

<400> SEQUENCE: 11

Cys Arg Ser Thr Arg Ala Asn Pro Cys
1 5

-continued

<210> SEQ ID NO 12
<211> LENGTH: 9
<212> TYPE: PRT
<213> ORGANISM: Artificial Sequence
<220> FEATURE:
<223> OTHER INFORMATION: synthetic construct

<400> SEQUENCE: 12

Cys Pro Lys Thr Arg Arg Val Pro Cys
1 5

<210> SEQ ID NO 13
<211> LENGTH: 9
<212> TYPE: PRT
<213> ORGANISM: Artificial Sequence
<220> FEATURE:
<223> OTHER INFORMATION: synthetic construct

<400> SEQUENCE: 13

Cys Ser Gly Met Ala Arg Thr Lys Cys
1 5

<210> SEQ ID NO 14
<211> LENGTH: 7
<212> TYPE: PRT
<213> ORGANISM: Artificial Sequence
<220> FEATURE:
<223> OTHER INFORMATION: synthetic construct

<400> SEQUENCE: 14

Gly Arg Lys Ser Lys Thr Val
1 5

<210> SEQ ID NO 15
<211> LENGTH: 11
<212> TYPE: PRT
<213> ORGANISM: Artificial Sequence
<220> FEATURE:
<223> OTHER INFORMATION: synthetic construct
<220> FEATURE:
<221> NAME/KEY: VARIANT
<222> LOCATION: 2, 10
<223> OTHER INFORMATION: Xaa = 0 to 20 independently selected residues

<400> SEQUENCE: 15

Cys Xaa Gly Arg Lys Ser Lys Thr Val Xaa Cys
1 5 10

<210> SEQ ID NO 16
<211> LENGTH: 7
<212> TYPE: PRT
<213> ORGANISM: Artificial Sequence
<220> FEATURE:
<223> OTHER INFORMATION: synthetic construct

<400> SEQUENCE: 16

Arg Asn Ser Trp Lys Pro Asn
1 5

<210> SEQ ID NO 17
<211> LENGTH: 11
<212> TYPE: PRT
<213> ORGANISM: Artificial Sequence
<220> FEATURE:
<223> OTHER INFORMATION: synthetic construct
<220> FEATURE:
<221> NAME/KEY: VARIANT
<222> LOCATION: 2, 10
<223> OTHER INFORMATION: Xaa=0 to 20 independently selected residues -continued

<400> SEQUENCE: 17

Cys Xaa Arg Asn Ser Trp Lys Pro Asn Xaa Cys
 1 5 10

<210> SEQ ID NO 18
<211> LENGTH: 7
<212> TYPE: PRT
<213> ORGANISM: Artificial Sequence
<220> FEATURE:
<223> OTHER INFORMATION: synthetic construct

<400> SEQUENCE: 18

Arg Ser Thr Arg Ala Asn Pro
 1 5

<210> SEQ ID NO 19
<211> LENGTH: 11
<212> TYPE: PRT
<213> ORGANISM: Artificial Sequence
<220> FEATURE:
<223> OTHER INFORMATION: synthetic construct
<220> FEATURE:
<221> NAME/KEY: VARIANT
<222> LOCATION: 2, 10
<223> OTHER INFORMATION: Xaa=0 to 20 independently selected residues

<400> SEQUENCE: 19

Cys Xaa Arg Ser Thr Arg Ala Asn Pro Xaa Cys
 1 5 10

<210> SEQ ID NO 20
<211> LENGTH: 7
<212> TYPE: PRT
<213> ORGANISM: Artificial Sequence
<220> FEATURE:
<223> OTHER INFORMATION: synthetic construct

<400> SEQUENCE: 20

Pro Lys Thr Arg Arg Val Pro
 1 5

<210> SEQ ID NO 21
<211> LENGTH: 11
<212> TYPE: PRT
<213> ORGANISM: Artificial Sequence
<220> FEATURE:
<223> OTHER INFORMATION: synthetic construct
<220> FEATURE:
<221> NAME/KEY: VARIANT
<222> LOCATION: 2,10
<223> OTHER INFORMATION: Xaa= 1 to 20 independently selected residues

<400> SEQUENCE: 21

Cys Xaa Pro Lys Thr Arg Arg Val Pro Xaa Cys
 1 5 10

<210> SEQ ID NO 22
<211> LENGTH: 7
<212> TYPE: PRT
<213> ORGANISM: Artificial Sequence
<220> FEATURE:
<223> OTHER INFORMATION: synthetic construct

<400> SEQUENCE: 22

Ser Gly Met Ala Arg Thr Lys
 1 5

-continued

```
<210> SEQ ID NO 23
<211> LENGTH: 11
<212> TYPE: PRT
<213> ORGANISM: Artificial Sequence
<220> FEATURE:
<223> OTHER INFORMATION: synthetic construct
<220> FEATURE:
<221> NAME/KEY: VARIANT
<222> LOCATION: 2,10
<223> OTHER INFORMATION: Xaa= 0 to 20 independently selected residues

<400> SEQUENCE: 23

Cys Xaa Ser Gly Met Ala Arg Thr Lys Xaa Cys
 1               5                   10


<210> SEQ ID NO 24
<211> LENGTH: 1174
<212> TYPE: DNA
<213> ORGANISM: Mus musculus
<220> FEATURE:
<221> NAME/KEY: CDS
<222> LOCATION: (40)...(666)

<400> SEQUENCE: 24

cggacgcgtg ggtccgcgga ccgaccgagc gcaccgacc atg gcc tcc aag tgt        54
                                           Met Ala Ser Lys Cys
                                            1               5

ccc aag tgt gac aag acc gta tac ttc gct gag aag gtg agc tcc ctg      102
Pro Lys Cys Asp Lys Thr Val Tyr Phe Ala Glu Lys Val Ser Ser Leu
                10                  15                  20

ggc aag gac tgg cac aag ttc tgt ctc aag tgt gag cgc tgc aac aag      150
Gly Lys Asp Trp His Lys Phe Cys Leu Lys Cys Glu Arg Cys Asn Lys
            25                  30                  35

aca ctg acc ccc ggc ggc cat gct gag cat gat ggg aag ccc ttc tgc      198
Thr Leu Thr Pro Gly Gly His Ala Glu His Asp Gly Lys Pro Phe Cys
        40                  45                  50

cac aag ccc tgc tat gcc aca ctg ttt gga ccc aaa ggc gtg aac atc      246
His Lys Pro Cys Tyr Ala Thr Leu Phe Gly Pro Lys Gly Val Asn Ile
    55                  60                  65

ggg ggc gct ggc tcc tac atc tac gag aag cct cag acc gag gcc cct      294
Gly Gly Ala Gly Ser Tyr Ile Tyr Glu Lys Pro Gln Thr Glu Ala Pro
 70                  75                  80                  85

cag gtc act ggc ccc atc gag gtc cct gtg gtg aga act gag gag cga      342
Gln Val Thr Gly Pro Ile Glu Val Pro Val Val Arg Thr Glu Glu Arg
                90                  95                  100

aag acc agc ggc ccc ccc aag ggt ccc agc aaa gcc tct agt gtc acc      390
Lys Thr Ser Gly Pro Pro Lys Gly Pro Ser Lys Ala Ser Ser Val Thr
            105                 110                 115

aca ttc act ggg gag ccc aac atg tgt cct cga tgc aac aag aga gtg      438
Thr Phe Thr Gly Glu Pro Asn Met Cys Pro Arg Cys Asn Lys Arg Val
        120                 125                 130

tac ttc gct gag aag gtg acc tct ctg ggc aag gac tgg cac cgg ccc      486
Tyr Phe Ala Glu Lys Val Thr Ser Leu Gly Lys Asp Trp His Arg Pro
    135                 140                 145

tgc ctg cgc tgt gag cgc tgc tcc aag acc ctg acc cca ggc ggg cat      534
Cys Leu Arg Cys Glu Arg Cys Ser Lys Thr Leu Thr Pro Gly Gly His
150                 155                 160                 165

gct gag cac gat ggc cag ccc tac tgc cac aag cct tgc tat gga ata      582
Ala Glu His Asp Gly Gln Pro Tyr Cys His Lys Pro Cys Tyr Gly Ile
                170                 175                 180

ctc ttt gga ccc aaa gga gtg aat act ggt gct gtg ggc agc tat atc      630
Leu Phe Gly Pro Lys Gly Val Asn Thr Gly Ala Val Gly Ser Tyr Ile
            185                 190                 195
```

-continued

```
tac gac aag gac ccg gaa ggc aca gtt cag ccc tag atctgcagat          676
Tyr Asp Lys Asp Pro Glu Gly Thr Val Gln Pro  *
        200                 205

gctgtcctcg gggtccccct gtttgacccg gaggcaaagt ggcctgttgc ctagtcctgc    736

ctcagcgtgt ctcgcctgca aatccgggac ctaagtggtg gaggagaaag cctggatagt    796

cccagagctt cagccccctt tgtcaccttg gcgtgtcccg tgctgcccac cgtttacttc    856

ctgtctgtgt gcctccgtag ccccatgggt cctgtgttcc tgtgtccctg atagctctcc    916

aaggtgactg tcctatgata tatccctttg cccacacctg cccaccagta ttatttatgc    976

tctgcttgcc ggtgatggcc gtgagctcac agcattccca gggtgatggc tggtgccctt   1036

gcgaggagcc ctctgctggt tccacactac tccctaccta ccctcacatg gttcatggct   1096

atggagactt ttgctgtcaa taaatagttt ggtttgagga ttgcaaaaaa aaaaaaaaaa   1156

aaaaaaaaaa aaaaaaaa                                                 1174


<210> SEQ ID NO 25
<211> LENGTH: 208
<212> TYPE: PRT
<213> ORGANISM: Mus musculus

<400> SEQUENCE: 25

Met Ala Ser Lys Cys Pro Lys Cys Asp Lys Thr Val Tyr Phe Ala Glu
 1               5                  10                  15

Lys Val Ser Ser Leu Gly Lys Asp Trp His Lys Phe Cys Leu Lys Cys
            20                  25                  30

Glu Arg Cys Asn Lys Thr Leu Thr Pro Gly Gly His Ala Glu His Asp
        35                  40                  45

Gly Lys Pro Phe Cys His Lys Pro Cys Tyr Ala Thr Leu Phe Gly Pro
    50                  55                  60

Lys Gly Val Asn Ile Gly Gly Ala Gly Ser Tyr Ile Tyr Glu Lys Pro
65                  70                  75                  80

Gln Thr Glu Ala Pro Gln Val Thr Gly Pro Ile Glu Val Pro Val Val
                85                  90                  95

Arg Thr Glu Glu Arg Lys Thr Ser Gly Pro Pro Lys Gly Pro Ser Lys
            100                 105                 110

Ala Ser Ser Val Thr Thr Phe Thr Gly Glu Pro Asn Met Cys Pro Arg
        115                 120                 125

Cys Asn Lys Arg Val Tyr Phe Ala Glu Lys Val Thr Ser Leu Gly Lys
    130                 135                 140

Asp Trp His Arg Pro Cys Leu Arg Cys Glu Arg Cys Ser Lys Thr Leu
145                 150                 155                 160

Thr Pro Gly Gly His Ala Glu His Asp Gly Gln Pro Tyr Cys His Lys
                165                 170                 175

Pro Cys Tyr Gly Ile Leu Phe Gly Pro Lys Gly Val Asn Thr Gly Ala
            180                 185                 190

Val Gly Ser Tyr Ile Tyr Asp Lys Asp Pro Glu Gly Thr Val Gln Pro
        195                 200                 205


<210> SEQ ID NO 26
<211> LENGTH: 1276
<212> TYPE: DNA
<213> ORGANISM: Mus musculus
<220> FEATURE:
<221> NAME/KEY: CDS
<222> LOCATION: (16)...(840)
```

-continued

```
<400> SEQUENCE: 26

ccagctcaga gcagg atg gcg gcg aca atg tct gaa cct cgg cgt gtg ggc      51
                 Met Ala Ala Thr Met Ser Glu Pro Arg Arg Val Gly
                 1               5                   10

ttc gtg ggt gca ggc cgc atg gcg gag gcc att gcc cga ggc ctc atc       99
Phe Val Gly Ala Gly Arg Met Ala Glu Ala Ile Ala Arg Gly Leu Ile
        15                  20                  25

caa gca ggc aaa gta gaa gct aaa caa gtg ctg gcc agt gca cca acg      147
Gln Ala Gly Lys Val Glu Ala Lys Gln Val Leu Ala Ser Ala Pro Thr
    30                  35                  40

gac aac aac ctc tgc cac ttc agg gct ctg ggt tgc cag act act cac      195
Asp Asn Asn Leu Cys His Phe Arg Ala Leu Gly Cys Gln Thr Thr His
45                  50                  55                  60

tcc aac cat gag gtg ctg caa aac tgc cca ctt gtc atc ttt gcc acc      243
Ser Asn His Glu Val Leu Gln Asn Cys Pro Leu Val Ile Phe Ala Thr
                65                  70                  75

aaa ccc caa gtc ctg cca act gtc ctg gcg gaa gtg gcc ccc ata gtc      291
Lys Pro Gln Val Leu Pro Thr Val Leu Ala Glu Val Ala Pro Ile Val
            80                  85                  90

acc act gag cac atc atc gta tct gtg gct gct ggg atc tct ctg agc      339
Thr Thr Glu His Ile Ile Val Ser Val Ala Ala Gly Ile Ser Leu Ser
        95                  100                 105

aca atg gag ggg ctg tta ccc ccg aac aca cga gta ttg cga gtc tct      387
Thr Met Glu Gly Leu Leu Pro Pro Asn Thr Arg Val Leu Arg Val Ser
    110                 115                 120

ccc aat cta ccc tgc gtt gtc cag gag ggg gcc atg gtg atg gcc cgg      435
Pro Asn Leu Pro Cys Val Val Gln Glu Gly Ala Met Val Met Ala Arg
125                 130                 135                 140

ggc cac cat gct ggg aac gat gac gca gag ctc cta cag aac ttg ctg      483
Gly His His Ala Gly Asn Asp Asp Ala Glu Leu Leu Gln Asn Leu Leu
                145                 150                 155

gaa gcc tgt ggg cag tgc ata gag gtt ccc gag tcc tac gta gat atc      531
Glu Ala Cys Gly Gln Cys Ile Glu Val Pro Glu Ser Tyr Val Asp Ile
            160                 165                 170

cac acc ggt ctc agt ggc agt ggt gtg gcc ttt gtg tgt aca ttt tca      579
His Thr Gly Leu Ser Gly Ser Gly Val Ala Phe Val Cys Thr Phe Ser
        175                 180                 185

gag gcc ctg gct gaa ggt gcc atc aaa atg ggc atg ccc agt ggc ctg      627
Glu Ala Leu Ala Glu Gly Ala Ile Lys Met Gly Met Pro Ser Gly Leu
    190                 195                 200

gcc cac cgc att gct gct cag acc ctg ctg ggg aca gcc aag atg ctg      675
Ala His Arg Ile Ala Ala Gln Thr Leu Leu Gly Thr Ala Lys Met Leu
205                 210                 215                 220

cag cag gaa ggg aag cac cca gcc cag ctt cgg aca gat gtg ctc aca      723
Gln Gln Glu Gly Lys His Pro Ala Gln Leu Arg Thr Asp Val Leu Thr
                225                 230                 235

cca gct gga acc acc atc cat ggg ttg cat gcc cta gag cgg ggc ggt      771
Pro Ala Gly Thr Thr Ile His Gly Leu His Ala Leu Glu Arg Gly Gly
            240                 245                 250

ttt cga gcg gct acc atg agt gcg gtg gaa gca gct acc tgc cgg gct      819
Phe Arg Ala Ala Thr Met Ser Ala Val Glu Ala Ala Thr Cys Arg Ala
        255                 260                 265

aag gag ctc agc aag aag taa ggcaggcctc agatgagact acgggctcct         870
Lys Glu Leu Ser Lys Lys  *
    270

tgcccagctg cagcctctgt ggtgagaata gccctggacg ggagatgtag tgggcagtcc    930

tctaagtgga atggctaatt tatccaagaa gcggtgacta cttgtaagat gctatcaaga    990

cggggttgcc ttgactgtga cattcagtca aggaagaatc gcttgcccct tacctgagat   1050
```

-continued

```
tccagatcct cccttctgca cctcctggcc agttgcagtt gtgtcctcat ggtcacagga   1110

gctggtagaa tatgtctcct gtggaggtgg tagacatcat cctccatgct ggcgtgagac   1170

gtctttggtt gtggctgctt tgggatcacc cacactccgt aagcagcgcc ccgtccatat   1230

tctctaagcc caataaactc attggttctc taaaaaaaaa aaaaaa                  1276


<210> SEQ ID NO 27
<211> LENGTH: 274
<212> TYPE: PRT
<213> ORGANISM: Mus musculus

<400> SEQUENCE: 27

Met Ala Ala Thr Met Ser Glu Pro Arg Arg Val Gly Phe Val Gly Ala
 1               5                  10                  15

Gly Arg Met Ala Glu Ala Ile Ala Arg Gly Leu Ile Gln Ala Gly Lys
            20                  25                  30

Val Glu Ala Lys Gln Val Leu Ala Ser Ala Pro Thr Asp Asn Asn Leu
        35                  40                  45

Cys His Phe Arg Ala Leu Gly Cys Gln Thr Thr His Ser Asn His Glu
    50                  55                  60

Val Leu Gln Asn Cys Pro Leu Val Ile Phe Ala Thr Lys Pro Gln Val
65                  70                  75                  80

Leu Pro Thr Val Leu Ala Glu Val Ala Pro Ile Val Thr Thr Glu His
                85                  90                  95

Ile Ile Val Ser Val Ala Ala Gly Ile Ser Leu Ser Thr Met Glu Gly
            100                 105                 110

Leu Leu Pro Pro Asn Thr Arg Val Leu Arg Val Ser Pro Asn Leu Pro
        115                 120                 125

Cys Val Val Gln Glu Gly Ala Met Val Met Ala Arg Gly His His Ala
    130                 135                 140

Gly Asn Asp Asp Ala Glu Leu Leu Gln Asn Leu Leu Glu Ala Cys Gly
145                 150                 155                 160

Gln Cys Ile Glu Val Pro Glu Ser Tyr Val Asp Ile His Thr Gly Leu
                165                 170                 175

Ser Gly Ser Gly Val Ala Phe Val Cys Thr Phe Ser Glu Ala Leu Ala
            180                 185                 190

Glu Gly Ala Ile Lys Met Gly Met Pro Ser Gly Leu Ala His Arg Ile
        195                 200                 205

Ala Ala Gln Thr Leu Leu Gly Thr Ala Lys Met Leu Gln Gln Glu Gly
    210                 215                 220

Lys His Pro Ala Gln Leu Arg Thr Asp Val Leu Thr Pro Ala Gly Thr
225                 230                 235                 240

Thr Ile His Gly Leu His Ala Leu Glu Arg Gly Gly Phe Arg Ala Ala
                245                 250                 255

Thr Met Ser Ala Val Glu Ala Ala Thr Cys Arg Ala Lys Glu Leu Ser
            260                 265                 270

Lys Lys


<210> SEQ ID NO 28
<211> LENGTH: 1568
<212> TYPE: DNA
<213> ORGANISM: Mus musculus
<220> FEATURE:
<221> NAME/KEY: CDS
<222> LOCATION: (120)...(1349)
```

-continued

```
<400> SEQUENCE: 28

ctacagaaag gagcccttct cagcctgcag tggaccccat ctgctcggtt aaggagccac      60

ggcggtgcca gggagggaaa ccagcgtttg gcctgccgtg aagaggtccc agaagagcc      119

atg gca ggt gtc tgt gac atg gcc cct aat ttc ctt tcc cca tct gaa      167
Met Ala Gly Val Cys Asp Met Ala Pro Asn Phe Leu Ser Pro Ser Glu
 1               5                  10                  15

gac cag gcc ttg ggt ctt gcc ctt ggc aga gaa gtt gct ttg aat tgc      215
Asp Gln Ala Leu Gly Leu Ala Leu Gly Arg Glu Val Ala Leu Asn Cys
            20                  25                  30

aca gct tgg gtg ttc tct agg ccc cag tgt ccc cag cca tca gtg cag      263
Thr Ala Trp Val Phe Ser Arg Pro Gln Cys Pro Gln Pro Ser Val Gln
        35                  40                  45

tgg ctg aaa gat ggt ctg gca ttg ggc aat gga agc cac ttc agc ctc      311
Trp Leu Lys Asp Gly Leu Ala Leu Gly Asn Gly Ser His Phe Ser Leu
    50                  55                  60

cat gag gac ttc tgg gtc agc gcc aac ttc tca gag att gtg tcc agt      359
His Glu Asp Phe Trp Val Ser Ala Asn Phe Ser Glu Ile Val Ser Ser
 65                  70                  75                  80

gtc ctg gtg ctc aac ttg acc aat gca gag gac tat gga acc ttc acc      407
Val Leu Val Leu Asn Leu Thr Asn Ala Glu Asp Tyr Gly Thr Phe Thr
                85                  90                  95

tgt tct gtc tgg aat gtc agc tcc cat tcc ttc act ctt tgg cga gct      455
Cys Ser Val Trp Asn Val Ser Ser His Ser Phe Thr Leu Trp Arg Ala
            100                 105                 110

ggc cct gct ggc cat gtg gct gca gta ctg gct tcc ctc ctg gtc ctg      503
Gly Pro Ala Gly His Val Ala Ala Val Leu Ala Ser Leu Leu Val Leu
        115                 120                 125

gtg gtt ctg ctg ctg gtg gcc ctg ctc tat gtt aag tgt cgg ctg aac      551
Val Val Leu Leu Leu Val Ala Leu Leu Tyr Val Lys Cys Arg Leu Asn
    130                 135                 140

atg ctg ctt tgg tac caa gac act tac ggg gag gtg gag atg aac gat      599
Met Leu Leu Trp Tyr Gln Asp Thr Tyr Gly Glu Val Glu Met Asn Asp
145                 150                 155                 160

ggg aag tta tac gat gcc tac gtg tcc tat agc gac tgc cca gag gac      647
Gly Lys Leu Tyr Asp Ala Tyr Val Ser Tyr Ser Asp Cys Pro Glu Asp
                165                 170                 175

cgc aaa ttt gta aat ttt att ctg aag cct cag ttg gag cgg cgt cgg      695
Arg Lys Phe Val Asn Phe Ile Leu Lys Pro Gln Leu Glu Arg Arg Arg
            180                 185                 190

gga tac aaa ctc ttc cta gag gac cgc gac ctc ttg cct cgc gcg gag      743
Gly Tyr Lys Leu Phe Leu Glu Asp Arg Asp Leu Leu Pro Arg Ala Glu
        195                 200                 205

ccc tct gcc gac ctt ttg gtg aac ctg agt cgc tgt cgg cgt ctc atc      791
Pro Ser Ala Asp Leu Leu Val Asn Leu Ser Arg Cys Arg Arg Leu Ile
    210                 215                 220

gtg gtt ctt tca gat gcc ttc cta agc cgg ccc tgg tgt agc cag agc      839
Val Val Leu Ser Asp Ala Phe Leu Ser Arg Pro Trp Cys Ser Gln Ser
225                 230                 235                 240

ttc cgg gag gga ctg tgc cgc cta ctg gag ctc acc cgc aga cct atc      887
Phe Arg Glu Gly Leu Cys Arg Leu Leu Glu Leu Thr Arg Arg Pro Ile
                245                 250                 255

ttc atc acc ttt gag ggc cag agg cgt gag ccc ata cac cct gct ctc      935
Phe Ile Thr Phe Glu Gly Gln Arg Arg Glu Pro Ile His Pro Ala Leu
            260                 265                 270

cgg ctc ctg cgc cag cac cgc cac ctc gtg acc ctg gtg ctt tgg aag      983
Arg Leu Leu Arg Gln His Arg His Leu Val Thr Leu Val Leu Trp Lys
        275                 280                 285
```

-continued

```
cct ggc tcc gtg act cct tcc tct gat ttt tgg aaa gag cta cag cta      1031
Pro Gly Ser Val Thr Pro Ser Ser Asp Phe Trp Lys Glu Leu Gln Leu
    290                 295                 300

gca ctg cca cgg aag gtg cag tac agg ccg gtg gag gga gac cct caa      1079
Ala Leu Pro Arg Lys Val Gln Tyr Arg Pro Val Glu Gly Asp Pro Gln
305                 310                 315                 320

acc cga ctt cag gat gac aaa gat ccc atg cta atc gtg aga gga cgt      1127
Thr Arg Leu Gln Asp Asp Lys Asp Pro Met Leu Ile Val Arg Gly Arg
                325                 330                 335

gct gcc cag ggc cgg ggc atg gag tca gag ctg gat cca gac cct gag      1175
Ala Ala Gln Gly Arg Gly Met Glu Ser Glu Leu Asp Pro Asp Pro Glu
            340                 345                 350

gga gac ctg ggt gtc cgt gga cct gtc ttt ggg gag cca cca act cca      1223
Gly Asp Leu Gly Val Arg Gly Pro Val Phe Gly Glu Pro Pro Thr Pro
        355                 360                 365

ctg cag gaa acc agg atc tgc ata gga gag agc cac ggc agt gaa atg      1271
Leu Gln Glu Thr Arg Ile Cys Ile Gly Glu Ser His Gly Ser Glu Met
    370                 375                 380

gat gtc tct gac ctc ggc tct cga aac tac agt gca cgg aca gac ttc      1319
Asp Val Ser Asp Leu Gly Ser Arg Asn Tyr Ser Ala Arg Thr Asp Phe
385                 390                 395                 400

tac tgc ctc gtg tct gag gat gat gtg tag cccatatccc agcagcccag       1369
Tyr Cys Leu Val Ser Glu Asp Asp Val  *
                405

accatgagat cacggtggca gcttccaggg tagaggcagc aggcactcct tcctaggatc   1429

acaacccttg cctctatccc tgggcccctc aggaaaggag tgtggcccca gggtgtcaca   1489

aaataaaatc ctgttggttc ctgaaaaaaa aaaaaaaaaa aaaaaaaaaa aaaaaaaaaa   1549

aaaaaaaaaa aaaaaaaaa                                                1568


<210> SEQ ID NO 29
<211> LENGTH: 409
<212> TYPE: PRT
<213> ORGANISM: Mus musculus

<400> SEQUENCE: 29

Met Ala Gly Val Cys Asp Met Ala Pro Asn Phe Leu Ser Pro Ser Glu
 1               5                  10                  15

Asp Gln Ala Leu Gly Leu Ala Leu Gly Arg Glu Val Ala Leu Asn Cys
            20                  25                  30

Thr Ala Trp Val Phe Ser Arg Pro Gln Cys Pro Gln Pro Ser Val Gln
        35                  40                  45

Trp Leu Lys Asp Gly Leu Ala Leu Gly Asn Gly Ser His Phe Ser Leu
    50                  55                  60

His Glu Asp Phe Trp Val Ser Ala Asn Phe Ser Glu Ile Val Ser Ser
65                  70                  75                  80

Val Leu Val Leu Asn Leu Thr Asn Ala Glu Asp Tyr Gly Thr Phe Thr
                85                  90                  95

Cys Ser Val Trp Asn Val Ser Ser His Ser Phe Thr Leu Trp Arg Ala
            100                 105                 110

Gly Pro Ala Gly His Val Ala Ala Val Leu Ala Ser Leu Leu Val Leu
        115                 120                 125

Val Val Leu Leu Leu Val Ala Leu Leu Tyr Val Lys Cys Arg Leu Asn
    130                 135                 140

Met Leu Leu Trp Tyr Gln Asp Thr Tyr Gly Glu Val Glu Met Asn Asp
145                 150                 155                 160
```

-continued

```
Gly Lys Leu Tyr Asp Ala Tyr Val Ser Tyr Ser Asp Cys Pro Glu Asp
                165                 170                 175

Arg Lys Phe Val Asn Phe Ile Leu Lys Pro Gln Leu Glu Arg Arg Arg
            180                 185                 190

Gly Tyr Lys Leu Phe Leu Glu Asp Arg Asp Leu Leu Pro Arg Ala Glu
        195                 200                 205

Pro Ser Ala Asp Leu Leu Val Asn Leu Ser Arg Cys Arg Arg Leu Ile
    210                 215                 220

Val Val Leu Ser Asp Ala Phe Leu Ser Arg Pro Trp Cys Ser Gln Ser
225                 230                 235                 240

Phe Arg Glu Gly Leu Cys Arg Leu Leu Glu Leu Thr Arg Arg Pro Ile
                245                 250                 255

Phe Ile Thr Phe Glu Gly Gln Arg Arg Glu Pro Ile His Pro Ala Leu
            260                 265                 270

Arg Leu Leu Arg Gln His Arg His Leu Val Thr Leu Val Leu Trp Lys
        275                 280                 285

Pro Gly Ser Val Thr Pro Ser Ser Asp Phe Trp Lys Glu Leu Gln Leu
    290                 295                 300

Ala Leu Pro Arg Lys Val Gln Tyr Arg Pro Val Glu Gly Asp Pro Gln
305                 310                 315                 320

Thr Arg Leu Gln Asp Asp Lys Asp Pro Met Leu Ile Val Arg Gly Arg
                325                 330                 335

Ala Ala Gln Gly Arg Gly Met Glu Ser Glu Leu Asp Pro Asp Pro Glu
            340                 345                 350

Gly Asp Leu Gly Val Arg Gly Pro Val Phe Gly Glu Pro Pro Thr Pro
        355                 360                 365

Leu Gln Glu Thr Arg Ile Cys Ile Gly Glu Ser His Gly Ser Glu Met
    370                 375                 380

Asp Val Ser Asp Leu Gly Ser Arg Asn Tyr Ser Ala Arg Thr Asp Phe
385                 390                 395                 400

Tyr Cys Leu Val Ser Glu Asp Asp Val
                405


<210> SEQ ID NO 30
<211> LENGTH: 2591
<212> TYPE: DNA
<213> ORGANISM: Mus musculus

<400> SEQUENCE: 30

aaggccccct cctctggacc ctcctctccg gccagagtca ataccacacc tagatgacat      60

caccctgcca cccataggag ctcaggcttt tgcccatctg agggcgtgct ggccaggtgc     120

cggtggccac cttgtgcgca tgctcggtag ctgcacagtg cgcatgctcg gtagctgcac     180

aatgcatctt aggcagcgtc ctctctgacc cttgtgcaag accatcctgg tattggcgct     240

taggaaggtg taagcagcag agtctggtgt ccacaaaaag aaaaaaaaat gttttagtat     300

agtgagaagc aaaagagaaa caactccaat tgtccttgag cgacgaactt ccatggcaga     360

actttaggtc agtcacaaac agctccgttt tgaatacacg aaaccctcct tgtaccaacc     420

gccgcatgtg tatatccaga tgtgtgggta tacaactgtg gcgattccga attgcatttt     480

tttataacgc gatacgctga catattttag tgaaggtcag cagttttcta acttgtgcct     540

aagaattatt gggaaatgaa aatgcatttc tatctagttt cctggaaata tttctaccca     600

aaatagagaa gaaaagaagg aaagaaagaa agaaaaaaaa agaaaaggta gaagcatgcc     660

tatctgccac cgagtgatcc cctgcttaac ctaaacacca gcgatttgta gatggtaact     720
```

-continued

```
gcctttggaa aaatagcttc ttagtccaac gtgactgggg tcactggtac cccactgcag    780

gatttaatta tgacttctcc tatcccaagg aggtgaaatg tagcggggtg ggggtggggg    840

gaactgagga gtcatatagt ctggccaatg ttttcctcct tagtgattca ttatcttgaa    900

aacaccagtt ttgctccgcc ccccccccca atggcatctt ggaatccatc atcaagctag    960

tattgcgtcc tcaggaaaac atgggagcat gtggcttttg cagcgaggat gagcctgaac   1020

ttggagaaga tcaagaccat gcatggctca tcttcatgac agaggagtct ggtagggcca   1080

ccatggctcc catcacggcc tctcataggc aacacccaca ttttcagttt ggttctatga   1140

ctcgacccca tcaccacaca acaagatggc tcaggggttc cagtcaaggc ttccagaaac   1200

cagcctttct ctcttgggga aaggagggaa gccagttcta aaggtgctag atcatgtccc   1260

ttctgctgga gggtcaccag ggctgcacct ggtagtagtc ccatcttagc cccagaaggc   1320

tctcccagac aagggaacgc agtgaaacgg ccagccggca tccatcagcc actggactgg   1380

cctttgactc taacacggta gaaattagac cacgaaaggt attcatgtag tgctatggaa   1440

gattagaggc atgatccaca aaggagaagt agttttaaca gtcaacacag tgccgataac   1500

gatacctttg tttcctgtat atgacaagag acccttcact ttctaagcat gggcctgcct   1560

gtctttgagc atgcccaaga tgacaagagc aatggagcca agcagaaatg gcctgggcat   1620

ggtgacagct tctccaagga tacacataac tgactcagag gcaaatgtgg tctgtatccc   1680

ttctatggct ctgagttggg cgtccttggc ctcggatgca tctgactgta gccagcttcc   1740

atgggtcttg cccattctgg agacacacac ggtagataca cagagaagaa acaggtcttt   1800

tccctttggc tctgcatgat actgggatac tgagctgggc attccataat agtagcccat   1860

gccatgtcag ttacacacac acacacacaa atatttattc ttttagcagg cacaacctgc   1920

aggtataagt ttggttggcc acttagctct ccaagttagg acccgcctcc acagctgtac   1980

ctgctgaggg caggtactca gcaatacaga gttcgatgtg attatagaat gtggtgcagt   2040

atgttaggct gttgtggtca aagtggtagc aatgttagat ctatgtaccc tcattaggtg   2100

gactagagct ttgccctaat cagcctcgac cctgggcact tgaataaatc tccccatggc   2160

cctggcttcg tttctccatc acagacaccc atcacatatg gtaccccacc tgaattaagt   2220

tctgagatcc aggtggccag agctgctatg attcctctgc ctccatgctg ctatgatccg   2280

gacctctcgg catggaaacc cgagtctgtc tcccttccca ggctggggaa ctgcgccctc   2340

ccctcctgcc acagacagac ctgccaaaca gctctgttct tcatggagtc aggaggtcct   2400

gctggcctgc agcaactcag ttgccttggg ctgggactgc attcttgtga tgtctggatg   2460

ggtttggggc tggaggtcag gtactctggg attagctgaa gggggcacag tgttctttgt   2520

cctgcccctc cggttaactg tgctccatat ttgtgttgaa ctctaaaagc atattaaagt   2580

gaacctgagg g                                                        2591


<210> SEQ ID NO 31
<211> LENGTH: 16
<212> TYPE: DNA
<213> ORGANISM: Artificial Sequence
<220> FEATURE:
<223> OTHER INFORMATION: synthetic construct

<400> SEQUENCE: 31

gagtaactag ttaacc                                                     16
```

-continued

```
<210> SEQ ID NO 32
<211> LENGTH: 3171
<212> TYPE: DNA
<213> ORGANISM: Mus musculus
<220> FEATURE:
<221> NAME/KEY: CDS
<222> LOCATION: (28)...(534)

<400> SEQUENCE: 32

tgatttccgt ccaggccgga actcaag atg gct gcg ttc ttg ctg aga cat gtc      54
                              Met Ala Ala Phe Leu Leu Arg His Val
                               1               5

agc cgt cac tgc ctc cga gcc cac ctg aat gct cag ctt tgt atc aga       102
Ser Arg His Cys Leu Arg Ala His Leu Asn Ala Gln Leu Cys Ile Arg
 10                  15                  20                  25

aat gct gct cct ttg gga acc aca gct aag gag gag atg gag cgg ttc       150
Asn Ala Ala Pro Leu Gly Thr Thr Ala Lys Glu Glu Met Glu Arg Phe
                 30                  35                  40

tgg aag aag aac acg agt tca aac cgt cct ctg tct ccc cat ttg act       198
Trp Lys Lys Asn Thr Ser Ser Asn Arg Pro Leu Ser Pro His Leu Thr
             45                  50                  55

atc tac aaa tgg tct ctt cct atg gca ctg tcc gtt tgc cac cga ggc       246
Ile Tyr Lys Trp Ser Leu Pro Met Ala Leu Ser Val Cys His Arg Gly
         60                  65                  70

tct gga ata gcc ttg agt gga ggg gtc tct ctt ttt ggc ctg tcg gca       294
Ser Gly Ile Ala Leu Ser Gly Gly Val Ser Leu Phe Gly Leu Ser Ala
     75                  80                  85

ctg ctg ctt cct ggg aac ttt gag tca tat ttg atg ttt gtg aag tcc       342
Leu Leu Leu Pro Gly Asn Phe Glu Ser Tyr Leu Met Phe Val Lys Ser
 90                  95                 100                 105

ctg tgt ttg ggg cca aca ctg atc tac tcg gct aag ttt gtg ctt gtc       390
Leu Cys Leu Gly Pro Thr Leu Ile Tyr Ser Ala Lys Phe Val Leu Val
                110                 115                 120

ttc ccg ctc atg tac cac tca ctg aat ggg atc cga cac ttg cta tgg       438
Phe Pro Leu Met Tyr His Ser Leu Asn Gly Ile Arg His Leu Leu Trp
            125                 130                 135

gac cta gga aaa ggc ctg gca ata ccc cag gtc tgg ctg tct gga gtg       486
Asp Leu Gly Lys Gly Leu Ala Ile Pro Gln Val Trp Leu Ser Gly Val
        140                 145                 150

gcg gtc gtg gtt ctt gct gtg ttg tcc tct ggc ggg ctg gcc gcc ctg       534
Ala Val Val Val Leu Ala Val Leu Ser Ser Gly Gly Leu Ala Ala Leu
    155                 160                 165

tgaagagctg gagttcccag cacccctgta catcatcaaa ctgatttata ttcctgttta     594

tcactatccc cacccctccc ccccagcctc ccaggttctc ctgatttgtt tagatgccac     654

atgctttcaa tccccttgga gtgcagtaga gcggcttaaa gacctgttgt agtaagaaag     714

ggtcatcctc cctgggcctg ggagcccttg ctccggttcc acatttgact gatttgtgct     774

gagggtcagc tttccgctgc tttctgctga gacagtggaa acaatgccag ttctgtgacc     834

gccccgagtg ccactgcctg tgggctgctg gcttaaagga cacttctgtc cattggtcag     894

cttagggcct ttagcaccca caccgcgtga ctgagaggag agaggtggag gaggagggat     954

tgtcctgctc agctagaggg agataaagag cagcctggga gcttggagct cgagcctggg    1014

aacagataca gcttttgatg tatgaggaag atcaaaaaaa attgtattaa gtttctgttc    1074

tgtttttcat ttctaggaaa atacaccttt aatgtcatat tttctaatct aaattcttgt    1134

accatcttct ttggaaacga ttaaagtact actcatttta tgcttgactc tttggaatct    1194

agtgacaggt gggtagaaag ggtctaatct ctgcccctcc ctttggatct tggacattta    1254

caccctccag tatggaggga aatagtttgc ccaacaacta ccactgcgaa aaatgaggta    1314
```

-continued atcacaacca agtagtggag agattttggt caaggaaaga acataagaag tcagctaagc 1374 atgcggggag cttttggggt gttgtagggc ccaggcctgt ggatggccag cttggtactt 1434 aagcagacca tttggttatg gacacctagc accagtggag gtggaggcta agggctaaat 1494 agatttgggg ggaggtaggg gaagtagaag agaatttttt aaaagcaggg caggattgga 1554 ggcatcagag ttcttgaaga tggatataca gtgggaaacg ttgcttcttt acccctactg 1614 aggccctgga tccttaccaa gggtgctttg tttgtggtgc taggggtcaa agccaggtcc 1674 ttgtgcgtgt tagcaagcgc tgtaccacta caccagttcc ctagccagga gtgctatttt 1734 gatagatttt tgccaactct ggagtaaaag ctccatcttg ggactagaga tttggttcca 1794 tgatcatatg cccaaggcct gtggttcagt ccccaccacc aagaaaaaca ctactccaag 1854 agattggtca gagcactgga ttggggagtg attgctgggt ggcagttaga caggaagaca 1914 gcatgaactc aaatccgtgg cagcagaggt gggctgggcc caggttaggt tgggttgagg 1974 gctgtttcat tagtctcttg aaatctgtag aaagggattc accatttatc cccaaatggc 2034 ctggaagtct tacccagact accttccagt tggtgtgatc ttgcttctgc ctcccgggtg 2094 catgttacca ccaccctcag ccctcagcct attcctgatc ccaagtagtg tttggcctca 2154 agcaacgatc actaccactc tcctctagac aggccccggg aggtctggtg gtgccaggaa 2214 ttcagcccag ggtcccatcc gtgctaggca agcactgaac ctgagtcagg ccttgccaag 2274 tacccagccc agcccagaca ggcctcgaac tgaccaccca tctgcttcag cctcccaagt 2334 agctggaatt acaggaccat gctaccacat gcgactgctg ggatgtcctg tagatttcat 2394 ccagcgtcaa tcaggttgtc cttagagtag agtcagagtt catggggaaa cacttttgct 2454 ttagacttgg caagggcatt aaattcaaca accagtgcca gaaagatgta tagacagggc 2514 aaaggtcaac atattggcag gctgggaaat taatgtggac atttttactt tttttttga 2574 tggcttctta accagtgatt ggagggaagt aggtcgcctg gcttctttat ttttctcttt 2634 gtaagccggt ctgtaggctt atatatatat atatatatat tttttttaa gatttattta 2694 tttattatat gtaagtacac tatagttgtc ttcagatacc ccagaagagg gcatcagatc 2754 tcattacaga tggttgtgaa ccaccatgtt gttgttagga tttgaactca ggaccttcag 2814 aagagcagac agtgctctta actgctgagc catctctcca gccctggctt atatctttta 2874 aaacctagtt taataagggc atttaaaggc tttaacctcc ctttctaacc taccacccag 2934 cagaggtagt gggaaggaaa ggttagtaac cagacatttt tacttcactg gtctgtcaag 2994 ataactcagc gggtgcaggc tctggccccc aagcctgagg acgcgagttt gatcccagga 3054 tccacgtgtc agaaggatcc accctccgta agctgtctct ggcttccacg tgcttgaggc 3114 acacctccat gcatacgtaa agtcaatgaa tgcgtgtaat aaaggcttgt gtgctct 3171

<210> SEQ ID NO 33
<211> LENGTH: 169
<212> TYPE: PRT
<213> ORGANISM: Mus musculus

<400> SEQUENCE: 33

Met Ala Ala Phe Leu Leu Arg His Val Ser Arg His Cys Leu Arg Ala
1 5 10 15

His Leu Asn Ala Gln Leu Cys Ile Arg Asn Ala Ala Pro Leu Gly Thr
20 25 30

Thr Ala Lys Glu Glu Met Glu Arg Phe Trp Lys Lys Asn Thr Ser Ser
35 40 45

-continued

```
Asn Arg Pro Leu Ser Pro His Leu Thr Ile Tyr Lys Trp Ser Leu Pro
    50                  55                  60

Met Ala Leu Ser Val Cys His Arg Gly Ser Gly Ile Ala Leu Ser Gly
65                  70                  75                  80

Gly Val Ser Leu Phe Gly Leu Ser Ala Leu Leu Leu Pro Gly Asn Phe
                85                  90                  95

Glu Ser Tyr Leu Met Phe Val Lys Ser Leu Cys Leu Gly Pro Thr Leu
            100                 105                 110

Ile Tyr Ser Ala Lys Phe Val Leu Val Phe Pro Leu Met Tyr His Ser
        115                 120                 125

Leu Asn Gly Ile Arg His Leu Leu Trp Asp Leu Gly Lys Gly Leu Ala
    130                 135                 140

Ile Pro Gln Val Trp Leu Ser Gly Val Ala Val Val Val Leu Ala Val
145                 150                 155                 160

Leu Ser Ser Gly Gly Leu Ala Ala Leu
                165


<210> SEQ ID NO 34
<211> LENGTH: 2065
<212> TYPE: DNA
<213> ORGANISM: Mus musculus
<220> FEATURE:
<221> NAME/KEY: CDS
<222> LOCATION: (253)...(516)

<400> SEQUENCE: 34

gttggtggcg agctaaggtg gaggcaagca gcggcggcga cggcgacagt ggcggcagtg      60

ccatggtggg gctcgcagga tccctgctgc cttggtgatc ccgggctgac agccagagag     120

cacagcggct cagctcctgg agagagagtc gaagaaagcg aagggcagcc acctgtgcct     180

gctggctccc attaggtcgg ttcctgcagc ggtgcctggc agccttggtg aaggccctgc     240

ccggcagaga tc atg tat tgc ctc cag tgg ctg ctg ccc gtc ctc ctc atc     291
              Met Tyr Cys Leu Gln Trp Leu Leu Pro Val Leu Leu Ile
               1               5                  10

ccc aag ccc ctc aac ccc gct ctg tgg ttc agc cac tcc atg ttc atg       339
Pro Lys Pro Leu Asn Pro Ala Leu Trp Phe Ser His Ser Met Phe Met
     15                  20                  25

ggc ttc tac ctg ctc agc ttc ctc ctg gaa cgg aaa cct tgc aca ata       387
Gly Phe Tyr Leu Leu Ser Phe Leu Leu Glu Arg Lys Pro Cys Thr Ile
 30                  35                  40                  45

tgt gcc ttg gtt ttc ctg gca gcc ctc ttt ctc atc tgc tat agc tgc       435
Cys Ala Leu Val Phe Leu Ala Ala Leu Phe Leu Ile Cys Tyr Ser Cys
                50                  55                  60

tgg gga aat tgt ttc ctg tac cac tgc tcc gat tcc cca ctt ccg gaa       483
Trp Gly Asn Cys Phe Leu Tyr His Cys Ser Asp Ser Pro Leu Pro Glu
            65                  70                  75

tca gcc cat gac ccc ggt gtt gtg ggc acc taa cgtctgccga gatagcttgc     536
Ser Ala His Asp Pro Gly Val Val Gly Thr  *
         80                  85

caaggaagca gaagacggga ggggaggcat tgacataggt cataaagcat tggagtttca     596

aatcccgcag tcctgcgggt accacattcc taatggagcc ttttggcctg tgatgtttta     656

tccttacaat gtgaataatg gcactgatcg gtgcttctgt tgtagagtcc tgtagtcgtg     716

ggtggtctta tggttgtgtg ttctgtcacc atctgggtcc cggctgacgg attggcccac     776

ccccttgctc attgatttgg ggaatctata cccttgatat gacctgtgtg gatacagtgt     836

agtctcaatg tcacctccat aacccttcct cgtcaagacc ttcctcgttc cctcctcgtc     896
```

-continued

```
ccctttcccc gttttcccct tggttcactt ccaacccctt tcctttttttg gggagcacct    956

gtccaagaca gggcttgttt ttgcacttat ctcaaatttg aagagattgc tgatgcccga   1016

gagcctcgct ttttcatcct tcgttccctt ttgagaaggt gagacggaat catgtctcaa   1076

ctgctcgttg tctgcagacc tccagtattt cctctgcctc atttttaaga aagaagcgat   1136

ggggagacat tgctctttgg cctgggtatc tgggctcctg ccttccagcc cagcctctct   1196

ccctttgctc ttcctcctgt ctctctcagc tgacctaaag gggccacctc atgtctccag   1256

tgcatgctct tcaggaggga gatgtgcagt attctcgtag acccagtggt ccctggctga   1316

gtgaatgaga aagtattaca tttttcatag cagccatgat tcccttggta ggtgtttgga   1376

tatttttgat gtgccctgta tgtatgtgtg cactagtgtc agcgtgtatg tacacacgta   1436

tgtgtgaatg tgtgttgtgt gtgtgtttac ataccaatac atgtgtatat tccttttgaa   1496

gaagctttat tgaatatgtt ctgattttga ggtttagtag tagtagctag ctgtagtagg   1556

tcctgctgca gtttttattt agcatgggga ttgcagagcg accagcacag tggactccaa   1616

ggtggttcag acaagaccca ggggagcagt cgccatcatc ctcccaccag gagcttcctc   1676

attgctgcgc acgtagactg tacactatga agaaaacaca ggaagaaaga tttggtgact   1736

tggtacttgt ttgcttttct ctgcgcttca gaaacaagtg tttgcaaatg agactttctc   1796

ctggccccta cccactgggg atcagcatgg ttgttcttcc agtcggaaat gtaccccccct   1856

cctttccccc tcttgtgtgc aagtgggggg gggggcaggc ataggacaga gctggaagca   1916

ggcttctggg gagtgggact tagaggccac acttgtgaaa cactcggact gctgttgtaa   1976

agcttttatt tctggtgtgt tcgttccaca gctgtttgaa atgtttaata aagctttata   2036

aactttaaaa aaaaaaaaaa aaaaaaaaa                                     2065
```

<210> SEQ ID NO 35
<211> LENGTH: 87
<212> TYPE: PRT
<213> ORGANISM: Mus musculus

<400> SEQUENCE: 35

```
Met Tyr Cys Leu Gln Trp Leu Leu Pro Val Leu Leu Ile Pro Lys Pro
 1               5                  10                  15

Leu Asn Pro Ala Leu Trp Phe Ser His Ser Met Phe Met Gly Phe Tyr
            20                  25                  30

Leu Leu Ser Phe Leu Leu Glu Arg Lys Pro Cys Thr Ile Cys Ala Leu
        35                  40                  45

Val Phe Leu Ala Ala Leu Phe Leu Ile Cys Tyr Ser Cys Trp Gly Asn
    50                  55                  60

Cys Phe Leu Tyr His Cys Ser Asp Ser Pro Leu Pro Glu Ser Ala His
65                  70                  75                  80

Asp Pro Gly Val Val Gly Thr
                85
```

<210> SEQ ID NO 36
<211> LENGTH: 17
<212> TYPE: DNA
<213> ORGANISM: Artificial Sequence
<220> FEATURE:
<223> OTHER INFORMATION: synthetic construct

<400> SEQUENCE: 36

```
tcaggtgtga tgctcgg                                                    17
```